US012643951B2

(12) United States Patent
Vasiljeva et al.

(10) Patent No.: US 12,643,951 B2
(45) **Date of Patent: *Jun. 2, 2026**

(54) MATRIX METALLOPROTEASE-CLEAVABLE AND SERINE OR CYSTEINE PROTEASE-CLEAVABLE SUBSTRATES AND METHODS OF USE THEREOF

(71) Applicant: CytomX Therapeutics, Inc., South San Francisco, CA (US)

(72) Inventors: Olga Vasiljeva, Freemont, CA (US); Michael B. Winter, San Francisco, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 18/415,415

(22) Filed: Jan. 17, 2024

(65) Prior Publication Data

US 2024/0239904 A1 Jul. 18, 2024

Related U.S. Application Data

(63) Continuation of application No. 16/705,124, filed on Dec. 5, 2019, now Pat. No. 12,049,505.

(60) Provisional application No. 62/778,062, filed on Dec. 11, 2018, provisional application No. 62/776,409, filed on Dec. 6, 2018.

(51) Int. Cl.

| | |
|---|---|
| ***C07K 16/28*** | (2006.01) |
| ***A61K 39/00*** | (2006.01) |
| ***A61P 35/00*** | (2006.01) |
| ***C07K 7/06*** | (2006.01) |
| ***C12N 15/11*** | (2006.01) |
| ***C12N 15/62*** | (2006.01) |
| ***C12N 15/63*** | (2006.01) |

(52) U.S. Cl.

CPC .......... *C07K 16/2863* (2013.01); *A61P 35/00* (2018.01); *C07K 7/06* (2013.01); *C12N 15/11* (2013.01); *C12N 15/62* (2013.01); *C12N 15/63* (2013.01); *A61K 2039/505* (2013.01); *C07K 2317/51* (2013.01); *C07K 2317/515* (2013.01); *C07K 2317/92* (2013.01); *C07K 2317/94* (2013.01); *C07K 2319/50* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell |
| 4,485,045 | A | 11/1984 | Regen |
| 4,522,811 | A | 6/1985 | Eppstein et al. |
| 4,544,545 | A | 10/1985 | Ryan et al. |
| 5,013,556 | A | 5/1991 | Woodle et al. |
| 5,030,719 | A | 7/1991 | Umemeto et al. |
| 5,151,510 | A | 9/1992 | Stec et al. |
| 6,551,795 | B1 | 4/2003 | Rubenfield et al. |
| 6,558,728 | B1 | 5/2003 | Poulsen et al. |
| 7,276,497 | B2 | 10/2007 | Chari et al. |
| 7,439,319 | B2 | 10/2008 | Smith et al. |
| 7,442,159 | B1 | 10/2008 | Riechmann et al. |
| 7,465,790 | B2 | 12/2008 | Waldmann et al. |
| 7,504,490 | B1 | 3/2009 | Weinstock et al. |
| 7,666,817 | B2 | 2/2010 | Daugherty et al. |
| 7,935,785 | B2 | 5/2011 | Smith et al. |
| 8,513,390 | B2 | 8/2013 | Stagliano et al. |
| 8,518,404 | B2 | 8/2013 | Daugherty et al. |
| 8,524,220 | B1 | 9/2013 | Bermudes |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,809,504 | B2 | 8/2014 | Lauermann |
| 9,120,853 | B2 | 9/2015 | Lowman et al. |
| 9,127,053 | B2 | 9/2015 | West et al. |
| 9,169,321 | B2 | 10/2015 | Daugherty et al. |
| 9,309,510 | B2 | 4/2016 | La Porte et al. |
| 9,453,078 | B2 | 9/2016 | Stagliano et al. |
| 9,562,073 | B2 | 2/2017 | Moore et al. |
| 10,059,762 | B2 | 8/2018 | Stagliano et al. |

(Continued)

FOREIGN PATENT DOCUMENTS

| | | | |
|---|---|---|---|
| EP | 1 523 503 | B1 | 4/2009 |
| EP | 1 324 771 | B1 | 6/2011 |

(Continued)

OTHER PUBLICATIONS

NCBI Reference Sequence WP_000550713.1 (Year: 1993).*
GenBank MBK8768818.1 (Year: 2022).*
GenBank MFZ5770509.1 (Year: 2025).*
Canadian Office Action for corresponding Canadian Application No. 3,120,327 dated Jan. 23, 2024. (3 pages).
Genbank Accession No. AKP45152.1, Retrieved from internet on Jul. 25, 2018: https://www.ncbi.nlm.nih.gov/protein/Akp45152.
Genbank Accession No. AEL07912.1 [online], Retrieved from internet on Dec. 18, 2017: https://www.ncbi.nlm.nih.gov/ protein/ AEL07912.
Genbank Accession No. YP_005352726.1 [online], Retrieved from internet on Dec. 18, 2017: https://www.ncbi.nlm.nihgov/ protein/ YP_005352726.1.

(Continued)

*Primary Examiner* — Lianko G Garyu
*Assistant Examiner* — Zachary J Miknis
(74) *Attorney, Agent, or Firm* — ROTHWELL, FIGG, ERNST & MANBECK, P.C.

(57) ABSTRACT

The invention relates generally to cleavable polypeptides, method of producing a cleavable moiety (CM) containing polypeptide by culturing a cell under conditions that lead to expression of the polypeptide, methods of manufacturing a cleavable moiety (CM) containing polypeptide by culturing a cell comprising a nucleic acid construct that encodes the cleavable polypeptide to express the cleavable polypeptide, and recovering the cleavable polypeptide, nucleic acids encoding the cleavable polypeptides, and vectors including the nucleic acids encoding the cleavable polypeptides.

20 Claims, 9 Drawing Sheets

Specification includes a Sequence Listing.

(56) References Cited

U.S. PATENT DOCUMENTS

| | | | |
|---|---|---|---|
| 10,077,300 B2 | 9/2018 | Daugherty et al. | |
| 10,118,961 B2 | 11/2018 | Stagliano et al. | |
| 10,138,272 B2 | 11/2018 | Moore et al. | |
| 10,179,817 B2 | 1/2019 | Sagert et al. | |
| 10,233,244 B2 | 3/2019 | Sagert et al. | |
| 10,336,824 B2 | 7/2019 | West et al. | |
| 10,513,558 B2 | 12/2019 | Tipton et al. | |
| 10,669,337 B2 | 6/2020 | Irving et al. | |
| 10,669,339 B2 | 6/2020 | West et al. | |
| 10,745,481 B2 | 8/2020 | West et al. | |
| 10,875,913 B2 | 12/2020 | Stagliano et al. | |
| 11,028,126 B2 | 6/2021 | Moore et al. | |
| 11,267,896 B2 | 3/2022 | Sagert et al. | |
| 12,049,505 B2 * | 7/2024 | Vasiljeva | C07K 16/2863 |
| 2003/0194704 A1 | 10/2003 | Penn et al. | |
| 2003/0219402 A1 | 11/2003 | Rutter | |
| 2003/0236190 A1 | 12/2003 | Pillutla et al. | |
| 2004/0109855 A1 | 6/2004 | Waldmann et al. | |
| 2004/0123343 A1 | 6/2004 | La Rosa et al. | |
| 2004/0214272 A1 | 10/2004 | La Rosa et al. | |
| 2005/0208602 A1 | 9/2005 | Rosen et al. | |
| 2006/0009840 A1 | 1/2006 | Hossainy | |
| 2007/0044171 A1 | 2/2007 | Kovalic et al. | |
| 2007/0218074 A1 | 9/2007 | Man | |
| 2008/0166375 A1 | 7/2008 | Leppla et al. | |
| 2009/0304719 A1 | 12/2009 | Daugherty et al. | |
| 2010/0041588 A1 | 2/2010 | Keay et al. | |
| 2010/0189651 A1 | 7/2010 | Stagliano et al. | |
| 2010/0221212 A1 | 9/2010 | Stagliano et al. | |
| 2011/0214205 A1 | 9/2011 | Dietrich et al. | |
| 2011/0280908 A1 | 11/2011 | Leppla et al. | |
| 2011/0287517 A1 | 11/2011 | Steward et al. | |
| 2012/0149061 A1 | 6/2012 | Stagliano et al. | |
| 2012/0207756 A1 | 8/2012 | Stagliano et al. | |
| 2012/0237512 A1 | 9/2012 | Daugherty et al. | |
| 2012/0237977 A1 | 9/2012 | Daugherty et al. | |
| 2012/0244154 A1 | 9/2012 | Daugherty et al. | |
| 2012/0321626 A1 | 12/2012 | Zhou et al. | |
| 2013/0078203 A1 | 3/2013 | Goksoyr | |
| 2013/0150558 A1 | 6/2013 | Williams et al. | |
| 2013/0266568 A1 | 10/2013 | Brinkmann et al. | |
| 2013/0309230 A1 | 11/2013 | Stagliano et al. | |
| 2013/0332133 A1 | 12/2013 | Horn et al. | |
| 2014/0010810 A1 | 1/2014 | West et al. | |
| 2014/0023664 A1 | 1/2014 | Lowman et al. | |
| 2014/0024810 A1 | 1/2014 | Stagliano et al. | |
| 2014/0045195 A1 | 2/2014 | Daugherty et al. | |
| 2014/0193342 A1 | 7/2014 | Gianneschi et al. | |
| 2014/0255313 A1 | 9/2014 | Vasiljeva et al. | |
| 2014/0363430 A1 | 12/2014 | West et al. | |
| 2015/0005477 A1 | 1/2015 | Lowman et al. | |
| 2015/0087810 A1 * | 3/2015 | Moore | C07K 7/06 530/300 |
| 2016/0122425 A1 | 5/2016 | Daugherty et al. | |
| 2016/0194399 A1 | 7/2016 | Irving et al. | |
| 2016/0228546 A1 | 8/2016 | Stagliano et al. | |
| 2016/0311903 A1 | 10/2016 | West et al. | |
| 2016/0355587 A1 | 12/2016 | West et al. | |
| 2016/0355592 A1 | 12/2016 | Sagert et al. | |
| 2016/0355599 A1 | 12/2016 | Sagert et al. | |
| 2017/0044259 A1 | 2/2017 | Tipton et al. | |
| 2017/0081397 A1 | 3/2017 | Stagliano et al. | |
| 2017/0204139 A1 | 7/2017 | Moore et al. | |
| 2019/0119370 A1 | 4/2019 | Stagliano et al. | |
| 2019/0135864 A1 | 5/2019 | Moore et al. | |
| 2019/0211089 A1 | 7/2019 | Daugherty et al. | |
| 2020/0377602 A1 | 12/2020 | Vasiljeva et al. | |
| 2021/0284721 A1 | 9/2021 | Stagliano et al. | |

FOREIGN PATENT DOCUMENTS

| | | | |
|---|---|---|---|
| EP | 3890764 | A2 | 10/2021 |
| JP | 2015-521589 | A | 7/2015 |
| WO | 1994011026 | A2 | 5/1994 |
| WO | 9915563 | A1 | 4/1999 |
| WO | 2000/024756 | A1 | 5/2000 |
| WO | 2001/023409 | A2 | 4/2001 |
| WO | 2001/034769 | A2 | 5/2001 |
| WO | 2001057182 | A2 | 8/2001 |
| WO | 2001/92523 | A2 | 12/2001 |
| WO | 2001091798 | A2 | 12/2001 |
| WO | 2002012475 | A2 | 2/2002 |
| WO | 2002030460 | A2 | 4/2002 |
| WO | 2002038796 | A1 | 5/2002 |
| WO | 2002/077183 | A2 | 10/2002 |
| WO | 2003/004681 | | 1/2003 |
| WO | 2003038083 | A1 | 5/2003 |
| WO | 2003/068934 | | 8/2003 |
| WO | 2004009638 | A1 | 1/2004 |
| WO | 2006/068975 | | 6/2006 |
| WO | 2006110599 | A2 | 10/2006 |
| WO | 2007/047995 | A2 | 4/2007 |
| WO | 2007105027 | A1 | 9/2007 |
| WO | 2008052187 | A2 | 5/2008 |
| WO | 2008/083312 | A2 | 7/2008 |
| WO | 2008/149143 | A2 | 12/2008 |
| WO | 2008/149147 | A2 | 12/2008 |
| WO | 2008/149148 | A2 | 12/2008 |
| WO | 2008/149149 | A2 | 12/2008 |
| WO | 2008/149150 | A2 | 12/2008 |
| WO | 2009025846 | A2 | 2/2009 |
| WO | 2010046628 | A1 | 4/2010 |
| WO | 2010081173 | A2 | 7/2010 |
| WO | 2010/091122 | A1 | 8/2010 |
| WO | 2010088691 | A2 | 8/2010 |
| WO | 2010096838 | A2 | 8/2010 |
| WO | 2010129609 | A2 | 11/2010 |
| WO | 2011028698 | A2 | 3/2011 |
| WO | 2011/151426 | A2 | 12/2011 |
| WO | 2011/161260 | A1 | 12/2011 |
| WO | 2012/058606 | A1 | 5/2012 |
| WO | 2012/158818 | A2 | 11/2012 |
| WO | 2012156919 | A1 | 11/2012 |
| WO | 2013/003649 | A2 | 1/2013 |
| WO | 2013/138522 | A3 | 9/2013 |
| WO | 2013163631 | A1 | 10/2013 |
| WO | 2013192546 | A1 | 12/2013 |
| WO | 2013192550 | A2 | 12/2013 |
| WO | 2014026136 | A2 | 2/2014 |
| WO | 2014052462 | A2 | 4/2014 |
| WO | 2014107599 | A2 | 7/2014 |
| WO | 2014176284 | A1 | 10/2014 |
| WO | 2014/197612 | A1 | 12/2014 |
| WO | 2014/200910 | A2 | 12/2014 |
| WO | 2014/202616 | A2 | 12/2014 |
| WO | 2014193973 | A2 | 12/2014 |
| WO | 2015048329 | A2 | 4/2015 |
| WO | 2015116933 | A2 | 8/2015 |
| WO | 2016014974 | A2 | 1/2016 |
| WO | 2016/065326 | A2 | 4/2016 |
| WO | 2016118629 | A1 | 7/2016 |
| WO | 2016179257 | A2 | 10/2016 |
| WO | 2016/210447 | A1 | 12/2016 |
| WO | 2017/191274 | A2 | 11/2017 |
| WO | 2018/071672 | A1 | 4/2018 |
| WO | 2020/077267 | A1 | 4/2020 |
| WO | 2020118109 | A2 | 6/2020 |

OTHER PUBLICATIONS

Geneseq Assession No. AAB46481, B. brevis tyrocidn sythetases activating domain 9 (Apr. 9, 2001).

GENPEPT Assession No. P0C9K2.1, RecName: Full=Protein MGF 110-14L; Flags: Precursor (Sep. 28, 2018); https://www.ncbi.nlm.nih.gov/ protein/229544532?sat=12&satkev =1040226.

Gerspach et al., "Target-selective activation of a TNF prodrug by urokinase-type plasminogen activator (uPA) mediated proteolytic processing at the cell surface", Cancer Immunol. (2006) 55(12):1590-1600.

Gerspach et al., "Restoration of membrane TNF-like activity by cell surface targeting and matrix metalloproteinase-mediated processing of a TNF prodrug", Cell Death and Differentiation (2006) 13(2):273-284.

(56) References Cited

OTHER PUBLICATIONS

Harris et al., "Rapid and general profiling of protease specificity by using combinatorial fluorogenic substrate libraries", PNAS (2000) 97(14): 7754-7759.
Henikoff et al., "Amino acid substitution matrices from protein blocks", Proc Natl Acad Sci USA (1992) 89(22):10915-10919.
Hwang et al., "Hepatic uptake and degradation of unilamellar sphingomyelin/cholesterol liposomes: a kinetic study", Proc. Natl Acad. Sci. USA (1980) 77(7):4030-4034.
Irving, "Probodies Empower a New Generation of Antibody Immunotherapies," presented at Keystone Symposia on Molecular and Cellular Biology, Feb. 2015.
Jabaiah et al., "Directed evolution of protease beacons that enable sensitive detection of endogenous MT1-MMP activity in tumor cell lines", Chem. Biol. (2011) 18(3):392-401.
Jansen et al., "Immunotoxins: hybrid molecules combining high specificity and potent cytotoxicity", Immunological Reviews (1982) 62:185-216.
Jeong et al., "Recombinant antibodies: Engineering and production in yeast and bacterial hosts", Biotechnol. J. (2011) 6(1):16-27.
Kawato et al., "Hypothetical protein [Pseudomonas phage PPpW-3]" Accession No. VP_008873205, Dec. 9, 2013.
Ke et al., "Optimal Subsite Occupancy and Design of a Selective Inhibitor of Urokinase", J. Biol. Chem., (1997) 272 (33):20456-20462.
Ke et al., "Distinguishing the specificities of closely related proteases role of p3 in substrate and inhibitor discrimination between tissue-type plasminogen activator and urokinase ", J. Bio. Chem. (1997) 272(26):16603-16609.
Killen and Lindstrom, "Specific killing of lymphocytes that cause experimental autoimmune myasthenia gravis by ricin toxin-acetylcholine receptor conjugates", J. Immunol. (1984) 133(5):2549-2553.
Kopylov et al., "Methods of quantitative proteomics", Biomed Khim. (2007) 53(6):613-643. (English Abstract only).
Kridel et al., "Substrate hydrolysis by matrix metalloproteinase-9", J. Biol. Chem. (2001) 276(23):20572-20578 (Epub Mar. 14, 2001).
Kridel et al., "A Unique Substrate Binding Mode Discriminates Membrane Type-I Matrix Metalloproteinase from Other Matrix Metalloproteinases", J. Biol. Chem. (2002) 277(26): 23788-23793.
LaPlanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates", Nucl. Acids Res. (1986) 14(22):9081-9093.
Liu et al., "Intermolecular complementation achieves high-specificity tumor targeting by anthrax toxin", Nature Biotech. (2005) 23(6):725-730.
Lopez-Otin et al., "Protease Degradomics: A New Challenge for Proteomics", Nature Rev. Mol. Cell Biol. (2002) 3:509-519.
Malmqvist M., "Biospecific interaction analysis using biosensor technology", Nature (1993) 361(6408):186-187.
Marasco et al., "Design, intracellular expression, and activity of a human anti-human immunodeficiency virus type 1 gp120 single-chain antibody", Proc. Natl. Acad. Sci. USA (1993) 90(16):7889-7893.
Martin et al., "Irreversible coupling of immunoglobulin fragments to preformed vesicles. An improved method for liposome targeting", J. Biol. Chem. (1982) 257(1):286-288.
Maytansinoid DM4, Retrieved from internet on Mar. 17, 2016, (9 pages): https://pubchem.ncbi.nlm.nih.gov/compound/46926355#section=Top.
Mitra and Lawton, "Reagents for the crosslinking of proteins by equilibrium transfer alkylation", J. Amer. Chem. Soc. (1979) 101(11):3097-3110.
Nangia-Makker et al., "Galectin-3 cleavage: a novel surrogate marker for matrix metalloproteinase activity in growing breast cancers", Cancer Res. (2007) 67(24): 11760-11768.
Paul, W., Fundamental Immunology, (3rd Edition, Lippincott Williams & Wilkins, (1993) p. 292-295).
Portolano et al., Lack of promiscuity in autoantigen-specific H and L chain combinations as revealed by human H and L chain "roulette", J. Immunol. (1993) 150(3):880-887.
Powell et al. "Compendium of excipients for parenteral formulations" PDA J Pharm Sci Technol. (1998) 52(5):238-311.
Bendig, Mary M., "Humanization of Rodent Monoclonal Antibodies by CDR Grafting", Methods: A Companion to Methods in Enzymology (1995); 8:83-93.
Colman, Peter M. "Effects of amino acid sequence changes on antibody-antigen interactions", Res. Immunol. (1994) 145(1 ): 33-36.
Murphy et al., "Enhancing recombinant antibody performance by optimally engineering its formal", J_ Immunol. Methods (2018) 463:127-133.
Rudikoff et al., "Single Amino Acid Substitution altering antigen-binding specificity", Proc. Nall. Acad. Sci. USA (1982) 79(6):1979-1983.
Juliano et al. "Differences in substrate specificities between cysteine protease CPB isoforms of Leishmania mexicana are mediated by a few amino acid changes" Eur. J. Biochem. 271 :3704-3714. (Year: 2004).
Neitzel J "Enzyme Catalysis: The Serine Proteases" Nature Education 3:21 (Year: 2010).
De Groot N.: "AsnC family protein from Sedimentitalea nanhaiensis", Apr. 12, 2017 (Apr. 12, 2017), XP093016536, Retrieved from the Internet: URL:https://rest.uniprot.org/unisave/AOA117CZR5?format=txt&versions=3, 1 page.
Communication pursuant to Rule 164(2)(b) and Article 94(3) EPC issued in EP 19 828 467.1 dated Feb. 24, 2023, 18 pgs.
Russian Office Action issued on Dec. 21, 2022 in RU Application No. 2020106752, 20 pages.
Japanese Office Action issued on Sep. 20, 2022 in JP Application No. 2021-016630, 7 pages.
Khantasup et al., "Design and Generation of Humanized Single-chain Fv Derived from Mouse Hybridoma for Potential Targeting Application", Monoclon. Antib. Immunodiagn. Immunother. (2015) 34(6):404-417.
Liu et al. "Targeting of Tumor Cells by Cell Surface Urokinase Plasminogen Activator dependent Anthrax Toxin," J. Biol. Chem. (2001) 276(21):17976-17984.
Yarmolinskaya et al. "Matrix Metalloproteinases and Inhibitors: Classification, Mechanism of Action," J. Obstetrics and Women's Diseases (2012 61(1): 113-125.
Non-Final Office Action for corresponding U.S. Appl. No. 18/742,845 dated Jun. 2, 2025. (11 pages).
Notice of Reasons for Rejection for corresponding Japanese Patent Application No. 2024-230664 mailed May 27, 2025 (14 pages).
Russian Office Action issued in corresponding Russian Application No. 2020106752 dated Mar. 21, 2024 (21 pages).
Ohkubo, et al., "Identification of Substrate Sequences for Membrane Type-1 Matrix Metalloproteinase Using Bacteriophage Peptide Display Library", Biochemical and Biophysical Research Communications; 1999; vol. 266, No. 2; 308-313.
Final Office Action for corresponding U.S. Appl. No. 18/474,103, dated Dec. 2, 2024 (20 pages).
Final Office Action for corresponding U.S. Appl. No. 18/474, 134, dated Dec. 18, 2024 (18 pages).
Non-Final Office Action for corresponding U.S. Appl. No. 18/062,619, dated Apr. 22, 2025 (20 pages).
Biological Macromolecules; Libre Texts Biology (https://bio.libretexts.org/Bookshelves/Introductory _and_ General_Biology/General_Biology _1e_(OpenStax)/ 1%3A_The_Chemistry_of_Life/3%3A_Biological_Macromolecules; accessed Dec. 10, 24. (1 page).
Australian Office Action for corresponding Australian Application No. 2019394972 dated Jun. 24, 2025. (8 pages).
GenBank AAK23786; UniProtKB_Q9A7B4_NPL; Complete genome sequence of Caulobacter vibrioides CB15; Proc. Natl. Acad. Sci, 98:4136-4141 (2001); https://rest.uniprot.org/uniprotkb/Q9A7B4.txt; 1 page.
GenBank ABV27395; UniProtKB_A8DJD6; "Candidatus Chloracidobacterium thermophilum: an aerobic photorophic

(56) References Cited

OTHER PUBLICATIONS

Acidobacterium"; hypothetical protein YS_M60-F11.029 ; Science 317:523-526 (2007); https://rest.uniprot.org/uniprotkb/A8DJD6.txt; 1 page.
Michel et al., "Selective RNA Binding by a Single CCCH Zinc-Binding Domain from Nup475 (Tristetraprolin)", Biochemistry; Apr. 29, 2003; vol. 42, No. 16; pp. 4626-4630 (Abstract).
Yu J. et al. "Genome sequence of Candida maltosa Xu316, a potential industrial strain for xylitol and ethanol production"; UniProtKB_M3HF54, May 29, 2013; Publications for M3HF54: [Found on Dec. 20, 2022] URL: https://rest.uniprot.org/unisave/M3HF54?format=txt&versions=2]; 1 page.
"Uncharacterized protein from Saprolegnia parasitica", ID : A0A067BQW3_SAPPC, Uniprot,: https://rest.uniprot.org/unisave/A0A067BQW3?format=txt&versions=1; Sep. 3, 2014.
"AsnC family protein from Sedimentitalea nanhaiensis", ID: A0A117CZR5_9RHOB, Uniprot,: https://rest.uniprot.org/unisave/A0A117CZR5?format=txt&versions=3; Jun. 7, 2017.
Oshone, R., "Uncharacterized protein from Frankia Torreyi", Retrieved from the Internet, XP055665772, Nov. 17, 2018, URL: http://www.uniproto.org/uniprot/A0A0D8, 1 page.
Durrens, "Clavispora lusitaniae hypothetical protein", Retrieved from the Internet, XP055665684, Jun. 15, 2017, URL: https://www.ebi.ac.uk/ena/browser/api/embl/0VF07168.1?linelimit=1000, 2 pages.
Chen et al., "Selective antibody activation through protease-activated pro-antibodies that mask binding sites with inhibitory domains", Scientific Reports, vol. 7, No. 1, Sep. 14, 2017, 12 pages.
Kukreja, "The hight throughput multiplexed peptide-centric profiling illustrates both the substrate cleavage redundancy and specificity in the MMP family", Chem Bio, vol. 22, No. 8, Aug. 20, 2015, pp. 1122-1133.
Anonymous, "Uncharacterized protein form Saprolegnia diclina", Retrieved from the Internet, XP055674716, URL: https://www.uniprot.org/uniprot/T0RF53.txt?version=5, 1 page.
International Search Report issued in PCT/2019/064779, dated Jun. 23, 2020, 9 pages.
UniProt A0A0D8BN56, Oshone, R. et al., "Permanent Draft Genome Sequences for Two Variants of *Frankia* sp. Strain Cpl1, the First Frankia Strain Isolated from Root Nodules of Comptonia peregrina", 2016, [online] [retrieved Jun. 13, 2023] Found at https://rest.uniprot.org/uniprotkb/A0A0D8BN56.txt?version=12.
A.A. Yarilin, Fundamentals of Immunology: Textbook. - M .: Medicine, 1999, 608 p., pp. 172-174.
Office Action issued in Eurasian Patent Application No. 202191582 on Jun. 13, 2023, 16 pages.
Prudova et al., "Multiplex N-terminome analysis of MMP-2 and MMP-9 substrate degradomes by iTRAQ-TAILS quantitative proteomics", Mol. Cell Proteomics (2010) 9(5):894-911.
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", Cancer Res. (1984) 44:201-208.
Ratnikov et al., "Basis for substrate recognition and distinction by matrix metalloproteinases", Proc. Natl. Acad. Sci. USA (2014) 111(4):E4148-55.
Rothberg et al., "An integrated semiconductor device enabling non-optical genome sequencing", Nature (2011) 475 (7356):348-52.
Scheraga, H.A., "Predicting Three-Dimensional Structures of Oligopeptides" Rev. Computational Chem., (vol. 3, K. B. Lipkowitz and D.B. Boyd (Eds.), John Wiley & Sons, Inc., Hoboken, NJ, (1992)).
Stec et al., "Automated solid-phase synthesis, separation, and stereochemistry of phosphorothioate analogs of oligodeoxyribonucleotides", J. Am. Chem. Soc. (1984) 106(20):6077-6079.
Stein et al., "Physicochemical properties of phosphorothioate oligodeoxynucleotides", Nucl. Acids Res. (1988) 16 (8):3209-3221.
Takeuchi T et al. "Cellular Location of Membrane-type Serine Protease 1 and Identification of Protease-activated Receptor-2 and Single-chain Urokinase-type Plasminogen Activator as Substrates", J. Biol. Chem. (2000) 275(34):26333-26342.
Tateno et al. (Jul. 24, 1998) "Isolation and Characterization of Rhamnose-binding Lectins from Eggs of Steelhead Trout (*Oncorhynchus mykiss*) Homologous to Low Density Lipoprotein Receptor Superfamily", J. Biol. Chem. (1998) 273(30):19190-19197.
Thornton et al., "Prediction of progress at last", Nature (1991) 354:105.
Toshihiko et al., "Cellular Location of Membrane-type Serine Protease 1 and Identification of Protease-activated Receptor-2 and Single-chain Urokinase-type Plasminogen Activator as Substrates", J. Biol. Chem. (2000) 274 (34):26333-26342.
Turk et al., "Determination of protease cleavage site motifs using mixture-based oriented peptide libraries", Nat. Biotechnol. (2001) 19(7):661-7.
Uhlmann and Peyman, "Antisense Oligonucleotides: A New Therapeutic Principle", Chemical Reviews (1990) 90 (4):543-584.
UniProtKB B1FZS3; Retrieved from internet on Jul. 25, 2018: https://www.uniprot.org/uniprot/B1FZS3.
Uniprot Assession No. B8J087 (uncharacterized protein), Mar. 3, 2009.
Uniprot Assession No. Q9ZZR8 (Cytochrome b), May 1, 1999.
Venkatesh et al., "Elephant shark genome provides unique insights into gnathostome evolution", Nature (2014) 505(7482):174-179.
Villacres et al., "Cloning, Chromosomal Mapping, and Expression of Human Fetal Brain Type I Adenylyl Cyclase", Genomics (1993) 16(2):473-478.
Vitetta et al., "Redesigning nature's poisons to create anti-tumor reagents", Science (1987) 238(4830): 1098-1104.
Wang W., "Lyophilization and development of solid protein pharmaceuticals", Int. J. Pharm. (2000) 203(1-2):1-60.
Waterhouse et al., "Jalview Version 2—a multiple sequence alignment editor and analysis workbench", Bioinform. (2009) 9:1189-1191.
Zhao et al., "A novel strategy to tag matrix metalloproteinases-positive cells for in vivo imaging of invasive and metastatic activity of tumor cells", J. Control Release (2010) 144(1):109-114.
Zon et al., "Phosphorothioate oligonucleotides: chemistry, purification, analysis, scale-up and future directions", Anticancer Drug Des. (1991) 6(6):539-568.
ADC review, Retrieved on Mar. 17, 2016 from http://adcreview.com/adc-university/adcs-101/cytotoxic-agents/maytansine/ (4 pages).
Baldrick P. "Pharmaceutical excipient development: the need for preclinical guidance." Regul. Toxicol Pharmacol. (2000) 32(2):210-218.
BLAST search of SEQ ID No. 362; Received on Mar. 17, 2016 from http://blast.ncbi.nlm.nih.gov/Blast.cgi (8 pages).
BLAST search of SEQ ID No. 363; Received on Mar. 17, 2016 from http://blast.ncbi.nlm.nih.gov/Blast.cgi (7 pages).
BLAST search of SEQ ID No. 364; Received on Mar. 17, 2016 from http://blast.ncbi.nlm.nih.gov/Blast.cgi (8 pages).
Bowie et al., "A method to identify protein sequences that fold into a known three-dimensional structure", Science (1991) 253(5016):164-170.
Casadaban et al., "Analysis of gene control signals by DNA fusion and cloning in *Escherichia coli*", JMB (1980) 138(2):179-207.
Charman WN, "Lipids, lipophilic drugs, and oral drug delivery-some emerging concepts." J. Pharm. Sci. (2000) 89(8):967-978.
Chothia & Lesk, "Canonical Structures for the Hypervariable Regions of Immunoglobulins", J. Mol. Biol. (1987) 196:901-917.
Chothia et al., "Conformations of immunoglobulin hypervariable regions", Nature (1989) 342:878-883.
Database EMBL, Accession No. AF099373 (Jan. 2, 2014) "Callorhinchus milii (elephant shark) protein ITFG3", Venkatesh et al. [online]; Retrieved from Internet on Jan. 9, 2017 (2 pages): https://www.ebi.ac.uk/ena/browser/api/embl/AF099373.
Davies et al., "Antibody-antigen complexes", Annual Rev. Biochem. (1990) 59:439-473.
"Derivative (chemistry)", Wikipedia, Accessed Sep. 11, 2017 (1 page); Retrieved from: https://en.wikipedia.org/w/ index.php?title=Derivative_(chemistry)&oldid=779855519.

(56) References Cited

OTHER PUBLICATIONS

Donaldson et al., "Design and development of masked therapeutic antibodies to limit off-target effects: application to anti-EGFR antibodies", Cancer Bio. & Therapy (2009) 8(22):2147-2152.
Eppstein et al., "Biological activity of liposome-encapsulated murine interferon gamma is mediated by a cell membrane receptor", Proc. Natl. Acad. Sci. USA, (1985) 82(11):3688-3692.
GenBank Accession No. ADA97619, "Sequence 28102 from U.S. Pat. No. 6,551,795" (Rubenfield et al.), Retrieved from internet on Mar. 17, 2016 (3 pages): http://seqdata.uspto.gov /?pageRequest=viewSequence&DocID=06551795B1&seqID =28102.

* cited by examiner

MATRIX METALLOPROTEASE-CLEAVABLE AND SERINE OR CYSTEINE PROTEASE-CLEAVABLE SUBSTRATES AND METHODS OF USE THEREOF

CROSS-REFERENCE TO RELATED APPLICATIONS

This application is a continuation application of U.S. application Ser. No. 16/705,124 filed Dec. 5, 2019, which claims the benefit of U.S. Provisional Application Nos. 62/776,409, filed Dec. 6, 2018, and 62/778,062, filed Dec. 11, 2018, the contents of which are incorporated herein by reference in their entireties.

SEQUENCE LISTING

The instant application contains a Sequence Listing which has been submitted electronically in XML format and is hereby incorporated by reference in its entirety. Said XML copy, created on Jan. 17, 2024 is named "4862-109US4.xml" and is 315,392 bytes in size.

FIELD OF THE INVENTION

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP) and/or at least one cysteine protease (CP), to activatable antibodies and other larger molecules that include these polypeptides that include at least a CM1 that is a substrate for at least one MMP protease and a CM2 that is a substrate for at least one SP protease and/or at least one CP protease, and to methods of making and using these polypeptides that include at least a CM1 that is a substrate for at least one MMP protease and a CM2 that is a substrate for at least one SP protease and/or at least one CP protease in a variety of therapeutic, diagnostic and prophylactic indications.

BACKGROUND OF THE INVENTION

Proteases are enzymes that degrade proteins by cleaving the peptide bonds between amino acid residues. Proteases occur naturally in all organisms and are involved in a variety of physiological reactions from simple degradation to highly regulated pathways. Some proteases are known to break specific peptide bonds based on the presence of a particular amino acid sequence within a protein.

Accordingly, there exists a need to identify new substrates for proteases and to use these substrates in a variety of therapeutic, diagnostic and prophylactic indications.

SUMMARY OF THE INVENTION

In an aspect of the present invention, provided herein is an isolated polypeptide comprising a tandem substrate, wherein the tandem substrate comprises at least a first cleavable moiety (CM1) that is a substrate for at least one matrix metalloprotease (MMP) and at least a second cleavable moiety (CM2) that is a substrate for at least one serine protease (SP) or cysteine protease (CP), wherein CM1 comprises the amino acid sequence AHGL or PRQV, and wherein the N-terminal to C-terminal arrangement of the tandem substrate is CM1-CM2 or CM2-CM1. In some embodiments, the CM1 of the isolated polypeptide comprises an amino acid sequence that is selected from the group consisting of ALAHGLF (SEQ ID NO: 1), ALAHGL (SEQ ID NO: 52), LAHGLF (SEQ ID NO: 50), LAHGL (SEQ ID NO: 53), and AHGLF (SEQ ID NO: 51). In some embodiments, the CM1 of the isolated polypeptide comprises an amino acid sequence that is selected from the group consisting of HVPRQV (SEQ ID NO: 8) and VPRQV (SEQ ID NO: 60). In some embodiments, the isolated polypeptide of the present disclosure comprises a CM1 and CM2 that are linked via a linking peptide. In some embodiments, the CM1 and CM2 of the isolated polypeptide are directly linked to each other. In some embodiments, the isolated polypeptide of the present disclosure comprises a CM2 that comprises a substrate for a CP enzyme, and wherein the CP enzyme is a legumain. In some embodiments, the isolated polypeptide of the present disclosure comprises a CM2 that comprises a substrate for a SP enzyme selected from the group consisting of a urokinase, a matriptase, and a neutrophil elastase. In some embodiments, the isolated polypeptide of present disclosure includes a CM2 that comprises a substrate for a SP enzyme selected from the group consisting of a urokinase, a matriptase, and a neutrophil elastase and a substrate for a CP enzyme, and wherein the CP enzyme is a legumain. In some embodiments, the isolated polypeptide of the present disclosure comprises a CM1 that comprises a substrate for a MMP enzyme selected from the group consisting of MMP2, MMP9, or MMP14.

In some embodiments, the isolated polypeptide of the present disclosure includes a CM2 that comprises an amino acid sequence selected from the group consisting of SGR, LSGR (SEQ ID NO: 73), ARG, PRS, TFVH (SEQ ID NO: 141), AAN, SAN, and GPTN (SEQ ID NO: 152).

In some embodiments, the isolated polypeptide of the present disclosure includes a CM2 that comprises an amino acid sequence selected from the group consisting of SGR, LSGR (SEQ ID NO: 73), LSGRS (SEQ ID NO: 72), LSGRSD (SEQ ID NO: 71), LSGRSA (SEQ ID NO: 110), LSGRSDN (SEQ ID NO: 70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGRSANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104). In some embodiments, the isolated polypeptide of the present disclosure includes a CM2 that comprises an amino acid sequence selected from the group consisting of ARGP (SEQ ID NO: 128), TARG (SEQ ID NO: 125), and TARGP (SEQ ID NO: 124). In some embodiments, the isolated polypeptide of the present disclosure includes a CM2 that comprises an amino acid sequence selected from the group consisting of APRS (SEQ ID NO: 131), APRSF (SEQ ID NO: 130), and PRSF (SEQ ID NO: 132). In some embodiments, the isolated polypeptide of the present disclosure includes a CM2 that comprises an amino acid sequence selected from the group consisting of GLPTFVHL (SEQ ID NO. 135), GLPTFVH (SEQ ID NO: 136), GLPTFV (SEQ ID NO: 137), LPTFVHL (SEQ ID NO: 138), LPTFVH (SEQ ID NO: 139), and LPTFV (SEQ ID NO: 140). In some embodiments, the isolated polypeptide of the present disclosure includes a CM2 that comprises an amino acid sequence selected from the group consisting of AAN, SAN, and GPTN (SEQ ID NO: 152). In some embodiments, the isolated polypeptide of the present disclosure includes a CM2 that comprises an amino acid sequence selected from the group consisting of AAN, SAN, and GPTN (SEQ ID NO: 152); and an amino acid sequence selected from the group consisting of SGR, LSGR (SEQ ID NO: 73), LSGRS (SEQ ID NO: 72), LSGRSD (SEQ ID NO: 71), LSGRSA (SEQ ID NO: 110), LSGRSDN (SEQ ID NO: 70), LSGRSAN (SEQ ID NO: 109), LSGRSDNH (SEQ ID NO: 20), LSGRSGNH (SEQ ID NO: 78), LSGRSDNP (SEQ ID NO: 90), LSGRSDNI (SEQ ID NO: 84), LSGR-SANI (SEQ ID NO: 108), LSGRSANP (SEQ ID NO: 114), LSGRSDYH (SEQ ID NO: 86), LSGRSDTH (SEQ ID NO: 92), LSGRSDQH (SEQ ID NO: 96), LSGRSDIH (SEQ ID NO: 100), and LSGRSDDH (SEQ ID NO: 104).

In some embodiments, the isolated polypeptide of the present disclosure has the N-terminal to C-terminal arrangement of the tandem substrate is CM1-CM2. In some embodiments, the isolated polypeptide of the present disclosure has the N-terminal to C-terminal arrangement of the tandem substrate is CM2-CM1.

In some embodiments, the isolated polypeptide of the present disclosure has the cleavability of the CM1 first cleavable moiety by MMP9 and MMP14 that are each at least 80%. In some embodiments, the isolated polypeptide of the present disclosure has the cleavability of the CM1 first cleavable moiety by MMP9 and MMP14 that are each at least 85%. In some embodiments, the isolated polypeptide of the present disclosure has the cleavability of the CM1 first cleavable moiety by MMP9 and MMP14 that are each at least 90%.

In some embodiments, the isolated polypeptide of the present disclosure has the in vivo stability of the CM1 first cleavable moiety is less than 30% activation. In some embodiments, the isolated polypeptide of the present disclosure has the in vivo stability of the CM1 first cleavable moiety is less than 25% activation.

In some embodiments, the isolated polypeptide of the present disclosure has the cleavability of the tandem substrate by MMIP9 and MMP14 that are each at least $30^{0}$%. In some embodiments, the isolated polypeptide of the present disclosure has the cleavability of the tandem substrate by MMP9 and MMP14 that are each at least 50%. In some embodiments, the isolated polypeptide of the present disclosure has the cleavability of the tandem substrate by MMP9 and MMP14 that are each at least 70%.

In some embodiments, the isolated polypeptide of the present disclosure has the cleavability of the tandem substrate by MMP9 and MMP14 that are each at least 15% and the cleavability of the tandem substrate by matriptase is at least 30%. In some embodiments, the isolated polypeptide of the present disclosure has the cleavability of the tandem substrate by MMP9 and MMP14 that are each at least 30% and the cleavability of the tandem substrate by matriptase is at least 30%. In some embodiments, the isolated polypeptide of the present disclosure has the cleavability of the tandem substrate by MMP9 and MMP14 that are each at least 50% and the cleavability of the tandem substrate by matriptase is at least 50%. In some embodiments, the isolated polypeptide of the present disclosure has the cleavability of the tandem substrate by MMP9 and MMP14 that are each at least 70% and the cleavability of the tandem substrate by matriptase is at least 70%.

In some embodiments, the isolated polypeptide of the present disclosure has a tandem substrate with the in vivo stability of less than 40% activation. In some embodiments, the isolated polypeptide of the present disclosure has a tandem substrate with the in vivo stability of less than 30% activation. In some embodiments, the isolated polypeptide of the present disclosure has a tandem substrate with the in vivo stability of less than 25% activation. In some embodiments, the isolated polypeptide of the present disclosure has a tandem substrate with the in vivo stability of less than 20% activation.

In some embodiments, the isolated polypeptide of the present disclosure comprises the tandem substrate comprising an amino acid sequence selected from the group consisting of SEQ ID NOs. 25-43. In some embodiments, the isolated polypeptide of the present disclosure comprises the tandem substrate comprising an amino acid sequence selected from the group consisting of SEQ ID NOs: 25, 26, 29, 31, 32, 34, 36, and 37. In some embodiments, the isolated polypeptide of the present disclosure comprises the tandem substrate comprising an amino acid sequence selected from the group consisting of SEQ ID NOs: 27, 28, 30, 33, and 35. In some embodiments, the isolated polypeptide of the present disclosure comprises the tandem substrate comprising an amino acid sequence selected from the group consisting of SEQ ID NOs: 25, 29, 31, 36, and 37. In some embodiments, the isolated polypeptide of the present disclosure comprises the tandem substrate comprising an amino acid sequence selected from the group consisting of SEQ ID NOs: 26, 32, and 34. In some embodiments, the isolated polypeptide of the present disclosure comprises the tandem substrate comprising an amino acid sequence selected from the group consisting of SEQ ID NOs: 27, 28, and 33. In some embodiments, the isolated polypeptide of the present disclosure comprises the tandem substrate comprising an amino acid sequence selected from the group consisting of SEQ ID NOs: 30 and 35.

In some embodiments, provided herein is an isolated polypeptide of the present disclosure that comprises an antibody or antigen binding fragment thereof (AB) that specifically binds a target; at least a first cleavable moiety (CM1) that is a substrate for at least one matrix metalloprotease (MMP); and at least a second cleavable moiety (CM2) that is a substrate for at least one serine protease (SP) or cysteine protease (CP), wherein CM1 comprises the amino acid sequence AHGL or PRQV, and wherein the N-terminal to C-terminal arrangement of the tandem substrate is CM1-CM2 or CM2-CM1. In some embodiments, at least one of the MMP, the CP, and SP are co-localized in a tissue with the target. In some embodiments, the isolated polypeptide of the present disclosure comprises an antigen binding fragment thereof selected from the group consisting of a Fab fragment, a $F(ab')_2$ fragment, a scFv, a scAb, a dAb, a single domain heavy chain antibody, and a single domain light chain antibody. In some embodiments, the isolated polypeptide of the present disclosure comprises an AB that is linked to the CM1. In some embodiments, the isolated polypeptide of the present disclosure comprises an AB that is linked directly to the CM1. In some embodiments, the isolated polypeptide of the present disclosure comprises an AB that is linked to the CM1 via a linking peptide. In some embodiments, the isolated polypeptide of the present disclosure comprises an AB that is linked to the CM2. In some embodiments, the isolated polypeptide of the present disclosure comprises an AB that is linked directly to the CM2. In some embodiments, the isolated polypeptide of the present disclosure comprises an AB that is linked to the CM2 via a linking peptide. In some embodiments, the isolated polypeptide of the present disclosure comprises an AB that comprises a light chain variable region of an antibody or antigen binding fragment thereof, and wherein the CM1 or the CM2 is linked to the N-terminus of the light chain variable region of the AB. In some embodiments, the isolated polypeptide of the present disclosure comprises an AB that comprises a heavy chain variable region of an antibody or antigen binding fragment thereof, and wherein the CM1 or the CM2 is linked to the N-terminus of the heavy chain variable region of the AB.

In some embodiments, the isolated polypeptide of the present disclosure comprises a masking moiety (MM). In some embodiments, the isolated polypeptide of the present disclosure comprises a MM that has a dissociation constant for binding to the AB that is greater than the dissociation constant of the AB for binding to the target. In some embodiments, the isolated polypeptide of the present disclosure comprises a MM that is a polypeptide of no more than 40 amino acids in length. In some embodiments, the isolated polypeptide of the present disclosure comprises a MM that is linked to the CM1 such that the isolated polypeptide in an uncleaved state comprises the structural arrangement from N-terminus to C-terminus as follows: MM-CM1-CM2-AB or AB-CM2-CM1-MM. In some embodiments, the isolated polypeptide of the present disclosure comprises a linking peptide between the MM and the CM1. In some embodiments, the isolated polypeptide of the present disclosure comprises a linking peptide between the CM2 and the AB. In some embodiments, the isolated polypeptide of the present disclosure comprises a linking peptide between the MM and the CM1 and a linking peptide between the CM2 and the AB. In some embodiments, the isolated polypeptide of the present disclosure comprises a MM that is linked to the CM1 such that the isolated polypeptide in an uncleaved state comprises the structural arrangement from N-terminus to C-terminus as follows: MM-CM2-CM1-AB or AB-CM1-CM2-MM. In some embodiments, the isolated polypeptide of the present disclosure comprises a linking peptide between the MM and the CM2. In some embodiments, the isolated polypeptide of the present disclosure comprises a linking peptide between the CM1 and the AB. In some embodiments, the isolated polypeptide of the present disclosure comprises a linking peptide between the MM and the CM2 and a linking peptide between the CM1 and the AB.

In some embodiments, the isolated polypeptide of the present disclosure comprises a first linking peptide (LP1) and a second linking peptide (LP2), and wherein the isolated polypeptide has the structural arrangement from N-terminus to C-terminus as follows in the uncleaved state: MM-LP1-CM1-CM2-LP2-AB, AB-LP2-CM2-CM1-LP1-MM, MM-LP1-CM2-CM1-LP2-AB, or AB-LP2-CM1-CM2-LP1-MM. In some embodiments, the two linking peptides are not identical to each other. In some embodiments, each of LP1 and LP2 is a peptide of about 1 to 20 amino acids in length. In some embodiments, the isolated polypeptide comprises a third linking peptide (LP') between CM1 and CM2. In some embodiments, the isolated polypeptide of the present disclosure comprises an AB that comprises a light chain variable region of an antibody or antigen binding fragment thereof, and wherein the LP2 is linked to the N-terminus of the light chain variable region of the AB. In some embodiments, the isolated polypeptide of the present disclosure comprises an AB that comprises a heavy chain variable region of an antibody or antigen binding fragment thereof, and wherein the LP2 is linked to the N-terminus of the heavy chain variable region of the AB.

In some embodiments, the isolated polypeptide of the present disclosure comprises a MM wherein the amino acid sequence of the MM is different from that of the target and is no more than 10% identical to the amino acid sequence of a natural binding partner of the AB. In some embodiments, the isolated polypeptide of the present disclosure comprises a MM that does not interfere or compete with the AB for binding to the target in a cleaved state.

In some embodiments, the isolated polypeptide comprises a light chain amino acid sequence that is selected from the group consisting of SEQ ID NOs: 450-462. In some embodiments, the isolated polypeptide comprises a light chain amino acid sequence that is selected from the group consisting of SEQ ID NOs: 450-462, and a heavy chain amino acid sequence comprising SEQ ID NO: 400.

In another aspect of the present invention, provided herein is an activatable antibody that, in an activated state, specifically binds to a target, comprising an antibody or an antigen binding fragment thereof (AB) that specifically binds to the target, a masking moiety (MM) coupled to the AB, wherein the MM inhibits the binding of the AB to the target when the activatable antibody is in an uncleaved state; and a cleavable moiety (CM) comprising a tandem substrate according to any one of the tandem substrates provided herein. In some embodiments, the activatable antibody includes an MM that has a dissociation constant for binding to the AB that is greater than the dissociation constant of the AB for binding to the target. In some embodiments, the activatable antibody includes an MM that is a polypeptide of no more than 40 amino acids in length. In some embodiments, the activatable antibody includes an antigen binding fragment thereof that is selected from the group consisting of a Fab fragment, a $F(ab')_2$ fragment, a scFv, a scAb, a dAb, a single domain heavy chain antibody, and a single domain light chain antibody. In some embodiments, the activatable antibody includes an MM that has a dissociation constant for binding to the AB that is greater than the dissociation constant of the AB for binding to the target.

In some embodiments, the activatable antibody includes a MM that is linked to the CM1 such that the activatable antibody in an uncleaved state comprises the structural arrangement from N-terminus to C-terminus as follows: MM-CM1-CM2-AB or AB-CM2-CM1-MM. In some embodiments, the activatable antibody comprises a linking peptide between the MM and the CM1. In some embodiments, the activatable antibody comprises a linking peptide between the CM2 and the AB. In some embodiments, the activatable antibody comprises a linking peptide between the MM and the CM1 and a linking peptide between the CM2 and the AB.

In some embodiments, the activatable antibody includes a MM that is linked to the CM1 such that the activatable antibody in an uncleaved state comprises the structural arrangement from N-terminus to C-terminus as follows: MM-CM2-CM1-AB or AB-CM1-CM2-MM. In some embodiments, the activatable antibody comprises a linking peptide between the MM and the CM2. In some embodiments, the activatable antibody comprises a linking peptide between the CM1 and the AB. In some embodiments, the activatable antibody comprises a linking peptide between the MM and the CM2 and a linking peptide between the CM1 and the AB.

In some embodiments, the activatable antibody comprises an AB that comprises a light chain variable region of an antibody or antigen binding fragment thereof, and wherein the CM1 or the CM2 is linked to the N-terminus of the light chain variable region of the AB. In some embodiments, the activatable antibody comprises an AB that comprises a heavy chain variable region of an antibody or antigen binding fragment thereof, and wherein the CM1 or the CM2 is linked to the N-terminus of heavy light chain variable region of the AB.

In some embodiments, the activatable antibody comprises a first linking peptide (LP1) and a second linking peptide (LP2), and wherein the activatable antibody has the structural arrangement from N-terminus to C-terminus as follows in the uncleaved state: MM-LP1-CM1-CM2-LP2-AB, AB-LP2-CM2-CM1-LP1-MM, MM-LP1-CM2-CM1-LP2-AB, or AB-LP2-CM1-CM2-LP1-MM. In some embodiments, the two linking peptides are not identical to each other. In some embodiments, each of LP1 and LP2 is a peptide of about 1 to 20 amino acids in length. In some embodiments, the activatable antibody comprises a third linking peptide (LP') between CM1 and CM2. In some embodiments, the activatable antibody comprises an AB that comprises a light chain variable region of an antibody or antigen binding fragment thereof, and wherein the LP2 is linked to the N-terminus of the light chain variable region of the AB. In some embodiments, the activatable antibody comprises an AB that comprises a heavy chain variable region of an antibody or antigen binding fragment thereof, and wherein the LP2 is linked to the N-terminus of the heavy chain variable region of the AB.

In some embodiments, the activatable antibody comprises a light chain amino acid sequence that is selected from the group consisting of SEQ ID NOs: 450-462. In some embodiments, the activatable antibody comprises a light chain amino acid sequence that is selected from the group consisting of SEQ ID NOs: 450-462, and a heavy chain amino acid sequence comprising SEQ ID NO: 400.

In some embodiments, the activatable antibody comprises a MM that is different from that of the target and is no more than 10% identical to the amino acid sequence of a natural binding partner of the AB. In some embodiments, the activatable antibody comprises a MM that does not interfere or compete with the AB for binding to the target in a cleaved state.

In another aspect of the present invention, provided herein is a conjugated activatable antibody comprising the activatable antibody conjugated to an agent. In some embodiments, the agent is conjugated to the AB via a linker. In some embodiments, the agent is conjugated to the AB via a cleavable linker. In some embodiments, the agent is conjugated to the AB via a non-cleavable linker.

In some embodiments, the conjugated activatable antibody comprises an agent that is a toxin or fragment thereof. In some embodiments, the conjugated activatable antibody comprises an agent that is a microtubule inhibitor. In some embodiments, the conjugated activatable antibody comprises an agent that is a nucleic acid damaging agent. In some embodiments, the conjugated activatable antibody comprises an agent that is a dolastatin or a derivative thereof, an auristatin or a derivative thereof, a maytansinoid or a derivative thereof, a duocarmycin or a derivative thereof, a calicheamicin or a derivative thereof, auristatin E or a derivative thereof, monomethyl auristatin E (MMAE), monomethyl auristatin D (MMAD), or a maytansinoid selected from the group consisting of DM1 and DM4. In some embodiments, the conjugated activatable antibody comprises an agent that is a detectable moiety or a diagnostic agent.

In another aspect of the present invention, provided herein is a pharmaceutical composition comprising an isolated polypeptide of the present disclosure or an activatable antibody of the present disclosure or a conjugated activatable antibody of the present disclosure; and a carrier. In some embodiments, the pharmaceutical composition comprises an additional agent. In some embodiments, the pharmaceutical composition comprises an additional agent, which is a therapeutic agent.

In another aspect of the present invention, provided herein is an isolated nucleic acid molecule encoding the isolated polypeptide of the present disclosure or the activatable antibody of the present disclosure. In some embodiments, a vector comprises the isolated nucleic acid molecule of present disclosure.

In another aspect of the present invention, provided herein is a method of producing an antibody or an activatable antibody by culturing a cell under conditions that lead to expression of the isolated polypeptide of the present disclosure or the activatable antibody of the present disclosure. In another aspect of the present invention, provided herein is a method of manufacturing an activatable antibody that, in an activated state, binds a target, the method comprising: culturing a cell comprising a nucleic acid construct that encodes the activatable antibody of the present disclosure and recovering the activatable antibody.

In another aspect of the present invention, provided herein is a method of treating, alleviating a symptom of, or delaying the progression of a disorder or disease comprising administering to a subject in need thereof a therapeutically effective amount of the isolated polypeptide of the present disclosure or the activatable antibody of the present disclosure or the conjugated activatable antibody of the present disclosure or the pharmaceutical composition of the present disclosure. In some embodiments, the disorder or disease is cancer. In some embodiments, the method comprises administering to the subject an additional agent. In some embodiments, the method comprises administering to the subject an additional therapeutic agent.

DETAILED DESCRIPTION OF THE INVENTION

Figure 1:
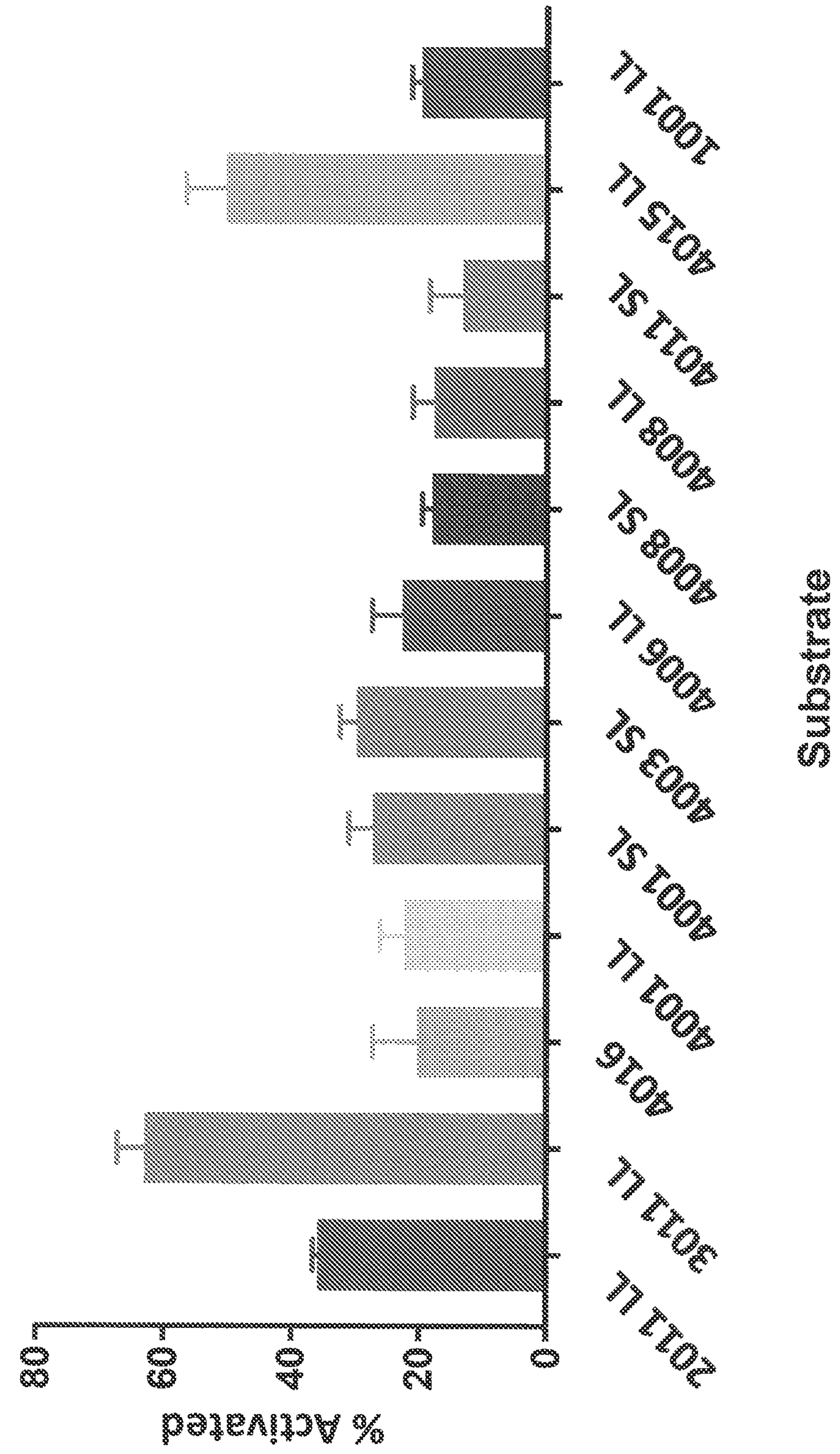
FIG. 1 is a graph showing exemplary results of the percent of the indicated activatable anti-EGFR antibodies of the present disclosure that were observed to be cleaved in vivo following their administration to nu/nu mice. These exemplary results showed that several of the tested activatable antibodies showed a higher degree of stability than other substrates that are cleavable by multiple enzymes.

The present disclosure provides amino acid sequences that include at least a first cleavable moiety (CM1) that is a substrate for at least one matrix metalloprotease (MMP) and at least a second cleavable moiety (CM2) that is a substrate for at least one serine protease (SP) and/or at least one cysteine protease (CP). These amino acid sequences are collectively referred to herein as "tandem substrates." This term is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP) and/or at least one cysteine protease (CP). Thus, the term "tandem substrates" encompasses CM1-CM2 substrates having the structural arrangement from N-terminus to C-terminus as follows: CM1-CM2 or CM2-CM1. The term "tandem substrates" also encompasses substrates where at least a portion of the CM1 sequence overlaps with at least a portion of the CM2 sequence.

In some embodiments, CM2 includes at least two substrates. In some embodiments, CM2 includes a substrate for a first serine protease and a substrate for a second serine protease. In some embodiments, CM2 includes a substrate for a serine protease and a substrate for a cysteine protease.

The CM1-CM2 substrates described herein are useful in a variety of therapeutic, diagnostic and prophylactic indications. For example, these CM1-CM2 substrates are useful in activatable antibodies that include antibodies or antigen-binding fragments thereof (AB) that includes a prodomain. The prodomain includes at least one masking moiety (MM) linked to at least one antigen- or epitope-binding domain of the AB such that coupling of the MM reduces the ability of the AB to bind its target.

In some embodiments, the activatable antibody includes at least a first CM (CM1) and a second CM (CM2). In some embodiments, at least a portion of the CM1 substrate sequence overlaps with at least a portion of the CM2 sequence. In some embodiments, the CM1 substrate sequence and the CM2 substrate sequence share at least one amino acid residue in common. In some embodiments, the CM1 substrate sequence and the CM2 substrate sequence share at least two amino acid residues in common. In some embodiments, the CM1 substrate sequence and the CM2 substrate sequence share at least three amino acid residues in common. In some embodiments, the CM1 substrate sequence and the CM2 substrate sequence share three or more amino acid residues in common.

In some embodiments, CM1 and CM2 are separate polypeptides that are operably linked together.

In some embodiments, CM1 and CM2 are separate polypeptides that are directly linked together, i.e., the N-terminus of one substrate is linked directly to the C-terminus of the other substrate polypeptide. In some embodiments, the N-terminus of the CM1 is linked directly to the C-terminus of the CM2. In some embodiments, the N-terminus of the CM2 is linked directly to the C-terminus of the CM1.

In some embodiments, CM1 and CM2 are separate polypeptides that are operably linked together via at least one linking moiety.

In some embodiments, the first cleavable moiety CM1 and the second cleavable moiety CM2 in the activatable antibody in the uncleaved state have the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody includes a linking peptide (LP') between CM1 and CM2. In some embodiments, the activatable antibody includes a linking peptide (LP'') between the masking moiety (MM) and CM1. In some embodiments, the activatable antibody includes a linking peptide (LP''') between CM2 and AB. In some embodiments, the activatable antibody includes a linking peptide (LP'') between the MM and CM1 and a linking peptide (LP''') between CM2 and AB. In some embodiments, the activatable antibody includes a linking peptide between the MM and CM1 (LP'') and a linking peptide between CM1 and CM2 (LP'). In some embodiments, the activatable antibody includes a linking peptide (LP') between CM1 and CM2 and a linking peptide (LP''') between CM2 and AB. In some embodiments, the activatable antibody includes a linking peptide (LP'') between the MM and CM1, a linking peptide (LP') between CM1 and CM2, and a linking peptide (LP''') between CM2 and AB.

In some embodiments, the activatable antibody includes a linking peptide (LP') between CM1 and CM2. In some embodiments, the activatable antibody includes a linking peptide (LP'') between the AB and CM1. In some embodiments, the activatable antibody includes a linking peptide (LP''') between CM2 and the masking moiety (MM). In some embodiments, the activatable antibody includes a linking peptide (LP'') between the AB and CM1 and a linking peptide (LP''') between CM2 and MM. In some embodiments, the activatable antibody includes a linking peptide between the AB and CM1 (LP'') and a linking peptide between CM1 and CM2 (LP'). In some embodiments, the activatable antibody includes a linking peptide (LP') between CM1 and CM2 and a linking peptide (LP''') between CM2 and MM. In some embodiments, the activatable antibody includes a linking peptide (LP'') between the AB and CM1, a linking peptide (LP') between CM1 and CM2, and a linking peptide (LP''') between CM2 and MM.

In some embodiments, LP' is GG. In some embodiments, LP' is GGSGGS (SEQ ID NO. 218).

In some embodiments, CM1 is a substrate for at least one matrix metalloprotease (MMP). Examples of MMPs include MMP1; MMP2; MMP3; MMP7; MMP8; MMP9; MMP10, MMP11; MMP12; MMP13; MMP14; MMP15; MMP16; MMP17; MMP19; MMP20; MMP23; MMP24; MMP26, and MMP27.

In some embodiments, CM1 is a substrate for MMP2, MMP9, MMP14, MMP1, MMP3, MMP13, MMP17, MMP11, and/or MMP19. In some embodiments, CM1 is a substrate for MMP2. In some embodiments, CM1 is a substrate for MMP9. In some embodiments, CM1 is a substrate for MMP14. In some embodiments, CM1 is a substrate for two or more MMPs. In some embodiments, CM1 is a substrate for at least MMP9 and MMP14. In some embodiments, CM1 is a substrate for at least MMP2 and MMP9. In some embodiments, CM1 is a substrate for at least MMP2 and MMP14. In some embodiments, CM1 is a substrate for three or more MMPs. In some embodiments, CM1 is a substrate for at least MMP2, MMP9, and MMP14. In some embodiments, the CM1 comprises two or more substrates for the same MMP. In some embodiments, the CM1 comprises at least two or more MMP2 substrates. In some embodiments, the CM1 comprises at least two or more MMP9 substrates. In some embodiments, the CM1 comprises at least two or more MMP14 substrates.

In some embodiments, CM1 is a substrate for an MMP and includes at least the sequence ALAHGLF (SEQ ID NO: 1); DLAHPLL (SEQ ID NO: 2); AFRHLR (SEQ ID NO: 3); PHGFFQ (SEQ ID NO: 4); SVHHLI (SEQ ID NO: 5); RGPKLYW (SEQ ID NO: 6), RFPYGVW (SEQ ID NO: 7); HVPRQV (SEQ ID NO: 8); SNPFKY (SEQ ID NO: 9); RFPLKV (SEQ ID NO: 10); PFHLSR (SEQ ID NO: 11), STVFHM (SEQ ID NO: 12); MGPWFM (SEQ ID NO: 13); RHLAKL (SEQ ID NO: 14); PLGVRGK (SEQ ID NO: 15), and QNQALRIA (SEQ ID NO: 16).

In some embodiments, the CM1 comprises the amino acid sequence ALAHGLF (SEQ ID NO: 1). In some embodiments, the CM1 comprises the amino acid sequence DLAHPLL (SEQ ID NO: 2). In some embodiments, the CM1 comprises the amino acid sequence AFRHLR (SEQ ID NO: 3). In some embodiments, the CM1 comprises the amino acid sequence PHGFFQ (SEQ ID NO: 4). In some embodiments, the CM1 comprises the amino acid sequence SVHHLI (SEQ ID NO: 5). In some embodiments, the CM1 comprises the amino acid sequence RGPKLYW (SEQ ID NO: 6). In some embodiments, the CM1 comprises the amino acid sequence RFPYGVW (SEQ ID NO: 7). In some embodiments, the CM1 comprises the amino acid sequence HVPRQV (SEQ ID NO: 8). In some embodiments, the CM1 comprises the amino acid sequence SNPFKY (SEQ ID NO: 9). In some embodiments, the CM1 comprises the amino acid sequence RFPLKV (SEQ ID NO: 10). In some embodiments, the CM1 comprises the amino acid sequence PFHLSR (SEQ ID NO: 11). In some embodiments, the CM1 comprises the amino acid sequence STVFHM (SEQ ID NO: 12). In some embodiments, the CM1 comprises the amino acid sequence MGPWFM (SEQ ID NO: 13). In some embodiments, the CM1 comprises the amino acid sequence RHLAKL (SEQ ID NO: 14). In some embodiments, the CM1 comprises the amino acid sequence PLGVRGK (SEQ ID NO: 15). In some embodiments, the CM1 comprises the amino acid sequence QNQALRIA (SEQ ID NO: 16).

In some embodiments, CM1 comprises the amino acid sequence LAHGLF (SEQ ID NO: 50). In some embodiments, CM1 comprises the amino acid sequence AHGLF (SEQ ID NO: 51). In some embodiments, CM1 comprises the amino acid sequence ALAHGL (SEQ ID NO: 52). In some embodiments, CM1 comprises the amino acid sequence LAHGL (SEQ ID NO: 53). In some embodiments, CM1 comprises the amino acid sequence AHGL (SEQ ID NO: 54). In some embodiments, CM1 comprises the amino acid sequence ALAHG (SEQ ID NO: 55). In some embodiments, CM1 comprises the amino acid sequence LAHG (SEQ ID NO: 56). In some embodiments, CM1 comprises the amino acid sequence AHG.

In some embodiments, CM1 comprises the amino acid sequence VPRQV (SEQ ID NO: 60). In some embodiments, CM1 comprises the amino acid sequence PRQV (SEQ ID NO: 61). In some embodiments, CM1 comprises the amino acid sequence HVPRQ (SEQ ID NO: 62). In some embodiments, CM1 comprises the amino acid sequence VPRQ (SEQ ID NO: 63). In some embodiments, CM1 comprises the amino acid sequence PRQ.

In some embodiments, CM2 is a substrate for at least one serine protease (SP). In some embodiments, the SP is selected from u-type plasminogen activator (uPA, also referred to as urokinase), matriptase (also referred to herein as MT-SP1 or MTSP1), neutrophil elastase (e.g., human neutrophil elastase), and combinations thereof. Examples of other SP that cleave a CM2 described herein include, by way of non-limiting example, activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Lactoferrin; Marapsin; NS3/4A; PACE4; Plasmin; PSA; tPA; Thrombin; Tryptase; a Type H Transmembrane Serine Protease (TTSP) such as, e.g., DESC1, DPP-4, FAP, Hepsin, Matriptase-2, TMPRSS2, TMPRSS3, and/or TMPRSS4.

For example, suitable CM2 are cleaved by at least one serine protease and may include at least one sequence selected from the following amino acid sequences: LSGRSDNH (SEQ ID NO: 20), LSGRSDN (SEQ ID NO: 70), LSGRSD (SEQ ID NO: 71), LSGRS (SEQ ID NO: 72), LSGR (SEQ ID NO: 73), SGRSDN (SEQ ID NO: 74), SGRSD (SEQ ID NO: 75), SGRS (SEQ ID NO: 76), SGR, LSGRSGNH (SEQ ID NO: 78), LSGRSGN (SEQ ID NO: 79), LSGRSG (SEQ ID NO: 80), SGRSGNH (SEQ ID NO: 81), SGRSGN (SEQ ID NO: 82), SGRSG (SEQ ID NO: 83), LSGRSDNI (SEQ ID NO: 84), SGRSDNI (SEQ ID NO: 85), LSGRSDYH (SEQ ID NO: 86), LSGRSDY (SEQ ID NO: 87), SGRSDYH (SEQ ID NO: 88), SGRSDY (SEQ ID NO: 89), LSGRSDNP (SEQ ID NO: 90), SGRSDNP (SEQ ID NO: 91), LSGRSDTH (SEQ ID NO: 92), LSGRSDT (SEQ ID NO: 93), SGRSDTH (SEQ ID NO: 94), SGRSDT (SEQ ID NO: 95), LSGRSDQH (SEQ ID NO: 96), LSGRSDQ (SEQ ID NO: 97), SGRSDQH (SEQ ID NO: 98), SGRSDQ (SEQ ID NO: 99), LSGRSDIH (SEQ ID NO: 100), LSGRSDI (SEQ ID NO: 101), SGRSDIH (SEQ ID NO: 102), SGRSDI (SEQ ID NO: 103), LSGRSDDH (SEQ ID NO: 104), LSGRSDD (SEQ ID NO: 105), SGRSDDH (SEQ ID NO: 106), SGRSDD (SEQ ID NO: 107), LSGRSANI (SEQ ID NO: 108), LSGRSAN (SEQ ID NO: 109), LSGRSA (SEQ ID NO: 110), SGRSANI (SEQ ID NO: 111), SGRSAN (SEQ ID NO: 112), SGRSA (SEQ ID NO: 113), LSGRSANP (SEQ ID NO: 114), and SGRSANP (SEQ ID NO: 115).

In some embodiments, suitable CM2 are cleaved by at least one serine protease and may include at least one sequence selected from the following amino acid sequences: TARGPSFK (SEQ ID NO: 120), ARGPSFK (SEQ ID NO: 121), TARGPSF (SEQ ID NO: 122), TARGPS (SEQ ID NO: 123), TARGP (SEQ ID NO: 124), TARG (SEQ ID NO: 125), ARGPSF (SEQ ID NO: 126), ARGPS (SEQ ID NO: 127), ARGP (SEQ ID NO: 128), and ARG.

In some embodiments, suitable CM2 are cleaved by at least one serine protease and may include at least one sequence selected from the following amino acid sequences: APRSF (SEQ ID NO: 130), APRS (SEQ ID NO: 131), and PRSF (SEQ ID NO: 132).

In some embodiments, suitable CM2 are cleaved by at least one serine protease and may include at least one sequence selected from the following amino acid sequences: GLPTFVHL (SEQ ID NO: 135), GLPTFVH (SEQ ID NO: 136), GLPTFV (SEQ ID NO: 137), LPTFVHL (SEQ ID NO: 138), LPTFVH (SEQ ID NO: 139), and LPTFV (SEQ ID NO: 140).

In some embodiments, CM2 is a substrate for at least one cysteine protease (CP). In some embodiments, the CP is a legumain. In some embodiments, suitable CM2 are cleaved by at least one cysteine protease and may include at least one sequence selected from the following amino acid sequences: AAN, SAN, and GPTN (SEQ ID NO: 152).

In some embodiments, the CM1-CM2 substrate comprises an amino acid sequence selected from the group consisting of: LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO. 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), AVGLLAPPGGLSGRSNI (SEQ ID NO: 39), ISSGLLSGRSNIGS (SEQ ID NO: 40), AVGLLAPPGGLSGRSNIGS (SEQ ID NO: 41), ISSGLLSGRSNIG (SEQ ID NO: 42), and AVGLLAPPGGLSGRSNIG (SEQ ID NO: 43).

In some embodiments, the activatable antibody in the uncleaved state has the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody comprises a first linking peptide (LP1) and a second linking peptide (LP2), and the antibody in the uncleaved state has the structural arrangement from N-terminus to C-terminus as follows: MM1-LP1-CM1-CM2-LP2-AB, AB-LP2-CM2-CM1-LP1-MM, MM1-LP1-CM2-CM1-LP2-AB, or AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody includes a linking peptide (LP') between CM1 and CM2. In some embodiments, the activatable antibody includes a linking peptide (LP1) between the masking moiety (MM) and CM1. In some embodiments, the activatable antibody includes a linking peptide (LP2) between CM2 and AB. In some embodiments, the activatable antibody includes a linking peptide (LP1) between the MM and CM1 and a linking peptide (LP2) between CM2 and AB. In some embodiments, the activatable antibody includes a linking peptide between the MM and CM1 (LP1) and a linking peptide between CM1 and CM2 (LP'). In some embodiments, the activatable antibody includes a linking peptide (LP') between CM1 and CM2 and a linking peptide (LP2) between CM2 and AB. In some embodiments, the activatable antibody includes a linking peptide (LP1) between the MM and CM1, a linking peptide (LP') between CM1 and CM2, and a linking peptide (LP2) between CM2 and AB.

In some embodiments, the activatable antibody includes a linking peptide (LP') between CM1 and CM2. In some embodiments, the activatable antibody includes a linking peptide (LP1) between the AB and CM1. In some embodiments, the activatable antibody includes a linking peptide (LP2) between CM2 and the masking moiety (MM). In some embodiments, the activatable antibody includes a linking peptide (LP1) between the AB and CM1 and a linking peptide (LP2) between CM2 and MM. In some embodiments, the activatable antibody includes a linking peptide between the AB and CM1 (LP1) and a linking peptide between CM1 and CM2 (LP'). In some embodiments, the activatable antibody includes a linking peptide (LP') between CM1 and CM2 and a linking peptide (LP2) between CM2 and MM. In some embodiments, the activatable antibody includes a linking peptide (LP1) between the AB and CM1, a linking peptide (LP') between CM1 and CM2, and a linking peptide (LP2) between CM2 and MM.

In some embodiments, LP' is GG. In some embodiments, LP' is GGSGGS (SEQ ID NO: 218).

In some embodiments, at least one of LP1 or LP2 comprises an amino acid sequence selected from the group consisting of $(GS)_n$, $(GGS)_n$, $(GSGGS)_n$(SEQ ID NO: 200) and $(GGGS)_n$ (SEQ ID NO: 201), where n is an integer of at least one.

In some embodiments, at least one of LP1 or LP2 comprises an amino acid sequence selected from the group consisting of GGSG (SEQ ID NO: 202), GGSGG (SEQ ID NO: 203), GSGSG (SEQ ID NO: 204), GSGGG (SEQ ID NO: 205), GGGSG (SEQ ID NO: 206), and GSSSG (SEQ ID NO: 207).

In some embodiments, LP1 comprises the amino acid sequence GSSGGSGGSGGSG (SEQ ID NO: 208), GSSGGSGGSGG (SEQ ID NO: 209), GSSGGSGGSGGS (SEQ ID NO: 210), GSSGGSGGSGGSGGGS (SEQ ID NO: 211), GSSGGSGGSG (SEQ ID NO: 212), or GSSGGSGGSGS (SEQ ID NO: 213), GGGSSGGS (SEQ ID NO: 214), and GSSGGSGGSGGSG (SEQ ID NO: 215).

In some embodiments, LP2 comprises the amino acid sequence GSS, GGS, GGGS (SEQ ID NO: 216), GSSGT (SEQ ID NO: 217) or GSSG (SEQ ID NO: 218). In some embodiments, LP2 comprises the amino acid sequence GGS. In some embodiments, LP2 comprises the amino acid sequence GGGS (SEQ ID NO: 216).

In some embodiments, CM1 is a substrate for an MMP and includes at least the sequence ALAHGLF (SEQ ID NO: 1); DLAHPLL (SEQ ID NO: 2); AFRHLR (SEQ ID NO: 3); PHGFFQ (SEQ ID NO: 4); SVHHLI (SEQ ID NO: 5); RGPKLYW (SEQ ID NO: 6), RFPYGVW (SEQ ID NO: 7), HVPRQV (SEQ ID NO: 8); SNPFKY (SEQ ID NO: 9); RFPLKV (SEQ ID NO: 10); PFHLSR (SEQ ID NO: 11); STVFHM (SEQ ID NO: 12); MGPWFM (SEQ ID NO: 13), RHLAKL (SEQ ID NO: 14); PLGVRGK (SEQ ID NO: 15); and QNQALRIA (SEQ ID NO: 16).

In some embodiments, an isolated polypeptide of the present disclosure or an activatable antibody of the present disclosure comprises an CM1-CM2 substrate and an LP2 linker, wherein the CM1-CM2 comprises an amino acid sequence selected from the group consisting of: LSGRSALAHGLF (SEQ ID NO: 25), ALAHGLFSGRSAN (SEQ ID NO. 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO: 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), and AVGLLAPPGGLSGRSNI (SEQ ID NO: 39), and the LP2 linker comprises GGGS (SEQ ID NO: 216).

In some embodiments, an isolated polypeptide of the present disclosure or an activatable antibody of the present disclosure comprises an CM1-CM2 substrate and an LP2 linker, wherein the CM1-CM2 comprises an amino acid sequence selected from the group consisting of: LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), TARGPVPRQV (SEQ ID NO: 30), APRSALAHGLF (SEQ ID NO: 31), ALAHGLFAPRSF (SEQ ID NO: 32), HVPRQVAPRSF (SEQ ID NO: 33), ALAHGLPTFVHL (SEQ ID NO: 34), GLPTFVHLPRQV (SEQ ID NO: 35), AANALAHGLF (SEQ ID NO: 36), GPTNALAHGLF (SEQ ID NO: 37), ISSGLLSGRSNI (SEQ ID NO: 38), and AVGLLAPPGGLSGRSNI (SEQ ID NO: 39), and the LP2 linker comprises GGS.

In some embodiments, an isolated polypeptide of the present disclosure or an activatable antibody of the present disclosure comprises an CM1-CM2 substrate and an LP2 linker, wherein the CM1-CM2 and LP2 comprises an amino acid sequence selected from the group consisting of: LSGRSALAHGLFGGGS (SEQ ID NO: 226), ALAHGLFSGRSANGGGS (SEQ ID NO: 227), HVPRQVLSGRSGGGS (SEQ ID NO: 228), HVPRQVLSGRSANGGGS (SEQ ID NO: 229), TARGPALAHGLFGGGS (SEQ ID NO: 230), TARGPVPRQVGGGS (SEQ ID NO: 231), APRSALAHGLFGGGS (SEQ ID NO: 232), ALAHGLFAPRSFGGGS (SEQ ID NO: 233), HVPRQVAPRSFGGGS (SEQ ID NO: 234), ALAHGLPTFVHLGGGS (SEQ ID NO: 235), GLPTFVHLPRQVGGGS (SEQ ID NO: 236), AANALAHGLFGGGS (SEQ ID NO: 237), GPTNALAHGLFGGGS (SEQ ID NO: 238), ISSGLLSGRSNIGGGS (SEQ ID NO: 239), and AVGLLAPPGGLSGRSNIGGGS (SEQ ID NO: 240).

In some embodiments, an isolated polypeptide of the present disclosure or an activatable antibody of the present disclosure comprises an CM1-CM2 substrate and an LP2 linker, wherein the CM1-CM2 and LP2 comprises an amino acid sequence selected from the group consisting of: LSGRSALAHGLFGGS (SEQ ID NO: 241), ALAHGLFSGRSANGGS (SEQ ID NO: 242), HVPRQVLSGRSGGS (SEQ ID NO: 243), HVPRQVLSGRSANGGS (SEQ ID NO: 244), TARGPALAHGLFGGS (SEQ ID NO: 245), TARGPVPRQVGGS (SEQ ID NO: 246), APRSALAHGLFGGS (SEQ ID NO: 247), ALAHGLFAPRSFGGS (SEQ ID NO: 248), HVPRQVAPRSFGGS (SEQ ID NO: 249), ALAHGLPTFVHLGGS (SEQ ID NO: 250), GLPTFVHLPRQVGGS (SEQ ID NO: 251), AANALAHGLFGGS (SEQ ID NO: 252), GPTNALAHGLFGGS (SEQ ID NO: 253), ISSGLLSGRSNIGGS (SEQ ID NO: 254), and AVGLLAPPGGLSGRSNIGGS (SEQ ID NO: 255).

In some embodiments, the AB has a dissociation constant of about 100 nM or less for binding to the target.

In some embodiments, the activatable antibody includes an antibody or antigen-binding fragment (AB) thereof that specifically binds a target. In some embodiments, the AB is a full-length antibody. In some embodiments, the AB is an immunologically active fragment. In some embodiments, the AB is an antigen-binding fragment. In some embodiments, the AB is a monoclonal antibody, domain antibody, single chain, Fab fragment, a F(ab')2 fragment, a scFv, a scab, a dAb, a single domain heavy chain antibody, or a single domain light chain antibody. In some embodiments, such an AB is a mouse, other rodent, chimeric, humanized or fully human monoclonal antibody.

In some embodiments, the MMP protease is co-localized with the target in a tissue, and the MMP protease cleaves the CM1 in the antibody when the antibody is exposed to the protease. In some embodiments, the SP protease is co-localized with the target in a tissue, and the SP protease cleaves the CM2 substrate in the antibody when the antibody is exposed to the protease. In some embodiments, the CP protease is co-localized with the target in a tissue, and the CP protease cleaves the CM2 substrate in the antibody when the antibody is exposed to the protease. In some embodiments, the MMP protease and/or the SP protease are co-localized with the target in a tissue, and the MMP protease and/or the SP protease cleave the CM1-CM2 substrate in the antibody when the antibody is exposed to the protease. In some embodiments, the MMP protease and the SP protease are co-localized with the target in a tissue, and at least one of the MMP protease and the SP protease cleave the CM1-CM2 substrate in the antibody when the antibody is exposed to the protease. In some embodiments, the MMP protease and/or the CP protease are co-localized with the target in a tissue, and the MMP protease and/or the CP protease cleave the CM1-CM2 substrate in the antibody when the antibody is exposed to the protease. In some embodiments, the MMP protease and the CP protease are co-localized with the target in a tissue, and at least one of the MMP protease and the CP protease cleave the CM1-CM2 substrate in the antibody when the antibody is exposed to the protease. In some embodiments, the MMP protease and/or the CP protease and/or the SP protease are co-localized with the target in a tissue, and the MMP protease and/or the CP protease and/or the SP protease cleave the CM1-CM2 substrate in the antibody when the antibody is exposed to the protease. In some embodiments, the MMP protease and the CP protease and the SP protease are co-localized with the target in a tissue, and at least one of the MMP protease, the SP protease, and the CP protease cleave the CM1-CM2 substrate in the antibody when the antibody is exposed to the protease.

In some embodiments, each of the CM1 substrate sequence and the CM2 substrate sequence of the CM1-CM2 substrate is independently a polypeptide of up to 15 amino acids in length.

In some embodiments, the CM1 substrate sequence of the CM1-CM2 substrate is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is not substantially identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is not substantially identical to any human polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is no more than 90% or more identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any human polypeptide sequence that is naturally cleaved by the same MMP protease.

In some embodiments, the CM2 substrate sequence of the CM1-CM2 substrate is a substrate for at least one SP and/or one CP and comprises a polypeptide sequence that is not substantially identical to any polypeptide sequence, e.g., any animal polypeptide sequence, that is naturally cleaved by the same SP protease. In some embodiments, the CM2 substrate sequence of the CM1-CM2 substrate is a substrate for at least one SP and/or one CP and comprises a polypeptide sequence that is not substantially identical to any mammalian polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is not substantially identical to any human polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any polypeptide sequence, e.g., any animal polypeptide sequence, that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any mammalian polypeptide sequence that is naturally cleaved by the same SP and/or CP protease. In some embodiments, the CM2 substrate sequence of the CM1-CM2 substrate is a substrate for at least one SP and/or one CP and comprises a polypeptide sequence that is no more than 90% or more identical to any human polypeptide sequence that is naturally cleaved by the same SP and/or CP protease.

In some embodiments, the CM1-CM2 substrate of the present disclosure comprises an amino acid sequence selected from the group consisting of SEQ ID NOs. 25-43. In some embodiments, the CM1-CM2 substrate of the present disclosure comprises an amino acid sequence selected from the group consisting of SEQ ID NOs: 25, 26, 29, 31, 32, 34, 36, and 37.

In some embodiments, the CM1-CM2 substrate of the present disclosure comprises an amino acid sequence selected from the group consisting of SEQ ID NOs: 27, 28, 30, 33, and 35. In some embodiments, the CM1-CM2 substrate of the present disclosure comprises an amino acid sequence selected from the group consisting of SEQ ID NOs: 25, 29, 31, 36, and 37. In some embodiments, the CM1-CM2 substrate of the present disclosure comprises an amino acid sequence selected from the group consisting of SEQ ID NOs: 26, 32, and 34. In some embodiments, the CM1-CM2 substrate of the present disclosure comprises an amino acid sequence selected from the group consisting of SEQ ID NOs: 27, 28, and 33. In some embodiments, the CM1-CM2 substrate of the present disclosure comprises an amino acid sequence selected from the group consisting of SEQ ID NOs: 30 and 35.

In some embodiments, an activatable antibody of the present disclosure comprises a CM1-CM2 substrate comprising an amino acid sequence selected from the group consisting of SEQ ID NOs: 25-43, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 25, 26, 29, 31, 32, 34, 36, and 37, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 27, 28, 30, 33, and 35, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 25, 29, 31, 36, and 37, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 26, 32, and 34, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 27, 28, and 33, as well as an antibody or antigen binding fragment thereof (AB) that binds a target and a masking moiety (MM) that reduces the ability of the antigen- or epitope-binding domain of the AB to bind its target. In some embodiments, an activatable antibody of the present disclosure comprises a CM1-CM2 substrate comprising an amino acid sequence selected from the group consisting of SEQ ID NOs: 30 and 35, as well as an antibody or antigen binding fragment thereof (AB) that binds a target and a masking moiety (MM) that reduces the ability of the antigen- or epitope-binding domain of the AB to bind its target.

In some embodiments, an activatable antibody comprises a CM1-CM2 substrate comprising an amino acid sequence selected from the group consisting of SEQ ID NOs: 25-43, and an anti-EGFR antibody comprising an amino acid sequence of an anti-EGFR antibody disclosed herein. In some embodiments, an activatable antibody comprises a CM1-CM2 substrate comprising an amino acid sequence selected from the group consisting of SEQ ID NOs: 25-43, and an antibody having a light chain comprising amino acid sequence SEQ ID NO: 401 and a heavy chain comprising amino acid sequence SEQ ID NO: 400.

In some embodiments, the CM1-CM2 is included in an activatable antibody having a light chain amino acid sequence selected from the group consisting of SEQ ID NOs: 450-462, and a heavy chain amino acid sequence of SEQ ID NO: 400.

In some embodiments, an isolated polypeptide of the present disclosure comprises a CM1 substrate that is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence is a substrate for at least one MMP and comprises a polypeptide sequence that is not substantially identical to any mammalian polypeptide sequence that is naturally cleaved by the same MMP protease. In some embodiments, the CM1 substrate sequence is a substrate for at least one MMP and comprises a polypeptide sequence that is not substantially identical to any human polypeptide sequence that is naturally cleaved by the same MMP protease. In some embodiments, the CM1 substrate sequence is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence is a substrate for at least one MMP and comprises a polypeptide sequence that is no more than 90% or more identical to any mammalian polypeptide sequence that is naturally cleaved by the same MMP protease. In some embodiments, the CM1 substrate sequence is a substrate for at least one MMP and comprises a polypeptide sequence that is no more than 90% or more identical to any human polypeptide sequence that is naturally cleaved by the same MMP protease. In some embodiments, the CM1 substrate sequence that is a substrate for at least one MMP and comprises a polypeptide sequence that is selected from the group consisting of: ALAHGLF (SEQ ID NO: 1), DLAHPLL (SEQ ID NO: 2), RGPKLYW (SEQ ID NO: 6), RFPYGVW (SEQ ID NO: 7), and QNQALRIA (SEQ ID NO: 16).

In some embodiments, an activatable antibody of the present disclosure comprises a CM1 substrate comprising an amino acid sequence selected from the group consisting of ALAHGLF (SEQ ID NO: 1), DLAHPLL (SEQ ID NO: 2), RGPKLYW (SEQ ID NO: 6), RFPYGVW (SEQ ID NO: 7), and QNQALRIA (SEQ ID NO: 16), as well as an antibody or antigen binding fragment thereof (AB) that binds a target and a masking moiety (MM) that reduces the ability of the antigen- or epitope-binding domain of the AB to bind its target.

In some embodiments, an isolated polypeptide of the present disclosure comprises a CM2 substrate that is a substrate for at least one SP protease and comprises a polypeptide sequence that is not substantially identical to any polypeptide sequence, e.g., any animal polypeptide sequence, that is naturally cleaved by the same SP protease. In some embodiments, the CM2 substrate sequence is a substrate for at least one SP and comprises a polypeptide sequence that is not substantially identical to any mammalian polypeptide sequence that is naturally cleaved by the same SP protease. In some embodiments, the CM2 substrate sequence is a substrate for at least one SP and comprises a polypeptide sequence that is not substantially identical to any human polypeptide sequence that is naturally cleaved by the same SP protease. In some embodiments, the CM2 substrate sequence is a substrate for at least one SP and comprises a polypeptide sequence that is no more than 90% or more identical to any polypeptide sequence, e.g., any animal polypeptide sequence, that is naturally cleaved by the same SP protease. In some embodiments, the CM2 substrate sequence is a substrate for at least one SP and comprises a polypeptide sequence that is no more than 90% or more identical to any mammalian polypeptide sequence that is naturally cleaved by the same SP protease. In some embodiments, the CM2 substrate sequence is a substrate for at least one SP and comprises a polypeptide sequence that is no more than 90% or more identical to any human polypeptide sequence that is naturally cleaved by the same SP protease. In some embodiments, the CM2 substrate sequence that is a substrate for at least one SP and comprises a polypeptide sequence that is selected from the group consisting of: APRSF (SEQ ID NO: 130) and GLPTFVHL (SEQ ID NO: 135).

In some embodiments, an activatable antibody of the present disclosure comprises a CM2 substrate comprising an amino acid sequence selected from the group consisting of APRSF (SEQ ID NO: 130) and GLPTFVHL (SEQ ID NO: 135), as well as an antibody or antigen binding fragment thereof (AB) that binds a target and a masking moiety (MM) that reduces the ability of the antigen- or epitope-binding domain of the AB to bind its target.

In some embodiments, an activatable antibody of the present disclosure comprises a substrate comprising an amino acid sequence selected from the group consisting of SEQ ID NO: 1-16, as well as an antibody or antigen binding fragment thereof (AB) that binds a target and a masking moiety (MM) that reduces the ability of the antigen- or epitope-binding domain of the AB to bind its target.

In some embodiments, the CM1-CM2, CM1, or CM2 substrate is also a substrate for at least one additional protease.

In some embodiments, the at least one additional protease is a different MMP protease than the MMP protease that cleaves the CM1. In some embodiments, the at least one additional protease is an MMP protease selected from the group consisting of MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, the at least one additional protease is a different SP protease than the SP protease that cleaves CM2. In some embodiments, the at least one additional SP protease is selected from the group consisting of uPA; matriptase; activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and TMPRSS4.

In some embodiments, the at least one additional protease is selected from the group consisting of those shown in Table 6.

TABLE 6

| Exemplary Proteases and/or Enzymes |
| --- |
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |

TABLE 6-continued

| Exemplary Proteases and/or Enzymes |
|---|
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |

The disclosure also provides an antibody includes at least a first CM1 and a second CM2 and is conjugated to an agent. In some embodiments, the first CM1 and the second CM2 are each polypeptides of no more than 15 amino acids long. In some embodiments, the activatable antibody is a conjugated activatable antibody that, in the uncleaved state has the structural arrangement from N-terminus to C-terminus as follows: MM-CM1-CM2-AB-Agent, Agent-AB-CM2-CM1-MM, MM-CM2-CM1-AB-Agent, or Agent-AB-CM1-CM2-MM. In some embodiments, the activatable antibody is a conjugated activatable antibody that, in the uncleaved state has the structural arrangement from N-terminus to C-terminus as follows: Agent-MM-CM1-CM2-AB, AB-CM2-CM1-MM-Agent, Agent-MM-CM2-CM1-AB, or AB-CM1-CM2-MM-Agent. In some embodiments, the activatable antibody is a conjugated activatable antibody that, in the uncleaved state has the structural arrangement from N-terminus to C-terminus as follows: Agent-MM-CM1-CM2-AB-Agent, Agent-AB-CM2-CM1-MM-Agent, Agent-MM-CM2-CM1-AB-Agent, or Agent-AB-CM1-CM2-MM-Agent.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: MM1-LP1-CM1-CM2-LP2-AB-Agent, Agent-AB-LP2-CM2-CM1-LP1-MM, MM1-LP1-CM2-CM1-LP2-AB-Agent, or Agent-AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB, AB-LP2-CM2-CM1-LP1-MM-Agent, Agent-MM1-LP1-CM2-CM1-LP2-AB, or AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB-Agent, Agent-AB-LP2-CM2-CM1-LP1-MM-Agent, Agent-MM1-LP1-CM2-CM1-LP2-AB-Agent, or Agent-AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the conjugated activatable antibody includes a linking peptide (LP') between CM1 and CM2. In some embodiments, the conjugated activatable antibody includes a linking peptide (LP1) between the masking moiety (MM) and CM1. In some embodiments, the conjugated activatable antibody includes a linking peptide (LP2) between CM2 and AB. In some embodiments, the conjugated activatable antibody includes a linking peptide (LP1) between the MM and CM1 and a linking peptide (LP2) between CM2 and AB. In some embodiments, the conjugated activatable antibody includes a linking peptide between the MM and CM1 (LP1) and a linking peptide between CM1 and CM2 (LP'). In some embodiments, the conjugated activatable antibody includes a linking peptide (LP') between CM1 and CM2 and a linking peptide (LP2) between CM2 and AB. In some embodiments, the conjugated activatable antibody includes a linking peptide (LP1) between the MM and CM1, a linking peptide (LP') between CM1 and CM2, and a linking peptide (LP2) between CM2 and AB.

In some embodiments, the conjugated activatable antibody includes a linking peptide (LP') between CM1 and CM2. In some embodiments, the conjugated activatable antibody includes a linking peptide (LP1) between the AB and CM1. In some embodiments, the conjugated activatable antibody includes a linking peptide (LP2) between CM2 and the masking moiety (MM). In some embodiments, the conjugated activatable antibody includes a linking peptide (LP1) between the AB and CM1 and a linking peptide (LP2) between CM2 and MM. In some embodiments, the conjugated activatable antibody includes a linking peptide between the AB and CM1 (LP1) and a linking peptide between CM1 and CM2 (LP'). In some embodiments, the conjugated activatable antibody includes a linking peptide (LP') between CM1 and CM2 and a linking peptide (LP2) between CM2 and MM. In some embodiments, the conjugated activatable antibody includes a linking peptide (LP1) between the AB and CM1, a linking peptide (LP') between CM1 and CM2, and a linking peptide (LP2) between CM2 and MM.

In some embodiments, LP' is GG. In some embodiments, LP' is GGSGGS (SEQ ID NO: 218).

In some embodiments, at least one of LP1 or LP2 comprises an amino acid sequence selected from the group consisting of $(GS)_n$, $(GGS)_n$, $(GSGGS)_n$ (SEQ ID NO: 381) and (GGGS). (SEQ ID NO: 382), where n is an integer of at least one.

In some embodiments, at least one of LP1 or LP2 comprises an amino acid sequence selected from the group consisting of GGSG (SEQ ID NO: 202), GGSGG (SEQ ID NO: 203), GSGSG (SEQ ID NO: 204), GSGGG (SEQ ID NO: 205), GGGSG (SEQ ID NO: 206), and GSSSG (SEQ ID NO: 207).

In some embodiments, LP1 comprises the amino acid sequence GSSGGSGGSGGSG (SEQ ID NO: 208), GSSGGSGGSGG (SEQ ID NO: 209), GSSGGSGGSGGS (SEQ ID NO: 210), GSSGGSGGSGGSGGGS (SEQ ID NO: 211), GSSGGSGGSG (SEQ ID NO: 212), or GSSGGSGGSGS (SEQ ID NO: 213), and GGGSSGGS (SEQ ID NO: 214).

In some embodiments, LP2 comprises the amino acid sequence GSS, GGS, GGGS (SEQ ID NO: 215), GSSGT (SEQ ID NO: 216) or GSSG (SEQ ID NO: 217).

In some embodiments, the CM1-CM2 substrate is linked or otherwise attached to an antibody. For example, the CM1-CM2 is used to link one or more agents to the antibody or antigen binding fragment thereof (AB) that binds a given target, such that the CM1-CM2 is cleaved when exposed to the MMP and/or the SP and/or the CP, and the agent is released from the AB. Exemplary targets include, but are not limited to the targets shown in Table 1. Exemplary ABs include, but are not limited to, the antibodies shown in Table 2.

In some embodiments, the AB has a dissociation constant of about 100 nM or less for binding to the target.

In some embodiments, the antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MM has a dissociation constant for binding to the AB that is no more than the dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the antibody and/or activatable antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the antibody and/or the AB of the activatable antibody naturally contains one or more disulfide bonds. In some embodiments, the AB can be engineered to include one or more disulfide bonds.

In some embodiments, the antibody and/or conjugated antibody is monospecific. In some embodiments, the antibody and/or conjugated antibody is multispecific, referred to herein as multispecific antibodies and/or conjugated multispecific antibodies. In some embodiments, the multispecific antibody and/or conjugated multispecific antibody is bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor or other immune effector cell, such as a CAR modified NK cell.

In some embodiments, the activatable antibody and/or conjugated activatable antibody is formulated as part of a pro-Chimeric Antigen Receptor (CAR) modified T cell. In some embodiments, the activatable antibody and/or conjugated activatable antibody is formulated as part of a pro-Chimeric Antigen Receptor (CAR) modified NK cell.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

In some embodiments, the antibodies, antibody conjugates, activatable antibodies, conjugated activatable antibodies, multispecific activatable antibodies, and/or conjugated multispecific activatable antibodies described herein are used in conjunction with one or more additional agents or a combination of additional agents. Suitable additional agents include current pharmaceutical and/or surgical therapies for an intended application, such as, for example, cancer. For example, the activatable antibodies, conjugated activatable antibodies, multispecific activatable antibodies, and/or conjugated multispecific activatable antibodies can be used in conjunction with an additional chemotherapeutic or anti-neoplastic agent.

In some embodiments, the activatable antibody is a multispecific activatable antibody. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 220); a VH CDR2 sequence that includes at least the amino acid sequence VIWSGGNTDYNTPFTS (SEQ ID NO: 221); a VH CDR3 sequence that includes at least the amino acid sequence ALTYYDYEFAY (SEQ ID NO: 222); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 223); a VL CDR2 sequence that includes at least the amino acid sequence KYASESIS (SEQ ID NO: 224); and a VL CDR3 sequence that includes at least the amino acid sequence QQNNNWPTT (SEQ ID NO: 225), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 220); a VH CDR2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 221); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 222); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 223); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 224); and a VL CDR3 sequence that includes a sequence that is at least 90°/%, 91%, 92%, 93%, 94%, 95%, 96%, 97%, 98%, 99% or more identical to the amino acid sequence QQNNNWPTT (SEQ ID NO: 225), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 220); the VH CDR2 sequence includes at least the amino acid sequence VIWSGGNTDYNTPFTS (SEQ ID NO: 221); the VH CDR3 sequence includes at least the amino acid sequence ALTYYDYEFAY (SEQ ID NO: 222); the VL CDR1 sequence includes at least the amino acid sequence RASQSIGTNIH (SEQ ID NO: 223); the VL CDR2 sequence includes at least the amino acid sequence KYASESIS (SEQ ID NO: 224); and the VL CDR3 sequence includes at least the amino acid sequence QQNNNWPTT (SEQ ID NO: 225).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 220); the VH CDR2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 221); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 222); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 223); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 224); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 225).

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 25-43, and an anti-Jagged antibody comprising an amino acid sequence of an anti-Jagged antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 25-43, and an antibody having a light chain comprising amino acid sequence SEQ ID NO: 401 and a heavy chain comprising amino acid sequence SEQ ID NO: 400.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 400 and a light chain amino acid sequence selected from the group consisting of SEQ ID NOs: 403-423 and 450-462.

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker. In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one CM1-CM2 substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM1-CM2 substrate-AB. An example of a spacer joined directly to the N-terminus of MM of the activatable antibody is an amino acid sequence selected from the group consisting of QGQSGQ (SEQ ID NO: 153), GQSGQ (SEQ ID NO: 154), QSGQ (SEQ ID NO: 155), SGQ, GQ, and Q. In some embodiments, the spacer includes at least the amino acid sequence QGQSGQ (SEQ ID NO. 153). In some embodiments, the spacer includes at least the amino acid sequence GQSGQ (SEQ ID NO: 154). In some embodiments, the spacer includes at least the amino acid sequence QSGQ (SEQ ID NO: 155). In some embodiments, the spacer includes at least the amino acid sequence SGQ. In some embodiments, the spacer includes at least the amino acid sequence GQ. In some embodiments, the spacer includes at least the amino acid sequence Q.

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a CM1-CM2 substrate that is a substrate for at least one MMP and at least one SP. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM.

The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a MMP that can cleave the CM1-CM2 substrate.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided.

The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a CM1-CM2 substrate coupled to the AB, wherein the CM1-CM2 substrate is a polypeptide that functions as a substrate for at least one MMP and one SP. In some embodiments, the MM is coupled to the AB via the CM1-CM2 substrate. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides partially reduced activatable antibodies, including but not limited to multispecific activatable antibodies of the disclosure, in which at least one interchain disulfide bond in the activatable antibody has been reduced with a reducing agent without disturbing or otherwise compromising the activity and/or efficacy of the activatable antibody, wherein the activatable antibody includes an antibody or an antigen binding fragment thereof (AB) that specifically binds to a target, a masking moiety (MM) that inhibits the binding of the AB of the activatable antibody in an uncleaved state to the target, and a CM1-CM2 substrate coupled to the AB, and the CM1-CM2 substrate is a polypeptide that functions as a substrate for a protease. The activity and/or efficacy of the activatable antibody is, by way of nonlimiting example, masking activity, activation of the activatable antibody, and/or binding activity of the activated activatable antibody. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate- AB or AB-CM1-CM2 substrate-MM. In some embodiments, the reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and CM1-CM2 substrate coupled to the AB, and the CM1-CM2 substrate is a polypeptide that functions as a substrate for at least one MMP protease and at least one SP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

The disclosure also provides polypeptides and other larger molecules that include one or more of the CM1-CM2 substrate sequences presented herein. By way of non-limiting example, the CM1-CM2 substrate sequences presented herein are useful in prodrug compositions and methods of use thereof. These CM1-CM2 substrate sequences presented herein are also useful in probes and other detection agents and methods of use thereof. For example, the CM1-CM2 substrate sequences presented herein can be used in conjunction with fluors and other quenchers to produce detection agents, such as imaging agents and/or other diagnostic agents. Those of ordinary skill in the art will appreciate that the CM1-CM2 substrate sequences presented herein are useful in any composition and/or method in the art that would use a substrate that is cleavable by at least one MMP and at least one SP.

The disclosure also provides an isolated nucleic acid molecule encoding an antibody and/or an activatable antibody described herein, as well as vectors that include these isolated nucleic acid sequences. The disclosure provides methods of producing an antibody and/or activatable antibody by culturing a cell under conditions that lead to expression of the antibody and/or activatable antibody, wherein the cell comprises such a vector.

The disclosure provides a method of manufacturing a conjugated antibody of the disclosure that bind a given target by (a) culturing a cell comprising a nucleic acid construct that encodes the antibody under conditions that lead to expression of the antibody, (i) wherein the antibody includes a CM1-CM2 substrate, and (ii) wherein the CM1-CM2 substrate is a polypeptide that functions as a substrate for a matrix metalloprotease and a serine protease; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure also provides a method of manufacturing the conjugated activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP and/or CP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; (b) recovering the activatable antibody; and (c) conjugating the recovered antibody to one or more additional agents.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the antibodies, conjugated antibodies, activatable antibodies, and/or conjugated activatable antibodies described herein are used in conjunction with one or more additional agents or a combination of additional agents. Suitable additional agents include current pharmaceutical and/or surgical therapies for an intended application, such as, for example, cancer. For example, the antibodies, conjugated antibodies, activatable antibodies, and/or conjugated activatable antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent (s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, PD-1, TIGIT, TIM-3, B7H4, BTLA, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSFIR inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PD-1 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the antibody, conjugated antibody, activatable antibody, and/or conjugated activatable antibody is administered during and/or after treatment in combination with one or more additional agents such as, for example, a chemotherapeutic agent, an anti-inflammatory agent, and/or an immunosuppressive agent. In some embodiments, the antibody, conjugated antibody, activatable antibody, and/or conjugated activatable antibody and the additional agent are formulated into a single therapeutic composition, and the antibody, conjugated antibody, activatable antibody, and/or conjugated activatable antibody and additional agent are administered simultaneously. Alternatively, the antibody, conjugated antibody, activatable antibody, and/or conjugated activatable antibody and additional agent are separate from each other, e.g., each is formulated into a separate therapeutic composition, and the antibody, conjugated antibody, activatable antibody, and/or conjugated activatable antibody and the additional agent are administered simultaneously, or the antibody, conjugated antibody, activatable antibody, and/or conjugated activatable antibody and the additional agent are administered at different times during a treatment regimen. For example, the antibody, conjugated antibody, activatable antibody, and/or conjugated activatable antibody is administered prior to the administration of the additional agent, the antibody, conjugated antibody, activatable antibody, and/or conjugated activatable antibody is administered subsequent to the administration of the additional agent, or the antibody, conjugated antibody, activatable antibody, and/or conjugated activatable antibody and the additional agent are administered in an alternating fashion. As described herein, the antibody, conjugated antibody, activatable antibody, and/or conjugated activatable antibody and additional agent are administered in single doses or in multiple doses.

In some embodiments, the antibody, conjugated antibody, activatable antibody, and/or conjugated activatable antibody and the additional agent(s) are administered simultaneously. For example, the antibody, conjugated antibody, activatable antibody, and/or conjugated activatable antibody and the additional agent(s) can be formulated in a single composition or administered as two or more separate compositions. In some embodiments, the antibody, conjugated antibody, activatable antibody, and/or conjugated activatable antibody and the additional agent(s) are administered sequentially, or the antibody, conjugated antibody, activatable antibody, and/or conjugated activatable antibody and the additional agent are administered at different times during a treatment regimen.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments the additional agent is an antibody, another conjugated antibody, another activatable antibody and/or another conjugated activatable antibody against the same target as the first conjugated antibody, activatable antibody and/or a conjugated activatable antibody. In some embodiments the additional agent is an antibody, another conjugated antibody, another activatable antibody and/or another conjugated activatable antibody against a target different than the target of the first conjugated antibody, activatable antibody and/or a conjugated activatable antibody.

In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are in single doses or in multiple doses.

The disclosure also provides methods and kits for using the conjugated antibodies, activatable antibodies and/or conjugated activatable antibodies in a variety of diagnostic and/or prophylactic indications.

Pharmaceutical compositions according to the disclosure can include an antibody, conjugated antibody, activatable antibody and/or a conjugated activatable antibody of the disclosure and a carrier. These pharmaceutical compositions can be included in kits, such as, for example, diagnostic kits.

The conjugated antibodies, activatable antibodies, and/or conjugated activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In some embodiments, conjugated antibodies and/or activatable antibodies are designed for cellular uptake and are switchable inside a cell.

As a non-limiting example, the AB is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta 1 | Notch 2 | TNFRS12A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the AB is or is derived from an antibody listed in Table 2.

TABLE 2

| Exemplary sources for Abs | |
|---|---|
| Antibody Trade Name (antibody name) | Target |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 165). By way of non-limiting examples, the MM can include a sequence such as CISPRGC (SEQ ID NO: 166); CISPRGCG (SEQ ID NO: 167); CISPRGCPDGPYVMY (SEQ ID NO: 168); CISPRGCPDGPYVM (SEQ ID NO: 169), CISPRGCEPGTYVPT (SEQ ID NO: 170) and CISPRGCPGQIWHPP (SEQ ID NO: 171). Other suitable masking moieties include any of the EGFR-specific masks disclosed in PCT Publication No. WO 2010/081173, such as, by way of non-limiting example, GSHCLIPINMGAPSC (SEQ ID NO: 172); CISPRGCGGSSASQSGQGSHCLIPINMGAPSC (SEQ ID NO: 173), CNHHYFYTCGCISPRGCPG (SEQ ID NO: 174); ADHVFWGSYGCISPRGCPG (SEQ ID NO: 175), CHHVYWGHCGCISPRGCPG (SEQ ID NO: 176); CPHFTTTSCGCISPRGCPG (SEQ ID NO: 177); CNHHYHYYCGCISPRGCPG (SEQ ID NO: 178); CPHVSFGSCGCISPRGCPG (SEQ ID NO: 179); CPYYTLSYCGCISPRGCPG (SEQ ID NO: 180); CNHVYFGTCGCISPRGCPG (SEQ ID NO: 181); CNHFTLTTCGCISPRGCPG (SEQ ID NO: 182); CHHFTLTTCGCISPRGCPG (SEQ ID NO: 183); YNPCATPMCCISPRGCPG (SEQ ID NO: 184); CNHHYFYTCGCISPRGCG (SEQ ID NO: 185); CNHHYHYYCGCISPRGCG (SEQ ID NO: 186); CNHVYFGTCGCISPRGCG (SEQ ID NO: 187); CHHVYWGHCGCISPRGCG (SEQ ID NO: 188); CPHFTTTSCGCISPRGCG (SEQ ID NO: 189); CNHFTLTTCGCISPRGCG (SEQ ID NO: 190); CHHFTLTTCGCISPRGCG (SEQ ID NO: 191); CPYYTLSYCGCISPRGCG (SEQ ID NO: 192); CPHVSFGSCGCISPRGCG (SEQ ID NO: 193); ADHVFWGSYGCISPRGCG (SEQ ID NO: 194); YNPCATPMCCISPRGCG (SEQ ID NO: 195); CHHVYWGHCGCISPRGCG (SEQ ID NO: 196); C(N/P)H(H/V/F)(Y/TXF/W/T/L)(Y/G/T/S)(T/S/Y/H)CGCISPRGCG (SEQ ID NO: 197); CISPRGCGQPIPSVK (SEQ ID NO: 198), CISPRGCTQPYHVSR (SEQ ID NO: 199), and/or CISPRGCNAVSGLGS (SEQ ID NO: 164).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 200%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes at least one cleavable moiety (CM1) that is a substrate for at least one matrix metalloprotease (MMP) and at least a second cleavable moiety (CM2) that is a subject for at least one serine protease (SP). Such activatable antibodies exhibit activatable/switchable binding, to the AB's target. Activatable antibodies generally include an antibody or antibody fragment (AB), modified by or coupled to a masking moiety (MM) and a CM1-CM2 substrate.

The elements of the activatable antibodies are arranged so that the MM and CM1-CM2 substrate are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM1-CM2 substrate towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM1-CM2 substrate or of the parental AB towards the target. Conversely, the binding affinity of the AB modified with a MM and a CM1-CM2 substrate towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM1-CM2 substrate or of the parental AB towards the target.

When the AB is modified with a MM and a CM1-CM2 substrate and is in the presence of the target but not in the presence of a modifying agent (for example a MMP and a SP), specific binding of the AB to its target is reduced or inhibited, as compared to the specific binding of the AB not modified with an MM and a CM1-CM2 substrate or of the parental AB to the target. When compared to the binding of the parental AB or the binding of an AB not modified with an MM and a CM1-CM2 substrate to its target, the AB's ability to bind the target when modified with an MM and a CM1-CM2 substrate can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification, i.e., cleavage, of the CM1-CM2 substrate by at least one matrix metalloprotease and/or at least one serine protease. The term uncleaved state or fully uncleaved, as used herein, refers to the condition of the activatable antibodies in the absence of cleavage of the CM1-CM2 substrate by a MMP and/or a SP. As discussed above, the term "activatable antibodies" is used herein to refer to an activatable antibody in both its uncleaved (native) state, as well as in its cleaved state. An activatable antibody in its cleaved state is also referred to herein as an activated antibody and/or activated activatable antibody. It will be apparent to the ordinarily skilled artisan that in some embodiments, a cleaved activatable antibody may lack an MM due to cleavage of the CM1-CM2 substrate by protease, resulting in release of at least the MM.

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM1-CM2 substrate than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM1-CM2 substrate and AB of the activatable antibodies are selected so that the AB represents a binding moiety for a given target, and the CM1-CM2 substrate represents a substrate for a MMP and a SP, where the MMP and/or the SP are co-localized with the target at a treatment site or diagnostic site in a subject. The activatable antibodies disclosed herein find particular use where, for example, a MMP and a SP, each capable of cleaving a site in the CM1-CM2 substrate, are present at relatively higher levels in target-containing tissue of a treatment site or diagnostic site than in tissue of non-treatment sites (for example in healthy tissue).

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of a MMP and a SP that are capable of cleaving the CM1-CM2 substrate of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM1-CM2 substrate of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM1-CM2 substrate may be reversed within an activatable antibody. It is also specifically contemplated that the CM and MM may overlap in amino acid sequence, e.g., such that the CM1-CM2 substrate is at least partially contained within the MM.

For example, activatable antibodies can be represented by the following formula (in order from an amino (N) terminal region to carboxyl (C) terminal region:

(MM)-(CM1-CM2 substrate)-(AB)

(AB)-(CM1-CM2 substrate)-(MM)

where MM is a masking moiety, the CM1-CM2 substrate is a cleavable moiety, and AB is an antibody or fragment thereof. As noted above, the term "CM1-CM2 substrate" is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence. It should also be noted that although MM and CM1-CM2 substrate are indicated as distinct components in the formulae above, in all exemplary embodiments (including formulae) disclosed herein it is contemplated that the amino acid sequences of the MM and the CM1-CM2 substrate could overlap, e.g., such that the CM1-CM2 substrate is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments, it may be desirable to insert one or more linkers, e.g., flexible linkers, into the activatable antibody construct to provide for flexibility at one or more of the MM-CM1-CM2 substrate junction, the CM1-CM2 substrate-AB junction, or both. For example, the AB, MM, and/or CM1-CM2 substrate may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represents an amino acid sequence in either N- to C-terminal direction or C- to N-terminal direction):

(MM)-LP1-(CM1-CM2 substrate)-(AB)

(MM)-(CM1-CM2 substrate)-LP2-(AB)

(MM)-LP1-(CM1-CM2 substrate)-LP2-(AB)

wherein MM, CM1-CM2 substrate, and AB are as defined above; wherein LP1 and LP2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM1-CM2 substrate is specifically cleaved by at least one MMP at a rate of about 0.001-1500×$10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×$10^4$ $M^{-1}S^{-1}$ and is specifically cleaved by at least one SP at a rate of about 0.001-1500×$10^4$ $M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×$10^4$ $M^{-1}$ $S^{-1}$.

For specific cleavage by an enzyme, contact between the enzyme and CM1-CM2 substrate is made. When the activatable antibody comprising an AB coupled to a MM and a CM1-CM2 substrate is in the presence of target and sufficient enzyme activity, the CM1-CM2 substrate can be cleaved. Sufficient enzyme activity can refer to the ability of the enzyme to make contact with the CM1-CM2 substrate and effect cleavage. It can readily be envisioned that an enzyme may be in the vicinity of the CM1-CM2 substrate but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers $(G)_n$, glycine-serine polymers (including, for example, (GS)n, (GSGGS)n (SEQ ID NO: 381) and (GGGS)n (SEQ ID NO: 382), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 202), Gly-Gly-Ser-Gly-Gly (SEQ ID NO: 203), Gly-Ser-Gly-Ser-Gly (SEQ ID NO. 204), Gly-Ser-Gly-Gly-Gly (SEQ ID NO: 205), Gly-Gly-Gly-Ser-Gly (SEQ ID NO: 206), Gly-Ser-Ser-Ser-Gly (SEQ ID NO: 207), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

vc-MMAD

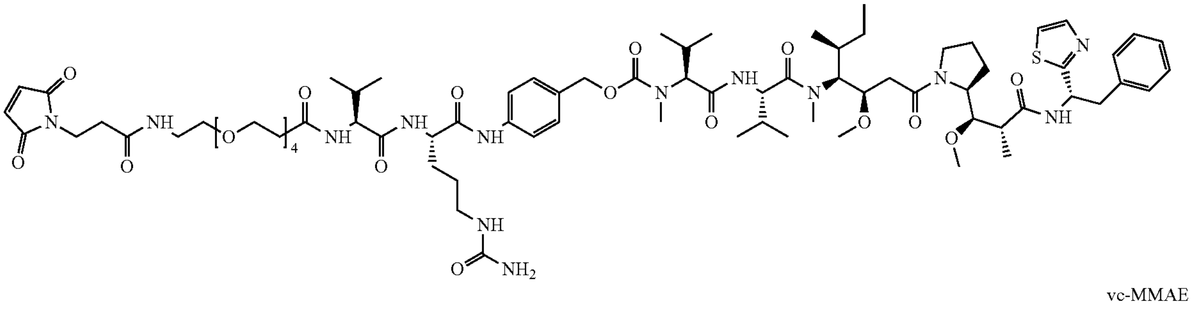

vc-MMAE

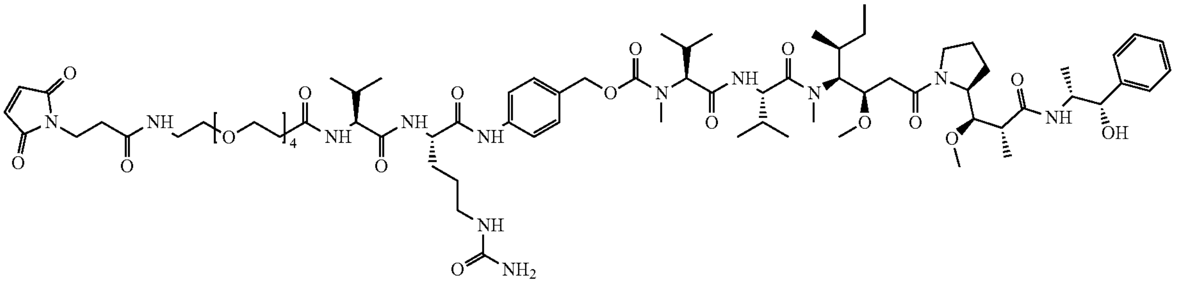

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10, 11-Difluoromethylenedioxycamptothecin |
| Combretastatins |
| Debromoaplysiatoxin |
| Kahalalide-F |
| Discodermolide |
| Ecteinascidins |
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |

TABLE 3-continued

| Exemplary Pharmaceutical Agents for Conjugation |
|---|
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracycline analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine (PBD) |
| Pyrrolobenzodiazepine (PBD) dimers |
| Functionalized pyrrolobenzodiazepines |
| Functionalized pyrrolobenzodiazepine dimers |
| Calicheamicins |
| Podophyllotoxins |
| Taxanes |
| Vinca alkaloids |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}In$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (I-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM1-CM2 substrate and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| **Plasmin cleavable sequences** | |
| Pro-urokinase | PRFKIIGG (SEQ ID NO: 319) |
| | PRFRIIGG (SEQ ID NO: 320) |
| TGFβ | SSRHRRALD (SEQ ID NO: 321) |
| Plasminogen | RKSSIIIRMRDVVL (SEQ ID NO: 322) |
| Staphylokinase | SSSFDKGKYKKGDDA (SEQ ID NO: 323) |
| | SSSFDKGKYKRGDDA (SEQ ID NO: 324) |

TABLE 4-continued

Exemplary Linker Sequences for Conjugation

| Types of Cleavable Sequences | Amino Acid Sequence |
|---|---|
| **Factor Xa cleavable sequences** | |
| | IEGR (SEQ ID NO: 325) |
| | IDGR (SEQ ID NO: 326) |
| | GGSIDGR (SEQ ID NO: 327) |
| **MMP cleavable sequences** | |
| Gelatinase A | PLGLWA (SEQ ID NO: 328) |
| **Collagenase cleavable sequences** | |
| Calf skin collagen (α1(I) chain) | GPQGIAGQ (SEQ ID NO: 329) |
| Calf skin collagen (α2(I) chain) | GPQGLLGA (SEQ ID NO: 330) |
| Bovine cartilage collagen (α1(II) chain) | GIAGQ (SEQ ID NO: 331) |
| Human liver collagen (α1(III) chain) | GPLGIAGI (SEQ ID NO: 332) |
| Human $\alpha_2$M | GPEGLRVG (SEQ ID NO: 333) |
| Human PZP | YGAGLGVV (SEQ ID NO: 334) |
| | AGLGVVER (SEQ ID NO: 335) |
| | AGLGISST (SEQ ID NO: 336) |
| Rat $\alpha_1$M | EPQALAMS (SEQ ID NO: 337) |
| | QALAMSAI (SEQ ID NO: 338) |
| Rat $\alpha_2$M | AAYHLVSQ (SEQ ID NO: 339) |
| | MDAFLESS (SEQ ID NO: 340) |
| Rat $\alpha_1I_3$(2J) | ESLPVVAV (SEQ ID NO: 341) |
| Rat $\alpha_1I_3$(27J) | SAPAVESE (SEQ ID NO: 342) |
| Human fibroblast collagenase (autolytic cleavages) | DVAQFVLT (SEQ ID NO: 343) |
| | VAQFVLTE (SEQ ID NO: 344) |
| | AQFVLTEG (SEQ ID NO: 345) |
| | PVQPIGPQ (SEQ ID NO: 346) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments, the reducing agent that would modify a CM1-CM2 substrate would also modify the linker of the conjugated activatable antibody.

Spacers and Cleavable Elements: In some embodiments, it may be necessary to construct the linker in such a way as to optimize the spacing between the agent and the AB of the activatable antibody. This may be accomplished by use of a linker of the general structure:

$$W—(CH_2)n—Q$$

wherein

W is either $—NH—CH_2—$ or $—CH_2—$,

Q is an amino acid, peptide; and n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |

TABLE 5-continued

| Exemplary Hetero-Bifunctional Cross Linkers HETERO-BIFUNCTIONAL CROSS-LINKERS | | | |
|---|---|---|---|
| Linker | Reactive Toward | Advantages and Applications | Spacer Arm Length after cross-linking (Angstroms) |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment: In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be $$W—(CH_2)n—Q$$

wherein

W is either —NH—$CH_2$— or —$CH_2$—,

Q is an amino acid, peptide; and n is an integer from 0 to 20.

Non-Cleavable Conjugates: In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term “antigen-binding site” or “binding portion” refers to the part of the immunoglobulin molecule that participates in antigen binding. The antigen binding site is formed by amino acid residues of the N-terminal variable (“V”) regions of the heavy (“H”) and light (“L”) chains. Three highly divergent stretches within the V regions of the heavy and light chains, referred to as “hypervariable regions,” are interposed between more conserved flanking stretches known as “framework regions,” or “FRs”. Thus, the term “FR” refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as “complementarity-determining regions,” or “CDRs.” The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term “epitope” includes any protein determinant capable of specific binding to an immunoglobulin, a scFv, or a T-cell receptor. The term “epitope” includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms “specific binding,” “immunological binding,” and “immunological binding properties” refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the “on rate constant” ($K_{on}$) and the “off rate constant” ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 μM, in some embodiments≤100 nM, in some embodiments≤10 nM, and in some embodiments≤100 pM to about 1 pM, as measured by assays such as radioligand binding assays or similar assays known to those skilled in the art.

The term “isolated polynucleotide” as used herein shall mean a polynucleotide of genomic, cDNA, or synthetic origin or some combination thereof, which by virtue of its origin the “isolated polynucleotide” (1) is not associated with all or a portion of a polynucleotide in which the “isolated polynucleotide” is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term “isolated protein” referred to herein means a protein of cDNA, recombinant RNA, or synthetic origin or some combination thereof, which by virtue of its origin, or source of derivation, the “isolated protein” (1) is not associated with proteins found in nature, (2) is free of other proteins from the same source, e.g., free of murine proteins, (3) is expressed by a cell from a different species, or (4) does not occur in nature.

The term “polypeptide” is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term “naturally-occurring” as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term “operably linked” as used herein refers to positions of components so described are in a relationship permitting them to function in their intended manner. A control sequence “operably linked” to a coding sequence is ligated in such a way that expression of the coding sequence is achieved under conditions compatible with the control sequences.

The term “control sequence” as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term “control sequences” is intended to include, at a minimum, all components whose presence is essential for expression and processing, and can also include additional components whose presence is advantageous, for example, leader sequences and fusion partner sequences. The term “polynucleotide” as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%6, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. A method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms “target” and “antigen” are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of auto-reactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/or the OKT3 scFv or OKT3-derived scFv is masked. In some embodiments, the OKT3 scFv or OKT3-derived scFv includes a first antibody or antigen-binding fragment thereof (AB1) that binds CD3E, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a CM1-CM2 substrate is attached to and masks an antigen binding domain of the IgG. In some embodiments, a masking moiety (MM) linked to a CM1-CM2 substrate is attached to and masks an antigen binding domain of at least one scFv. In some embodiments, a masking moiety (MM) linked to a CM1-CM2 substrate is attached to and masks an antigen binding domain of an IgG and a masking moiety (MM) linked to a CM1-CM2 substrate is attached to and masks an antigen binding domain of at least one scFv.

The disclosure provides examples of multispecific activatable antibody structures that include, but are not limited to, the following. $(VL-CL)_2$:(VH-CH1-CH2-CH3-L4-VH*-L3-VL*-LP2-CM1-CM2 substrate-LP1-MM$)_2$; $(VL-CL)_2$:(VH-CH1-CH2-CH3-L4-VL*-L3-VH*-LP2-CM1-CM2 substrate-LP1-MM$)_2$; (MM-LP1-CM1-CM2 substrate-LP2-VL-CL$)_2$:(VH-CH1-CH2-CH3-L4-VH*-L3-VL*$)_2$; (MM-LP1-CM1-CM2 substrate-LP2-VL-CL$)_2$:(VH-CH1-CH2-CH3-L4-VL*-L3-VH*$)_2$; $(VL-CL)_2$:(MM-LP1-CM1-CM2 substrate-LP2-VL*-L3-VH*-L4-VH-CH-CH2-CH3$)_2$; $(VL-CL)_2$:(MM-LP1-CM1-CM2 substrate-LP2-VH*-L3-VL*-L4-VH-CH-CH2-CH3$)_2$; (MM-LP1-CM1-CM2 substrate-LP2-VL-CL$)_2$:(VL*-L3-VH*-L4-VH-CH-CH2-CH3$)_2$; (MM-LP1-CM1-CM2 substrate-LP2-VL-CL$)_2$:(VH*-L3-VL*-L4-VH-CH-CH2-CH3$)_2$; (VL-CL-L4-VH*-L3-VL*-LP2-CM-CM2 substrate-LP1-MM$)_2$:(VH-CH1-CH2-CH3$)_2$; (VL-CL-L4-VL*-L3-VH*-LP2-CM1-CM2 substrate-LP1-MM$)_2$:(VH-CH1-CH2-CH3$)_2$; (MM-LP1-CM1-CM2 substrate-LP2-VL*-L3-VH*-L4-VL-CL$)_2$:(VH-CH1-CH2-CH3$)_2$; (MM-LP1-CM1-CM2 substrate-LP2-VH*-L3-VL*-L4-VL-CL$)_2$:(VH-CH1-CH2-CH3$)_2$; (VL-CL-L4-VH*-L3-VL*-LP2-CM-CM2 substrate-LP1-MM$)_2$:(MM-LP1-CM1-CM2 substrate-LP2-VL*-L3-VH*-L4-VH-CH-CH2-CH3$)_2$; (VL-CL-L4-VH*-L3-VL*-LP2-CM1-CM2 substrate-LP1-MM$)_2$: (MM-LP1-CM1-CM2 substrate-LP2-VH*-L3-VL*-L4-VH-CH-CH2-CH3$)_2$; (VL-CL-L4-VL*-L3-VH*-LP2-CM1-CM2 substrate-LP1-MM$)_2$: (MM-LP1-CM1-CM2 substrate-LP2-VL*-L3-VH*-L4-VH-CH1-CH2-CH3$)_2$; (VL-CL-L4-VL*-L3-VH*-LP2-CM1-CM2 substrate-LP1-MM$)_2$; (MM-LP1-CM1-CM2 substrate-LP2-VH*-L3-VL*-L4-VH-CH-CH2-CH3$)_2$; (VL-CL-L4-VH*-L3-VL*$)_2$: (MM-LP1-CM1-CM2 substrate-LP2-VL*-L3-VH*-L4-VH-CH1-CH2-CH3$)_2$; (VL-CL-L4-VH*-L3-VL*$)_2$: (MM-LP1-CM1-CM2 substrate-LP2-VH*-L3-VL*-L4-VH-CH1-CH2-CH3$)_2$; (VL-CL-L4-VL*-L3-VH*$)_2$: (MM-LP1-CM1-CM2 substrate-LP2-VL*-L3-VH*-L4-VH-CH1-CH2-CH3$)_2$; (VL-CL-L4-VL*-L3-VH*$)_2$: (MM-LP1-CM1-CM2 substrate-LP2-VH*-L3-VL*-L4-VH-CH-CH2-CH3$)_2$; (VL-CL-L4-VH*-L3-VL*-LP2-CM1-CM2 substrate-LP1-MM$)_2$: (VL*-L3-VH*-L4-VH-CH1-CH2-CH3$)_2$; (VL-CL-L4-VH*-L3-VL*-LP2-CM1-CM2 substrate-LP1-MM$)_2$: (VH*-L3-VL*-L4-VH-CH-CH2-CH3$)_2$; (VL-CL-L4-VL*-L3-VH*-LP2-CM-CM2 substrate-LP1-MM$)_2$: (VL*-L3-VH*-L4-VH-CH1-CH2-CH3$)_2$; or (VL-CL-L4-VL*-L3-VH*-LP2-CM-CM2 substrate-LP1-MM$)_2$; (VH*-L3-VL*-L4-VH-CH-CH2-CH3$)_2$, wherein: VL and VH represent the light and heavy variable domains of the first specificity, contained in the IgG; VL* and VH* represent the variable domains of the second specificity, contained in the scFv; LP1 is a linker peptide connecting the masking moiety (MM) and the CM1-CM2 substrate; LP2 is a linker peptide connecting the CM1-CM2 substrate, and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3E, and is or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence.

(SEQ ID NO: 347)
```
GGGSGGGGSGSGGGSGGGGSGGGEIVLTQSPGTLSLSPGERATLSCRASQ

SVSSSYLAWYQQKPGQAPRLLIYGASSRATGIPDRFSGSGSGTDFTLTIS

RLEPEDFAVYYCQQYGSSPLTFGGGTKVEIKRSGGSTITSYNVYYTKLSS

SGTQVQLVQTGGGVVQPGRSLRLSCAASGSTFSSYAMSWVRQAPGKGLEW

VSAISGSGGSTYYADSVKGRFTISRDNSKNTLYLQMNSLRAEDTAVYYCA

TNSLYWYFDLWGRGTLVTVSSAS
```

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 347.

In some embodiments, the anti-CD3ε scFv includes the amino acid sequence:

(SEQ ID NO: 349)

```
GGGSGGGGSGSGGGSGGGGSGGGQVQLQQSGAELARPGASVKMSCKASGY

TFTRYTMHWVKQRPGQGLEWIGYINPSRGYTNYNQKFKDKATLTTDKSSS

TAYMQLSSLTSEDSAVYYCARYYDDHYCLDYWGQGTTLTVSSGGGGSGGG

GSGGGGSQIVLTQSPAIMSASPGEKVTMTCSASSSVSYMNWYQQKSGTSP

KRWIYDTSKLASGVPAHFRGSGSGTSYSLTISGMEAEDAATYYCQQWSSN

PFTFGSGTKLEINR
```

In some embodiments, the anti-CD3ε scFv includes the amino acid sequence that is at least 90%, 91%, 92%, 93%, 94%, 95%, 96%, 97%, 98%, 99% or more identical to the amino acid sequence of SEQ ID NO: 349.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one CM1-CM2 substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4.

In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a CM1-CM2 substrate for an MMP and a SP, where at least one of the MMP and the SP is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1-CM2 substrate.

In some embodiments, the multispecific activatable antibody comprises a linking peptide between the CM1-CM2 substrate and the AB.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, (GSGGS). (SEQ ID NO: 381) and $(GGGS)_n$ (SEQ ID NO: 382), where n is an integer of at least one. In some embodiments, at least one of LP1 or LP2 includes an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, the activatable antibody includes a linking peptide (LP') between CM1 and CM2.

In some embodiments, the activatable antibody comprises a first linking peptide (LP1), a second linking peptide (LP2), and a linking peptide (LP') between CM1 and CM2, and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, linking peptides need not be identical to each other.

In some embodiments, LP' is GG. In some embodiments, LP' is GGSGGS (SEQ ID NO: 218).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a $F(ab')_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has a dissociation constant of about 100 nM or less for binding to its corresponding target or epitope.

In some embodiments, MM1 has a dissociation constant for binding to its corresponding AB that is greater than the dissociation constant of the AB to its corresponding target or epitope.

In some embodiments, MM1 has a dissociation constant for binding to its corresponding AB that is no more than the dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MMJ has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and an additional cleavable moiety (CM') coupled to the AB2, wherein the CM' is either a CM1-CM2 substrate or a polypeptide that functions as a substrate for a second protease. In some embodiments, CM' is a polypeptide of no more than 15 amino acids long. In some embodiments, CM' is a CM1-CM2 substrate, wherein each of CM1 and CM2 in the CM1-CM2 substrate is independently no more than 15 amino acids long.

In some embodiments, the MMP protease, the SP protease, and/or the second protease is co-localized with the second target or epitope in a tissue, and wherein the MMP protease, the SP protease, and/or the second protease cleaves the CM' in the multispecific activatable antibody when the multispecific activatable antibody is exposed to the MMP protease, the SP protease, and/or the second protease. In some embodiments, the MMP protease, the SP protease, and/or the second protease are co-localized with the first target or epitope and the second target or epitope in a tissue. In some embodiments, the MMP protease, the SP protease, and/or the second protease are the same MMP protease and the same SP protease. In some embodiments, the MMP protease, the SP protease, and/or the second protease are not the same MMP protease and not the same SP protease. In some embodiments, the CM1-CM2 substrate and CM' are different substrates for the same MMP protease and same SP protease. In some embodiments, the protease that cleaves CM' is selected from the group consisting of those shown in Table 6.

In some embodiments, each of the MM in the multispecific activatable antibody, e.g., MM1 and at least MM2, has a dissociation constant for binding to its corresponding AB that is greater than the dissociation constant of the AB to its corresponding target or epitope.

In some embodiments, each of the MM in the multispecific activatable antibody has a dissociation constant for binding to its corresponding AB that is no more than the dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant (K) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, the protease that cleaves the CM1-CM2 substrate sequence is co-localized with the target of the AB1 in the multispecific activatable antibody in a tissue, and the MMP protease and/or SP protease, i.e., at least one of the MMP protease and the SP protease, cleave the CM1-CM2 substrate in the multispecific activatable antibody when the multispecific activatable antibody is exposed to the proteases.

In some embodiments, the multispecific activatable antibody includes more than one CM1-CM2 substrate sequence, and the MMP protease and/or the SP protease that cleaves at least one CM1-CM2 substrate sequence is co-localized with the target of at least one of the AB regions in the multispecific activatable antibody in a tissue, and the MMP protease and/or SP protease cleaves the CM1-CM2 substrate in the multispecific activatable antibody when the multispecific activatable antibody is exposed to the proteases.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least twofold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least threefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fourfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fivefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least tenfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least 20-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 40-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 50-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 100-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 200-fold greater than the dissociation constant of an unmodified AB binding to its target, and whereas in the cleaved state, the AB binds its target.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one CM1-CM2 substrate that is a substrate for a MMP protease and a SP protease, where the CM1-CM2 substrate links a MM to an AB. For example, in some embodiments, the multispecific activatable antibody includes at least a first antibody or antibody fragment (AB) that specifically binds a target and a second antibody or antibody fragment (AB2), where at least the first AB in the multispecific activatable antibody is coupled via a first CM1-CM2 substrate to a masking moiety (MM1) that decreases the ability of AB to bind its target. In some bispecific activatable antibody embodiments, AB1 is coupled via the first CM1-CM2 substrate to MM1, and AB2 is coupled via a second CM1-CM2 substrate to a second masking moiety (MM2) that decreases the ability of AB2 to bind its target. In some embodiments, the multispecific activatable antibody comprises more than two AB regions; in some of these embodiments, AB1 is coupled via the first CM1-CM2 substrate to MM1, AB2 is coupled via the second CM1-CM2 substrate to MM2, and AB3 is coupled via a third CM1-CM2 substrate to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a CM1-CM2 substrate and antibody or antibody fragment (AB) that binds a target; an activatable antibody that includes a binding partner for a non-binding steric moiety (BP), a CM1-CM2 substrate and an AB; and an activatable antibody that includes a BP to which an NB has been recruited, a CM1-CM2 substrate and an AB that binds the target. Activatable antibodies in which the NB is covalently linked to the CM1-CM2 substrate and AB of the activatable antibody or is associated by interaction with a BP that is covalently linked to the CM1-CM2 substrate and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a CM1-CM2 substrate; and an antibody or antibody fragment (AB) that binds specifically to the target, wherein the NB is a polypeptide that does not bind specifically to the AB; the CM1-CM2 substrate is a polypeptide that includes a substrate (S) for an enzyme; the CM1-CM2 substrate is positioned such that in an uncleaved state, the NB interferes with binding of the AB to the target and in a cleaved state, the NB does not interfere with binding of the AB to the target; and the NB does not inhibit cleavage of the CM1-CM2 substrate by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) CM1-CM2 substrate is a polypeptide of up to 50 amino acids in length that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; and (iv) the NB does not inhibit cleavage of the CM1-CM2 substrate by the enzyme. For example, each of the CM1 substrate sequence and the CM2 substrate sequence in the CM1-CM2 substrate independent has a length of up to 15 amino acids.

In one embodiment, the activatable antibody includes a non-binding steric moiety (NB), a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; (iv) the NB does not inhibit cleavage of the CM1-CM2 substrate by the enzyme; and (v) the activatable antibody has the structural arrangement from N-terminus to C-terminus as follows in the uncleaved state: NB-CM1-CM2 substrate-AB or AB-CM1-CM2 substrate-NB.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CM1-CM2 substrate by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a CM1-CM2 substrate; and an antibody or antibody fragment (AB) that binds specifically to the target, wherein the BP is a polypeptide that binds to the NB when exposed thereto; the NB does not bind specifically to the AB; the CM1-CM2 substrate is a polypeptide that includes a substrate (S) for an enzyme; the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CM1-CM2 substrate by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CM1-CM2 substrate, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CM1-CM2 substrate is a polypeptide that includes a substrate (S) for a protease. In some examples of any of these activatable antibody embodiments, the protease is co-localized with the in a tissue, and the protease cleaves the CM1-CM2 substrate in the activatable antibody when the activatable antibody is exposed to the protease. In some examples of any of these activatable antibody embodiments, the CM1-CM2 substrate is a polypeptide of up to 50 amino acids in length. In some examples of any of these activatable antibody embodiments, the CM1-CM2 substrate is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CM1-CM2 substrate-AB, AB-CM1-CM2 substrate-NB, BP-CM1-CM2 substrate-AB or AB-CM1-CM2 substrate-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM1-CM2-AB, NB:BP-CM2-CM1-AB, AB-CM1-CM2-BP:NB or AB-CM2-CM1-BP:NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB:BP. When the NB-containing activatable antibody is in the presence of the target, specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CM1-CM2 substrate cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CM1-CM2 substrate, wherein the first CM1-CM2 substrate is cleavable by a cleaving agent in a first target tissue and wherein the second CM1-CM2 substrate is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state, the NB interferes with binding of the AB to the target and in a cleaved state, the NB does not interfere with binding of the AB to the target; and (4) the NB does not inhibit cleavage of the CM1-CM2 substrate by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CM1-CM2 substrate by the enzyme;

and (b) recovering the activatable antibody. In some examples of this embodiment, the BP of the activatable antibody is bound to the NB.

Use of Activatable Antibodies and Conjugated Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A conjugated antibody, an activatable antibody and/or a conjugated activatable antibody can be administered in the form of pharmaceutical compositions. Principles and considerations involved in preparing such compositions, as well as guidance in the choice of components are provided, for example, in Remington. The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N J, 1995, "Immunoassay", E. Diamandis and T. Christopoulus, Academic Press, Inc., San Diego, C A, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be substrate for a matrix metalloprotease (MMP) and a serine protease (SP) found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with an MMP whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a matrix metalloprotease (MMP) and one serine protease (SP) that are specific for the CM1-CM2 substrate of the activatable antibody. In some embodiments, the presence of the MMP can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a MMP and a SP specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a MMP and a SP that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows. MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a CM1-CM2 substrate that is cleaved by the cleaving agent, an antigen binding domain (AB) that specifically binds the target, and a detectable label, wherein the activatable antibody in an uncleaved, non-activated state comprises a structural arrangement from N-terminus to C-terminus as follows: MM-CM1-CM2 substrate-AB or AB-CM1-CM2 substrate-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM1-CM2 substrate; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM1-CM2 substrate and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM1-CM2 substrate; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments, in vivo imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested in these methods are identified as suitable candidates for treatment with such an activatable antibody comprising such a CM1-CM2 substrate. Likewise, patients that test negative for both of the targets (e.g., the target) and the protease that cleaves the substrate in the CM1-CM2 substrate in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, patients that test negative for either of the target (e.g., the target) are identified as suitable candidates for treatment with such an activatable antibody comprising such a CM1-CM2 substrate. In some embodiments, patients that test negative for either of the target (e.g., the target) are identified as not being suitable candidates for treatment with such an activatable antibody comprising such a CM1-CM2 substrate. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the CM1-CM2 substrate of the activatable antibody and/or conjugated activatable antibody being tested in these methods are identified as suitable candidates for treatment with such antibody and/or such a conjugated activatable antibody comprising such a CM1-CM2 substrate, and the patient is then administered a therapeutically effective amount of the activatable antibody and/or conjugated activatable antibody that was tested. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM1-CM2 substrate that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM1-CM2 substrate. In some embodiments of these methods and kits, the activatable antibody comprises a linker peptide, where the linker peptide is positioned between the AB and the CM1-CM2 substrate. In some embodiments of these methods and kits, the activatable antibody comprises a first linker peptide (LP1) and a second linker peptide (LP2), wherein the first linker peptide is positioned between the MM and the CM1-CM2 substrate and the second linker peptide is positioned between the AB and the CM1-CM2 substrate. In some embodiments of these methods and kits, each of LP1 and LP2 is a peptide of about 1 to 20 amino acids in length, and wherein each of LP1 and LP2 need not be the same linker. In some embodiments of these methods and kits, one or both of LP1 and LP2 comprises a glycine-serine polymer. In some embodiments of these methods and kits, at least one of LP1 and LP2 comprises an amino acid sequence selected from the group consisting of (GS)n, (GSGGS)n (SEQ ID NO: 381) and (GGGS)n (SEQ ID NO: 382), where n is an integer of at least one. In some embodiments of these methods and kits, at least one of LP1 and LP2 comprises an amino acid sequence having the formula (GGS)n, where n is an integer of at least one. In some embodiments of these methods and kits, at least one of LP1 and LP2 comprises an amino acid sequence selected from the group consisting of Gly-Gly-Ser-Gly (SEQ ID NO: 383), Gly-Gly-Ser-Gly-Gly (SEQ ID NO: 384), Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), and Gly-Ser-Ser-Ser-Gly (SEQ ID NO: 388).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM1-CM2 substrate is a polypeptide that functions as a substrate for the protease, wherein the protease cleaves the CM1-CM2 substrate in the activatable antibody when the activatable antibody is exposed to the protease. In some embodiments of these methods and kits, each of the CM1 substrate sequence and the CM2 substrate sequence in the CM1-CM2 substrate is independently a polypeptide of up to 15 amino acids in length. In some embodiments of these methods and kits, the CM1-CM2 substrate is coupled to the N-terminus of the AB. In some embodiments of these methods and kits, the CM1-CM2 substrate is coupled to the C-terminus of the AB. In some embodiments of these methods and kits, the CM1-CM2 substrate is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM1-CM2 substrate of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

In some embodiments, in situ imaging and/or in vino imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target and the protease that cleaves the substrate in the CM1-CM2 substrate in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

Pharmaceutical Compositions

The conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: Activatable Antibodies And Matrix Metalloprotease (MMP) Cleavable Substrates The studies provided herein describe exemplary matrix metalloprotease (MMP) substrates of the present disclosure and exemplary activatable antibodies that include MMP substrates of the present disclosure.

Exemplary activatable antibodies were constructed such that each one includes one of the MMP substrates listed in Table 1. The exemplary activatable antibodies of the present disclosure, the sequences of which are listed in Table 2, include an antibody or antigen binding fragment thereof (AB) that is based on a mouse/human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a cleavable moiety (CM), and the CM includes at least one MMP substrate sequence of Table 1.

TABLE 1

| Matrix Metalloprotease (MMP) Substrates | | |
|---|---|---|
| Name | Sequence | SEQ ID NO: |
| 4001 | ALAHGLF | 1 |
| 4002 | DLAHPLL | 2 |
| 4003 | AFRHLR | 3 |
| 4004 | PHGFFQ | 4 |
| 4005 | SVHHLI | 5 |
| 4006 | RGPKLYW | 6 |
| 4007 | RFPYGVW | 7 |
| 4008 | HVPRQV | 8 |
| 4009 | SNPFKY | 9 |
| 4010 | RFPLKV | 10 |
| 4011 | PFHLSR | 11 |
| 4012 | STVFHM | 12 |
| 4013 | MGPWFM | 13 |
| 4014 | RHLAKL | 14 |
| 4015 | PLGVRGK | 15 |
| 4016 | QNQALRIA | 16 |

TABLE 2

| Activatable Antibody Sequences |
|---|
| Anti-EGFR Activatable Antibody (c225v5) Heavy Chain (amino acid sequence) (SEQ ID NO: 400)<br>QVQLKQSGPGLVQPSQSLSITCTVSGFSLTNYGVHWVRQSPGKGLEWLGVIWSGGNTDYNTPFT<br>SRLSINKDNSKSQVFFKMNSLQSQDTAIYYCARALTYYDYEFAYWGQGTLVTVSAASTKGPSVF<br>PLAPSSKSTSGGTAALGCLVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVSVLTVLHQDWLNGKE<br>YKCKVSNKALPAPIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNHYTQKSLSLSPG<br>K |
| Anti-EGFR Activatable Antibody Light Chain (amino acid sequence) (SEQ ID NO: 399)<br>DILLTQSPVILSVSPGERVSFSCRASQSIGTNIHWYQQRTNGSPRLLIKYASESISGIPSRFSG<br>SGSGTDFTLSINSVESEDIADYYCQQNNNWPTTFGAGTKLELKRTVAAPSVFIFPPSDEQLKSG<br>TASVVCLLNNFYPREAKVQWKVDNALQSGNSQESVTEQDSKDSTYSLSSTLTLSKADYEKHKVY<br>ACEVTHQGLSSPVTKSFNRGEC |
| Anti-EGFR Activatable Antibody Light Chain (amino acid sequence) (SEQ ID NO: 401)<br>QILLTQSPVILSVSPGERVSFSCRASQSIGTNIHWYQQRTNGSPRLLIKYASESISGIPSRFSG<br>SGSGTDFTLSINSVESEDIADYYCQQNNNWPTTFGAGTKLELKRTVAAPSVFIFPPSDEQLKSG<br>TASVVCLLNNFYPREAKVQWKVDNALQSGNSQESVTEQDSKDSTYSLSSTLTLSKADYEKHKVY<br>ACEVTHQGLSSPVTKSFNRGEC |
| Anti-EGFR Activatable Antibody (c225v5-3954-NSUB) Light Chain (amino acid sequence) (SEQ ID NO: 402)<br>QGQSGQCISPRGCPDGPYVMYGSSGGSGGSGGSGGGSGGGSGGSDILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-4001SL) Light Chain (amino acid sequence) (SEQ ID NO: 403)<br>QGQSGQCISPRGCPDGPYVMYGGGSSGGSALAHGLFGGGSQILLTQSPVILSVSPGERVSFSCR<br>ASQSIGTNIHWYQQRTNGSPRLLIKYASESISGIPSRFSGSGSGTDFTLSINSVESEDIADYYC<br>QQNNNWPTTFGAGTKLELKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| Anti-EGFR Activatable Antibody (c225v5-3954-4001LL) Light Chain (amino acid sequence) (SEQ ID NO: 404)<br>QGQSGQCISPRGCPDGPYVMYGSSGGSGGSGGSGALAHGLFGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |

TABLE 2-continued

| Activatable Antibody Sequences |
| --- |
| Anti-EGFR Activatable Antibody (c225v5-3954-4002SL) Light Chain (amino acid sequence) (SEQ ID NO: 405)<br>QGQSGQCISPRGCPDGPYVMYGGGSSGGSDLAHPLLGGGSQILLTQSPVILSVSPGERVSFSCR<br>ASQSIGTNIHWYQQRTNGSPRLLIKYASESISGIPSRFSGSGSGTDFTLSINSVESEDIADYYC<br>QQNNNWPTTFGAGTKLELKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| Anti-EGFR Activatable Antibody (c225v5-3954-4003SL) Light Chain (amino acid sequence) (SEQ ID NO: 406)<br>QGQSGQCISPRGCPDGPYVMYGGGSSGGSAFRHLRGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4004LL) Light Chain (amino acid sequence) (SEQ ID NO: 407)<br>QGQSGQCISPRGCPDGPYVMYGSSGGSGGSGGSGPHGFFQGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-4005SL) Light Chain (amino acid sequence) (SEQ ID NO: 408)<br>QGQSGQCISPRGCPDGPYVMYGGGSSGGSSVHHLIGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4006SL) Light Chain (amino acid sequence) (SEQ ID NO: 409)<br>QGQSGQCISPRGCPDGPYVMYGGGSSGGSRGPKLYWGGGSQILLTQSPVILSVSPGERVSFSCR<br>ASQSIGTNIHWYQQRTNGSPRLLIKYASESISGIPSRFSGSGSGTDFTLSINSVESEDIADYYC<br>QQNNNWPTTFGAGTKLELKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| Anti-EGFR Activatable Antibody (c225v5-3954-4006LL) Light Chain (amino acid sequence) (SEQ ID NO: 410)<br>QGQSGQCISPRGCPDGPYVMYGSSGGSGGSGGSGRGPKLYWGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-4007SL) Light Chain (amino acid sequence) (SEQ ID NO: 411)<br>QGQSGQCISPRGCPDGPYVMYGGGSSGGSRFPYGVWGGGSQILLTQSPVILSVSPGERVSFSCR<br>ASQSIGTNIHWYQQRTNGSPRLLIKYASESISGIPSRFSGSGSGTDFTLSINSVESEDIADYYC<br>QQNNNWPTTFGAGTKLELKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| Anti-EGFR Activatable Antibody (c225v5-3954-4008SL) Light Chain (amino acid sequence) (SEQ ID NO: 412)<br>QGQSGQCISPRGCPDGPYVMYGGGSSGGSHVPRQVGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4008LL) Light Chain (amino acid sequence) (SEQ ID NO: 413)<br>QGQSGQCISPRGCPDGPYVMYGSSGGSGGSGGSGHVPRQVGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-4009SL) Light Chain (amino acid sequence) (SEQ ID NO: 414)<br>QGQSGQCISPRGCPDGPYVMYGGGSSGGSSNPFKYGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4010SL) Light Chain (amino acid sequence) (SEQ ID NO: 415)<br>QGQSGQCISPRGCPDGPYVMYGGGSSGGSRFPLKVGGGSQILLTQSPVILSVSPGERVSFSCRA<br>SQSIGTNIHWYQQRTNGSPRLLIKYASESISGIPSRFSGSGSGTDFTLSINSVESEDIADYYCQ |

TABLE 2-continued

| Activatable Antibody Sequences |
|---|
| QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4011SL) Light Chain<br>(amino acid sequence) (SEQ ID NO: 416)<br>QGQSGQCISPRGCPDGPYVMYGGGSSGGSPFHLSRGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4012SL) Light Chain<br>(amino acid sequence) (SEQ ID NO: 417)<br>QGQSGQCISPRGCPDGPYVMYGGGSSGGSSTVFHMGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4013SL) Light Chain<br>(amino acid sequence) (SEQ ID NO: 418)<br>QGQSGQCISPRGCPDGPYVMYGGGSSGGSMGPWFMGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4013LL) Light Chain<br>(amino acid sequence) (SEQ ID NO: 419)<br>QGQSGQCISPRGCPDGPYVMYGSSGGSGGSGGSGMGPWFMGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-4014SL) Light Chain<br>(amino acid sequence) (SEQ ID NO: 420)<br>QGQSGQCISPRGCPDGPYVMYGGGSSGGSRHLAKLGGGSQILLTQSPVILSVSPGERVSFSCRA<br>SQSIGTNIHWYQQRTNGSPRLLIKYASESISGIPSRFSGSGSGTDFTLSINSVESEDIADYYCQ<br>QNNNWPTTFGAGTKLELKRTVAAPSVFIFPPSDEQLKSGTASVVCLLNNFYPREAKVQWKVDNA<br>LQSGNSQESVTEQDSKDSTYSLSSTLTLSKADYEKHKVYACEVTHQGLSSPVTKSFNRGEC |
| Anti-EGFR Activatable Antibody (c225v5-3954-4015SL) Light Chain<br>(amino acid sequence) (SEQ ID NO: 421)<br>QGQSGQCISPRGCPDGPYVMYGGGSSGGSPLGVRGKGGGSQILLTQSPVILSVSPGERVSFSCR<br>ASQSIGTNIHWYQQRTNGSPRLLIKYASESISGIPSRFSGSGSGTDFTLSINSVESEDIADYYC<br>QQNNNWPTTFGAGTKLELKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSPVTKSFNRGEC |
| Anti-EGFR Activatable Antibody (c225v5-3954-4015LL) Light Chain<br>(amino acid sequence) (SEQ ID NO: 422)<br>QGQSGQCISPRGCPDGPYVMYGSSGGSGGSGGSGPLGVRGKGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-4016) Light Chain<br>(amino acid sequence) (SEQ ID NO: 423)<br>QGQSGQCISPRGCPDGPYVMYGSSGGSGGSGGSGQNQALRIAGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |
| Anti-EGFR Activatable Antibody (c225v5-3954-2011LL) Light Chain<br>(amino acid sequence) (SEQ ID NO: 480)<br>QGQSGQCISPRGCPDGPYVMYGSSGGSGGSGGSGISSGLLSGRSDNPGGGSQILLTQSPVILSV<br>SPGERVSFSCRASQSIGTNIHWYQQRTNGSPRLLIKYASESISGIPSRFSGSGSGTDFTLSINS<br>VESEDIADYYCQQNNNWPTTFGAGTKLELKRTVAAPSVFIFPPSDEQLKSGTASVVCLLNNFYP<br>REAKVQWKVDNALQSGNSQESVTEQDSKDSTYSLSSTLTLSKADYEKHKVYACEVTHQGLSSPV<br>TKSFNRGEC |
| Anti-EGFR Activatable Antibody (c225v5-3954-3011LL) Light Chain<br>(amino acid sequence) (SEQ ID NO: 481)<br>QGQSGQCISPRGCPDGPYVMYGSSGGSGGSGGSGAVGLLAPPGGLSGRSDNPGGGSQILLTQSP<br>VILSVSPGERVSFSCRASQSIGTNIHWYQQRTNGSPRLLIKYASESISGIPSRFSGSGSGTDFT<br>LSINSVESEDIADYYCQQNNNWPTTFGAGTKLELKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQG<br>LSSPVTKSFNRGEC |

TABLE 2-continued

| Activatable Antibody Sequences |
|---|
| Anti-EGFR Activatable Antibody (c225v5-3954-1001SL) Light Chain (amino acid sequence) (SEQ ID NO: 482)<br>QGQSGQCISPRGCPDGPYVMYGGGSSGGSISSGLLSSGGGSQILLTQSPVILSVSPGERVSFSC<br>RASQSIGTNIHWYQQRTNGSPRLLIKYASESISGIPSRFSGSGSGTDFTLSINSVESEDIADYY<br>CQQNNNWPTTFGAGTKLELKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSSPVTKSFNRGEC |
| Anti-EGFR Activatable Antibody (c225v5-3954-1001LL) Light Chain (amino acid sequence) (SEQ ID NO: 483)<br>QGQSGQCISPRGCPDGPYVMYGSSGGSGGSGGSGISSGLLSSGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |
| Anti-EGFR Activatable Antibody (c225v5-3954-1004SL) Light Chain (amino acid sequence) (SEQ ID NO: 484)<br>QGQSGQCISPRGCPDGPYVMYGGGSSGGSAVGLLAPPGGGSQILLTQSPVILSVSPGERVSFSC<br>RASQSIGTNIHWYQQRTNGSPRLLIKYASESISGIPSRFSGSGSGTDFTLSINSVESEDIADYY<br>CQQNNNWPTTFGAGTKLELKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSSPVTKSFNRGEC |
| Anti-EGFR Activatable Antibody (c225v5-3954-1004LL) Light Chain (amino acid sequence) (SEQ ID NO: 485)<br>QGQSGQCISPRGCPDGPYVMYGSSGGSGGSGGSGPAVGLLAPPGGGSQILLTQSPVILSVSPGE<br>RVSFSCRASQSIGTNIHWYQQRTNGSPRLLIKYASESISGIPSRFSGSGSGTDFTLSINSVESE<br>DIADYYCQQNNNWPTTFGAGTKLELKRTVAAPSVFIFPPSDEQLKSGTASVVCLLNNFYPREAK<br>VQWKVDNALQSGNSQESVTEQDSKDSTYSLSSTLTLSKADYEKHKVYACEVTHQGLSSPVTKSF<br>NRGEC |
| Anti-EGFR Activatable Antibody (c225v5-3954-1005SL) Light Chain (amino acid sequence) (SEQ ID NO: 486)<br>QGQSGQCISPRGCPDGPYVMYGGGSSGGSGPSHLVLTGGGSQILLTQSPVILSVSPGERVSFSC<br>RASQSIGTNIHWYQQRTNGSPRLLIKYASESISGIPSRFSGSGSGTDFTLSINSVESEDIADYY<br>CQQNNNWPTTFGAGTKLELKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQGLSSPVTKSFNRGEC |
| Anti-EGFR Activatable Antibody (c225v5-3954-1005LL) Light Chain (amino acid sequence) (SEQ ID NO: 487)<br>QGQSGQCISPRGCPDGPYVMYGSSGGSGGSGGSGGPSHLVLTGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |

Example 2: In Vitro Stability of Activatable Antibodies with MMP-Cleavable Substrates The studies provided herein evaluate the in vitro stability of activatable antibodies containing matrix metalloprotease (MMP) substrates of the present disclosure.

The stability of the activatable antibodies of the present disclosure were measured by in the presence of either recombinant MMP9 or recombinant MMP14 matrix metalloproteases. Each activatable antibody (100 μg/mL) was incubated with 50 mM of the indicated recombinant protease for 24 hours at 37° C., and the fraction of the activatable antibody that was cleaved was measured by capillary electrophoresis for each protease enzyme. The exemplary results of this in vitro study are summarized in Table 3.

These exemplary results show that the substrates of the present disclosure showed a range of cleavability by MMP9 or MMP14 enzymes. These exemplary results also show a group of substrates in which the MMP9 and MMP14 cleavability are both at least 85%. In some embodiments, such substrates may include isolated polypeptide that include the amino acid sequence of ALAHGLF (SEQ ID NO: 1), DLAHPLL (SEQ ID NO: 2), or RGPKLYW (SEQ ID NO: 6).

These exemplary results also show a group of substrates in which the MMP9 and MMP14 cleavability are both at least 90%. In some embodiments, such substrates may include isolated polypeptide that include the amino acid sequence of ALAHGLF (SEQ ID NO: 1).

TABLE 3

In Vitro Activation of MMP-Cleavable Activatable Antibodies

| Substrate in Activatable Antibody (%) | Substrate | Substrate SEQ ID NO. | MMP14 Cleavability (%) | MMP9 Cleavability |
|---|---|---|---|---|
| c225v5-3954-4001-SL | ALAHGLF | 1 | 96.5 | 94.5 |
| c225v5-3954-4001-LL | ALAHGLF | 1 | 100 | 100.0 |

TABLE 3-continued

In Vitro Activation of MMP-Cleavable Activatable Antibodies

| Substrate in Activatable Antibody (%) | Substrate | Substrate SEQ ID NO. | MMP14 Cleavability (%) | MMP9 Cleavability |
|---|---|---|---|---|
| c225v5-3954-4002-SL | DLAHPLL | 2 | 85.9 | 87.5 |
| c225v5-3954-4003-SL | AFRHLR | 3 | 53.1 | 6.0 |
| c225v5-3954-4004-LL | PHGFFQ | 4 | 46.2 | 29.8 |
| c225v5-3954-4005-SL | SVHHLI | 5 | 24.4 | 70.5 |
| c225v5-3954-4006-LL | RGPKLYW | 6 | 84.2 | 90.8 |
| c225v5-3954-4006-SL | RGPKLYW | 6 | 85.7 | 92.9 |
| c225v5-3954-4007-SL | RFPYGVW | 7 | 0.0 | 69.5 |
| c225v5-3954-4008-LL | HVPRQV | 8 | 0.0 | 55.2 |
| c225v5-3954-4009-SL | SNPFKY | 9 | 0.0 | 22.1 |
| c225v5-3954-4010-SL | RFPLKV | 10 | 0.0 | 18.0 |
| c225v5-3954-4011-SL | PFHLSR | 11 | 9.9 | 78.8 |
| c225v5-3954-4012-SL | STVFHM | 12 | 0.0 | 56.5 |
| c225v5-3954-4014-SL | RHLAKL | 14 | 30.5 | 0.0 |
| c225v5-3954-4015-LL | PLGVRGK | 15 | 0.0 | 90.0 |

Example 3: In Vivo Stability of Activatable Antibodies with MMP-Cleavable Substrates The studies provided herein evaluate the in vivo stability of activatable antibodies containing matrix metalloprotease (MMP) substrates of the present disclosure.

These exemplary studies measured the stability of activatable antibodies containing MMP substrates of the present disclosure by administering a dose of the activatable antibodies to mice, and then measuring by Western blot the fraction of the activatable antibody in plasma that was observed to be cleaved. The stability was compared to other known activatable antibodies that have substrates e.g. 2011 (ISSGLLSGRSDNP, SEQ ID NO: 21), and 3011 (AVGLLAPPGGLSGRSDNP, SEQ ID NO: 22) that include at least one MMP substrate and at least serine protease substrate or a substrate 1001 (ISSGLLSS, SEQ ID NO: 17) that includes at least one MMP substrate.

In this study, nu/nu mice of about 7-8 weeks of age were administered intraperitoneally with the indicated test article at a dosage of 12.5 mg/kg. After 7 days following the administration, terminal blood was collected by cardiac puncture and processed to plasma within 1 hour of collection. The collected sample was diluted 1:100 in phosphate-buffered saline solution and denatured and analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 4 and FIG. 1.

TABLE 4

In Vivo Stability of Activatable Antibodies

| Test Article | % Activated after 7 days |
|---|---|
| C225v5-3954-2011 LL | 35.80 |
| C225v5-3954-3011 LL | 62.85 |
| C225v5-3954-4016 | 20.30 |
| C225v5-3954-4001 LL | 22.37 |
| C225v5-3954-4001 SL | 27.23 |
| C225v5-3954-4003 SL | 29.70 |
| C225v5-3954-4006 LL | 22.70 |
| C225v5-3954-4008 SL | 17.93 |
| C225v5-3954-4008 LL | 17.77 |
| C225v5-3954-4012 SL | 13.20 |
| C225v5-3954-4015 LL | 50.43 |
| C225v5-3954-1001 LL | 19.77 |

These exemplary results showed that certain activatable antibodies that include MMP substrates of the present disclosure demonstrated a higher in vivo stability than activatable antibodies with both serine protease and MMP substrates.

These exemplary results also show a group of substrates in which the in vivo stability is less than 30% activation. In some embodiments, such substrates may include isolated polypeptide that include the amino acid sequence of ALAHGLF (SEQ ID NO: 1) or RGPKLYW (SEQ ID NO: 6).

These exemplary results also show a group of substrates in which the in vivo stability is less than 25% activation. In some embodiments, such substrates may include isolated polypeptide that include the amino acid sequence of ALAHGLF (SEQ ID NO: 1) or RGPKLYW (SEQ ID NO: 6).

Example 4: Masking Efficiency of Activatable Antibodies with MMP-Cleavable Substrates The studies provided herein evaluate the in vitro masking efficiency of activatable antibodies that include matrix metalloprotease (MMP) substrates of the present disclosure.

Figure 2A:
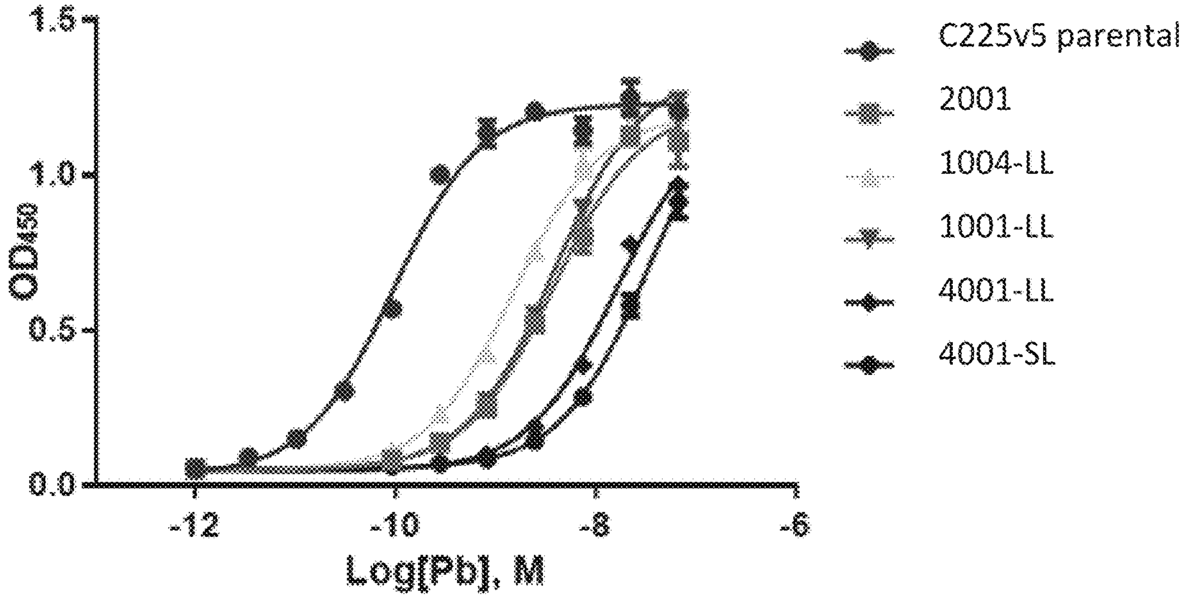
FIGS. 2A and 2B are graphs showing exemplary results of the in vitro binding to EGFR of the indicated anti-EGFR activatable antibodies of the present disclosure. These exemplary results showed that the MMP substrate effected the masking efficiency of the prodomain of the activatable antibody.
Figure 2B:
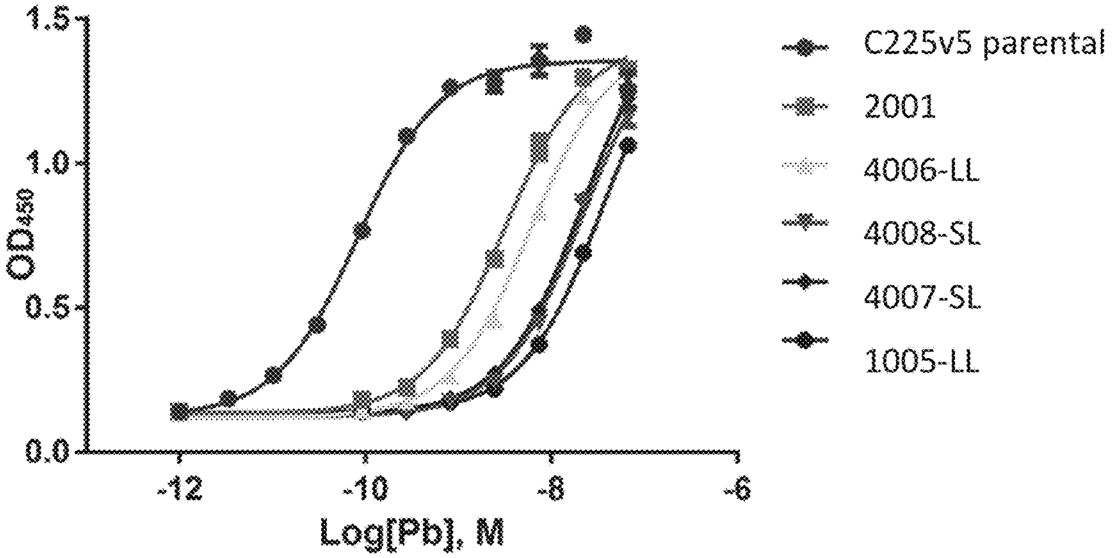

In these studies, a solid-phase binding assay (ELISA) was used to demonstrate the binding affinity of anti-EGFR activatable antibodies that include MMP substrates of the present disclosure to recombinant EGFR. As shown in FIGS. 2A and 2B, the binding affinity to EGFR of the activatable antibodies with the indicated substrate of the present disclosure was measured and compared to the c225v5 parental antibody. The masking efficiency was compared to other activatable antibodies that having known substrates e.g. 2001 (ISSGLLSGRSDNH, SEQ ID NO: 23) that includes at least one MMP substrate and at least serine protease substrate or a substrate 1001 (ISSGLLSS, SEQ ID NO: 17), 1004 (AVGLLAPP, SEQ ID NO: 18), and 1005 (GPSHLVLT, SEQ ID NO: 19) that includes at least one MMP substrate. A summary of these exemplary results is shown in Table 5 and FIGS. 2A and 2B.

These exemplary results showed that the MMP substrate had an effect on the masking efficiency of the masking moiety in the activatable antibody, in some cases increasing the apparent masking efficiency of the masking moiety in the prodomain of the activatable antibody.

These exemplary results also show a group of substrates in which the masking efficiency is greater than 70. In some embodiments, such substrates may include isolated polypeptide that include the amino acid sequence of ALAHGLF (SEQ ID NO: 1), RGPKLYW (SEQ ID NO: 6), or RFPYGVW (SEQ ID NO: 7).

These exemplary results also show a group of substrates in which the masking efficiency is greater than 160. These exemplary results also show a group of substrates in which the masking efficiency is from 160 to 350. In some embodiments, such substrates may include isolated polypeptide that include the amino acid sequence of ALAHGLF (SEQ ID NO: 1) or RFPYGVW (SEQ ID NO: 7).

TABLE 5

In Vitro Binding Activity and Masking Efficiency of Activatable Antibodies

| Test Article | $K_{Da}$ (nM) | Masking Efficiency |
|---|---|---|
| C225v5 parental antibody (FIG. 2A) | 0.094 | 1 |
| C225v5-3954-2001 (FIG. 2A) | 3.71 | 39.5 |
| C225v5-3954-1004-LL | 1.51 | 16.1 |
| C225v5-3954-1001-LL | 3.83 | 40.7 |
| C225v5-3954-4001-LL | 15.8 | 168 |
| C225v5-3954-4001-SL | 32.9 | 350 |
| C225v5 parental antibody (FIG. 2B) | 0.082 | 1 |
| C225v5-3954-2001 (FIG. 2B) | 3.23 | 39.4 |
| C225v5-3954-4006-LL | 6.12 | 74.6 |
| C225v5-3954-4008-SL | 22.2 | 271 |
| C225v5-3954-4007-SL | 22.6 | 276 |
| C225v5-3954-1005-LL | 36.6 | 446 |

Example 5: In Vivo Efficacy of Anti-EGFR Activatable Antibodies

The studies provided herein evaluate the in vivo efficacy of activatable antibodies that include matrix metalloprotease (MMP) substrates of the present disclosure using a mouse H292 (human lung cancer cell line) xenograft model.

Figure 3A:
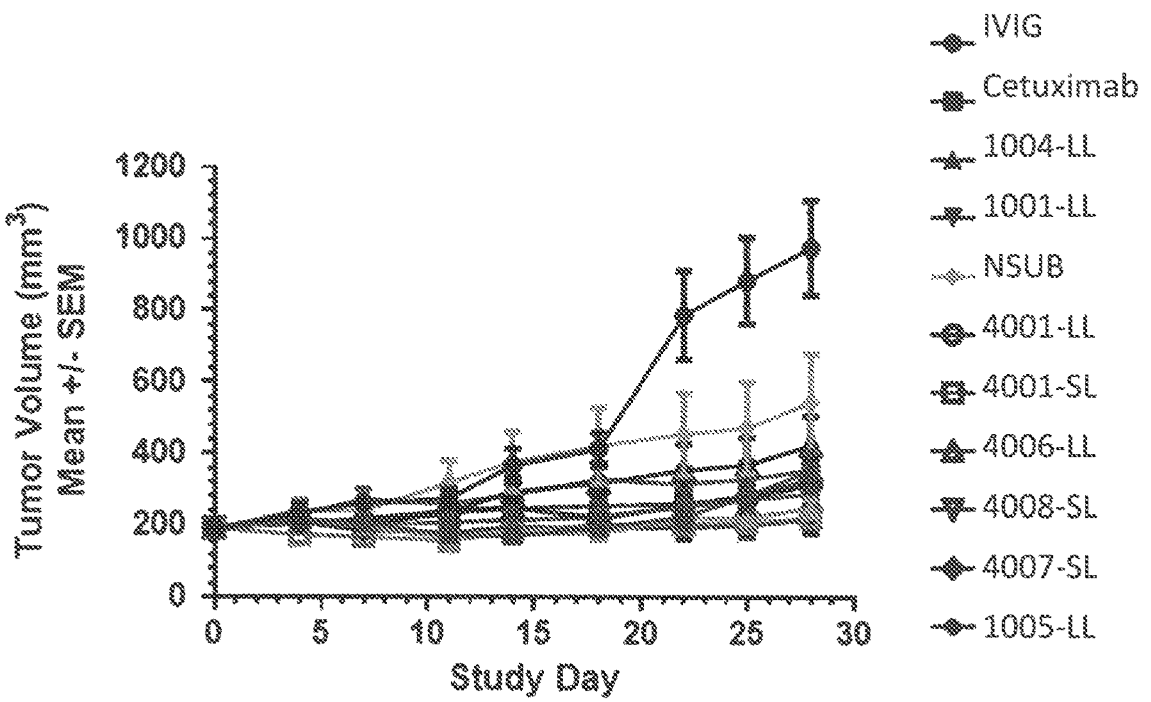
FIGS. 3A and 3B are graphs showing exemplary results of the in vivo efficacy of the indicated activatable anti-EGFR antibodies of the present disclosure using a mouse H292 xenograft model. These exemplary results showed that activatable antibodies with certain MMP substrates of the present disclosure showed efficacy in this xenograft model that was comparable to unmasked anti-EGFR cetuximab.
Figure 3B:
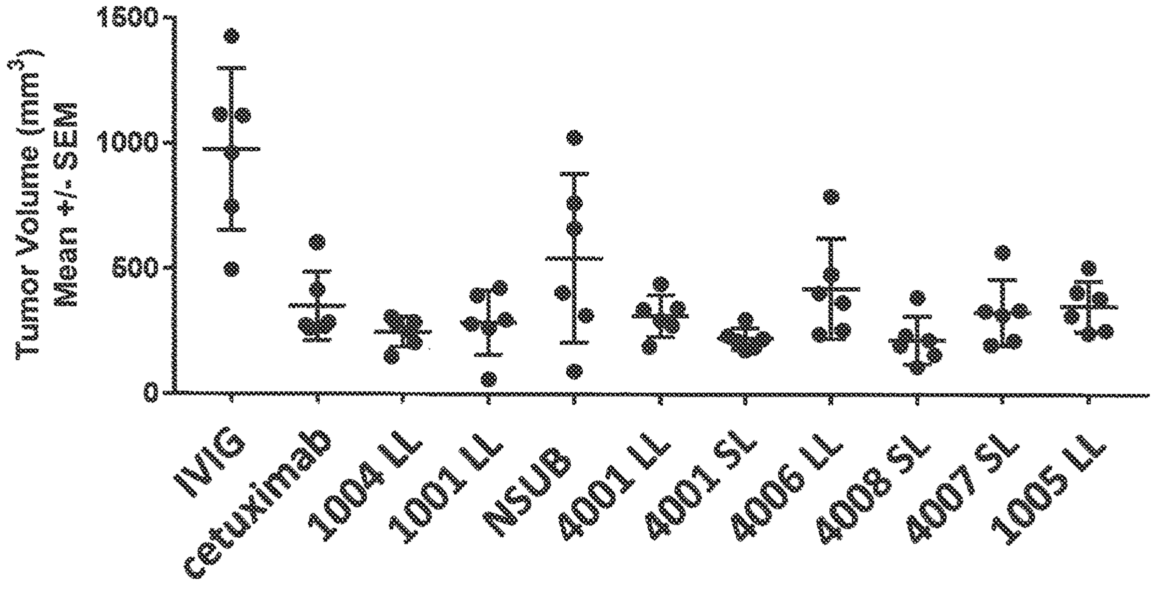

In these studies, H292 (human lung cancer-derived cell line) subcutaneous xenograft tumors in female nu/nu mice of 6-8 weeks of age were grown to an average volume of 180-260 $mm^3$. The H292 cell line is responsive to the anti-EGFR antibody cetuximab. The mice were then randomized into groups of 7 mice each and each group was dosed intraperitoneally on day 1 with 10 mg/kg of the indicated test article. The mean tumor volume±SEM was plotted for each time point following administration of the test article, as shown in FIG. 3A. FIG. 3B shows the distribution of absolute tumor volumes at day 28 for each mouse treated with activated antibodies with the indicated substrates, or with cetuximab or immunoglobulin (IVIG) control. The efficacy was determined with activatable antibodies that having known substrates e.g. 1001 (ISSGLLSS), 1004 (AVGLLAPP), and 1005 (GPSHLVLT) that includes at least one MMP substrate, or with an uncleavable glycine-serine linker (NSUB).

As shown in FIGS. 3A and 3B, certain of the activatable antibodies with MMP substrates of the present disclosure demonstrated an in vivo efficacy that was comparable with cetuximab, which lacks a prodomain.

Example 6: In Vivo Intra-Tumoral Activation of Anti-EGFR Activatable Antibodies

The studies provided herein evaluate the in vivo intratumoral activation of activatable antibodies that include matrix metalloprotease (MMP) substrates of the present disclosure following administration to a mouse H292 (human lung cancer cell line) xenograft model.

In these studies, H292 (human lung cancer-derived cell line) subcutaneous xenograft tumors in female nu/nu mice of 6-8 weeks of age were grown to an average volume of 180-260 $mm^3$. The H292 cell line is responsive to the anti-EGFR antibody cetuximab. The mice were then randomized into groups of 7 mice each and each group was dosed intraperitoneally on day 1 with 10 mg/kg of the indicated test article. Each mouse was treated with activated antibodies with the indicated substrates, or with cetuximab or immunoglobulin (IVIG) control. The efficacy was determined with activatable antibodies that having known substrates e.g. 1001 (ISSGLLSS, SEQ ID NO: 17), 1004 (AVGLLAPP, SEQ ID NO: 18), and 1005 (GPSHLVLT, SEQ ID NO: 19) that includes at least one MMP substrate, or with an uncleavable glycine-serine linker (NSUB).

Figure 4:
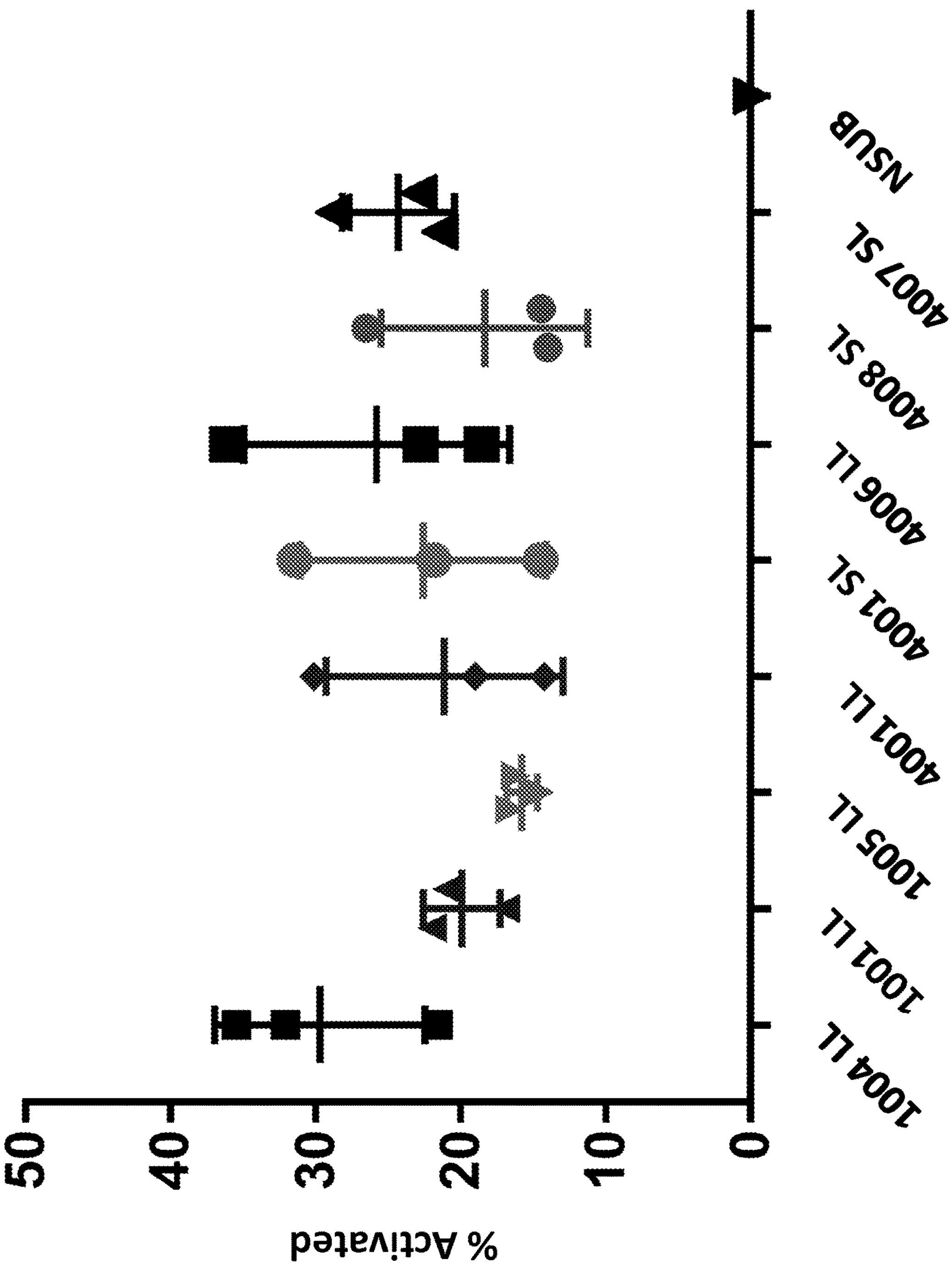
FIG. 4 is a graph showing exemplary results of the percent of the indicated activatable anti-EGFR antibodies of the present disclosure that were activated within intra-tumoral tissue following administration to a mouse H292 xenograft model.
Figure 5:
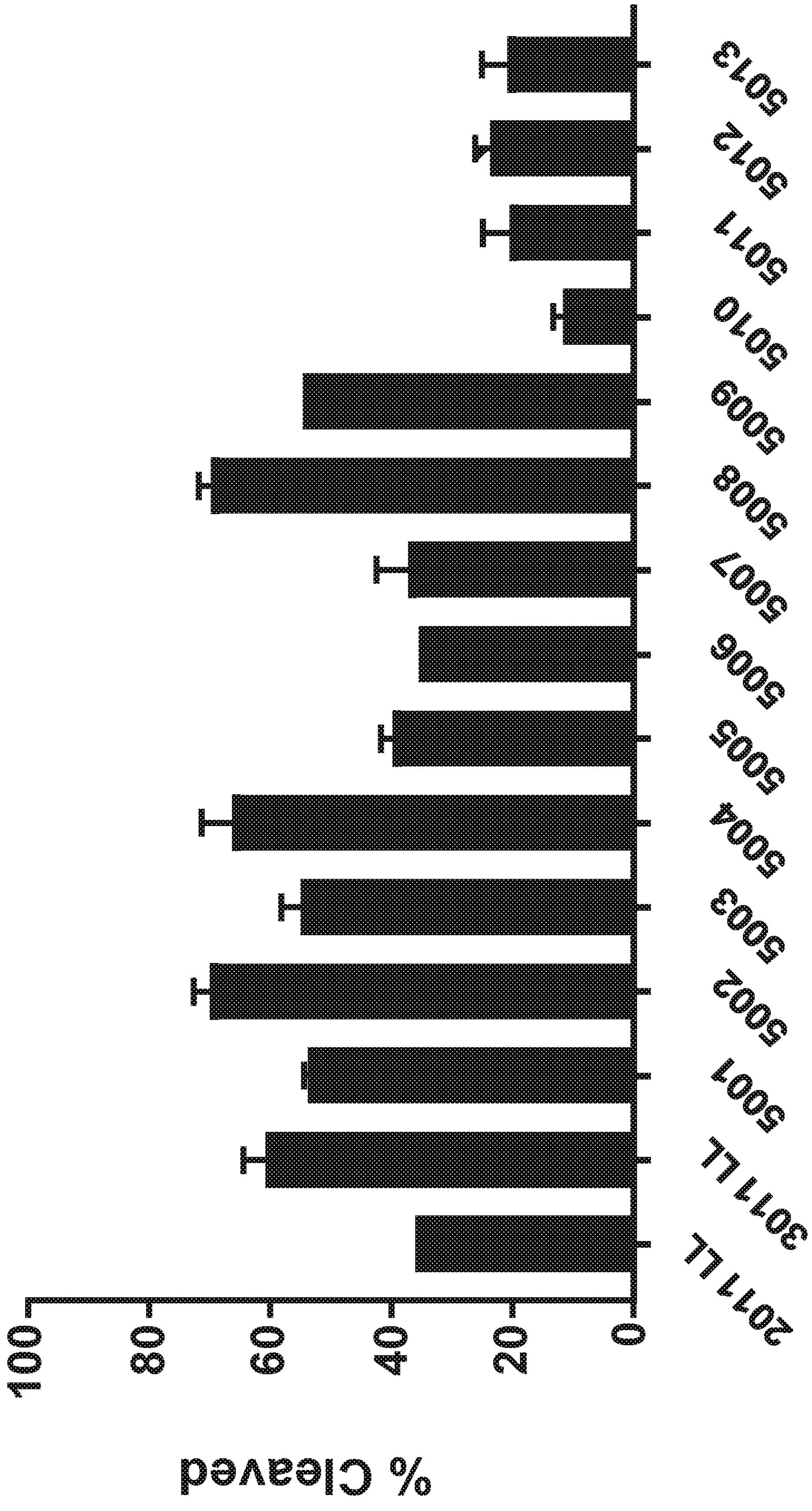
FIG. 5 is a graph showing exemplary results of the percent of the indicated activatable anti-EGFR antibodies with single MMP or tandem substrates of the present disclosure that were observed to be cleaved in vivo following their administration to nu/nu mice. These exemplary results showed that several of the tested activatable antibodies with tandem substrates showed a higher degree of in vivo stability than other substrates that are cleavable by multiple enzymes.

Tumors and plasma were collected from the mice 4 days after dosing. The tumor tissue was lysed with immunoprecipitation buffer (Pierce) containing HALT protease inhibitor cocktail (Thermo Fisher) and EDTA and lysed using the Barocycler (Pressure Bioscience). The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 6 and FIG. 4.

A summary of the properties of certain activatable antibodies with MMP substrates of the present disclosure is shown in Table 6. The in vivo stability of the indicated test articles from Example 3, Table 4 are presented are comparison. These exemplary results show the MMP substrate 4001 demonstrated desirable properties, including cleavability by both MMP9 and MMP14. Some substrates also showed a higher relative stability than other reference MMP substrates (1001 and 1004).

These exemplary results also show a group of substrates in which the in vivo non-tumor and/or intra-tumor stability is less than 30% activation. These exemplary results also show a group of substrates in which the in vivo non-tumor and/or intra-tumor stability is between 20% and 30% activation. These exemplary results also show a group of substrates in which the in vivo non-tumor and/or intra-tumor stability is between 22% and 27% activation. In some embodiments, such substrates may include isolated polypeptide that include the amino acid sequence of ALAHGLF (SEQ ID NO: 1), RGPKLYW (SEQ ID NO: 6), or RFPYGVW (SEQ ID NO: 7).

TABLE 6

Summary of MMP Substrate Characteristics

| Substrate | Substrate Sequence | Substrate SEQ ID NO | In Vivo Stability (Non-Tumor) | In Vivo Stability (Intra-Tumor) |
|---|---|---|---|---|
| 2001 | ISSGLLSGRSDNH | 23 | 30% | Not Tested |
| 4001-LL | ALAHGLF | 1 | 22% | 27% |
| 4001-SL | ALAHGLF | 1 | 27% | 25% |
| 4007-SL | RFPYGVW | 7 | N/A | 22% |
| 4006-LL | RGPKLYW | 6 | 23% | 26% |
| 4008-SL | HVPRQV | 8 | 18% | 14% |
| 1005-LL | GPSHLVLT | 19 | 11% | 16% |
| 1001-LL | ISSGLLSS | 17 | 20% | 20% |
| 1004-LL | AVGLLAPP | 18 | Not determined | 37% |

Example 7: Activatable Antibodies and Tandem Cleavable Substrates

The studies provided herein describe exemplary tandem substrates of the present disclosure that include at least one substrate cleavable by a matrix metalloprotease (MMP) substrates of the present disclosure and at least one substrate cleavable by a serine protease.

Exemplary activatable antibodies were constructed such that each one includes one of the tandem substrates listed in Table 7. The exemplary activatable antibodies of the present disclosure, the sequences of which are listed in Table 7, include an antibody or antigen binding fragment thereof (AB) that is based on a mouse/human chimeric monoclonal antibody that specifically binds to epidermal growth factor receptor (EGFR). The exemplary activatable antibodies also include a prodomain coupled to the N-terminus of the light chain of the AB. Each prodomain includes a masking moiety (MM) and a cleavable moiety (CM), and the CM includes at least one tandem substrate sequence of Table 7.

TABLE 7

Tandem MMP/Serine Protease Substrates

| Name | Sequence | SEQ ID NO: |
|---|---|---|
| 5001 | LSGRSALAHGLF | 25 |
| 5002 | ALAHGLFSGRSAN | 26 |
| 5003 | HVPRQVLSGRS | 27 |
| 5004 | HVPRQVLSGRSAN | 28 |
| 5005 | TARGPALAHGLF | 29 |
| 5006 | TARGPVPRQV | 30 |
| 5007 | APRSALAHGLF | 31 |
| 5008 | ALAHGLFAPRSF | 32 |
| 5009 | HVPRQVAPRSF | 33 |
| 5010 | ALAHGLPTFVHL | 34 |
| 5011 | GLPTFVHLPRQV | 35 |
| 5012 | AANALAHGLF | 36 |
| 5013 | GPTNALAHGLF | 37 |
| 5014 | ISSGLLSGRSNI | 38 |
| 5015 | AVGLLAPPGGLSGRSNI | 39 |
| 5016 | ISSGLLSGRSNIGS | 40 |
| 5017 | AVGLLAPPGGLSGRSNIGS | 41 |
| 5018 | ISSGLLSGRSNIG | 42 |
| 5019 | AVGLLAPPGGLSGRSNIG | 43 |

TABLE 7

| Activatable Antibody Sequences |
|---|
| Anti-EGFR Activatable Antibody (c225v5-3954-5001) Light Chain (amino acid sequence) (SEQ ID NO: 450)<br>QGQSGQCISPRGCPDGPYVMYGGGSSGGSLSGRSALAHGLFGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-5002) Light Chain (amino acid sequence) (SEQ ID NO: 451)<br>QGQSGQCISPRGCPDGPYVMYGGGSSGGSALAHGLFSGRSANGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |
| Anti-EGFR Activatable Antibody (c225v5-3954-5003) Light Chain (amino acid sequence) (SEQ ID NO: 452)<br>QGQSGQCISPRGCPDGPYVMYGGGSSGGSHVPRQVLSGRSGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-5004) Light Chain (amino acid sequence) (SEQ ID NO: 453)<br>QGQSGQCISPRGCPDGPYVMYGGGSSGGSHVPRQVLSGRSANGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |
| Anti-EGFR Activatable Antibody (c225v5-3954-5005) Light Chain (amino acid sequence) (SEQ ID NO: 454)<br>QGQSGQCISPRGCPDGPYVMYGGGSSGGSTARGPALAHGLFGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-5006) Light Chain (amino acid sequence) (SEQ ID NO: 455)<br>QGQSGQCISPRGCPDGPYVMYGGGSSGGSTARGPVPRQVGGGSQILLTQSPVILSVSPGERVSF<br>SCRASQSIGTNIHWYQQRTNGSPRLLIKYASESISGIPSRFSGSGSGTDFTLSINSVESEDIAD<br>YYCQQNNNWPTTFGAGTKLELKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQGLSSPVTKSFNRGE<br>C |
| Anti-EGFR Activatable Antibody (c225v5-3954-5007) Light Chain (amino acid sequence) (SEQ ID NO: 456)<br>QGQSGQCISPRGCPDGPYVMYGGGSSGGSAPRSALAHGLFGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-5008) Light Chain (amino acid sequence) (SEQ ID NO: 457)<br>QGQSGQCISPRGCPDGPYVMYGGGSSGGSALAHGLFAPRSFGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-5009) Light Chain (amino acid sequence) (SEQ ID NO: 458)<br>QGQSGQCISPRGCPDGPYVMYGGGSSGGSHVPRQVAPRSFGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |

TABLE 7-continued

| Activatable Antibody Sequences |
|---|
| Anti-EGFR Activatable Antibody (c225v5-3954-5010) Light Chain (amino acid sequence) (SEQ ID NO: 459)<br>QGQSGQCISPRGCPDGPYVMYGGGSSGGSALAHGLPTFVHLGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-5011) Light Chain (amino acid sequence) (SEQ ID NO: 460)<br>QGQSGQCISPRGCPDGPYVMYGGGSSGGSGLPTFVHLPRQVGGGSQILLTQSPVILSVSPGERV<br>SFSCRASQSIGTNIHWYQQRTNGSPRLLIKYASESISGIPSRFSGSGSGTDFTLSINSVESEDI<br>ADYYCQQNNNWPTTFGAGTKLELKRTVAAPSVFIFPPSDEQLKSGTASVVCLLNNFYPREAKVQ<br>WKVDNALQSGNSQESVTEQDSKDSTYSLSSTLTLSKADYEKHKVYACEVTHQGLSSPVTKSFNR<br>GEC |
| Anti-EGFR Activatable Antibody (c225v5-3954-5012) Light Chain (amino acid sequence) (SEQ ID NO: 461)<br>QGQSGQCISPRGCPDGPYVMYGGGSSGGSAANALAHGLFGGGSQILLTQSPVILSVSPGERVSF<br>SCRASQSIGTNIHWYQQRTNGSPRLLIKYASESISGIPSRFSGSGSGTDFTLSINSVESEDIAD<br>YYCQQNNNWPTTFGAGTKLELKRTVAAPSVFIFPPSDEQLKSGTASVVCLLNNFYPREAKVQWK<br>VDNALQSGNSQESVTEQDSKDSTYSLSSTLTLSKADYEKHKVYACEVTHQGLSSPVTKSFNRGE<br>C |
| Anti-EGFR Activatable Antibody (c225v5-3954-5013) Light Chain (amino acid sequence) (SEQ ID NO: 462)<br>QGQSGQCISPRGCPDGPYVMYGGGSSGGSGPTNALAHGLFGGGSQILLTQSPVILSVSPGERVS<br>FSCRASQSIGTNIHWYQQRTNGSPRLLIKYASESISGIPSRFSGSGSGTDFTLSINSVESEDIA<br>DYYCQQNNNWPTTFGAGTKLELKRTVAAPSVFIFPPSDEQLKSGTASVVCLLNNFYPREAKVQW<br>KVDNALQSGNSQESVTEQDSKDSTYSLSSTLTLSKADYEKHKVYACEVTHQGLSSPVTKSFNRG<br>EC |
| Anti-EGFR Activatable Antibody (c225v5-3954-2001) Light Chain (amino acid sequence) (SEQ ID NO: 488)<br>QGQSGQCISPRGCPDGPYVMYGGGSSGGSISSGLLSGRSDNHGSSGTQILLTQSPVILSVSPGE<br>RVSFSCRASQSIGTNIHWYQQRTNGSPRLLIKYASESISGIPSRFSGSGSGTDFTLSINSVESE<br>DIADYYCQQNNNWPTTFGAGTKLELKRTVAAPSVFIFPPSDEQLKSGTASVVCLLNNFYPREAK<br>VQWKVDNALQSGNSQESVTEQDSKDSTYSLSSTLTLSKADYEKHKVYACEVTHQGLSSPVTKSF<br>NRGEC |
| Anti-EGFR Activatable Antibody (c225v5-3954-2001TT) Light Chain (amino acid sequence) (SEQ ID NO: 489)<br>QGQSGQCISPRGCPDGPYVMYGGGSSGGSISSGLLSGRSDNHGGGSQILLTQSPVILSVSPGER<br>VSFSCRASQSIGTNIHWYQQRTNGSPRLLIKYASESISGIPSRFSGSGSGTDFTLSINSVESED<br>IADYYCQQNNNWPTTFGAGTKLELKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGLSSPVTKSFN<br>RGEC |
| Anti-EGFR Activatable Antibody (c225v5-3954-3001) Light Chain (amino acid sequence) (SEQ ID NO: 490)<br>QGQSGQCISPRGCPDGPYVMYGGGSSGGSAVGLLAPPGGLSGRSDNHGGGSQILLTQSPVILSV<br>SPGERVSFSCRASQSIGTNIHWYQQRTNGSPRLLIKYASESISGIPSRFSGSGSGTDFTLSINS<br>VESEDIADYYCQQNNNWPTTFGAGTKLELKRTVAAPSVFIFPPSDEQLKSGTASVVCLLNNFYP<br>REAKVQWKVDNALQSGNSQESVTEQDSKDSTYSLSSTLTLSKADYEKHKVYACEVTHQGLSSPV<br>TKSFNRGEC |

Example 8: In Vitro Stability of Activatable Antibodies with Tandem Substrates The studies provided herein evaluate the in vitro stability of activatable antibodies containing exemplary tandem substrates of the present disclosure that include at least one substrate cleavable by a matrix metalloprotease (MMP) substrates and at least one substrate cleavable by a serine protease.

The stability of the activatable antibodies of the present disclosure were measured by in the presence of the indicated recombinant proteases (matriptase, legumain, neutrophil elastase, MMP2, MMP9, and MMP14). Each activatable antibody (250 nM/38.5 μg/mL) was incubated with 10 mM of the indicated protease for 24 hours at 37° C., and the fraction of the activatable antibody that was cleaved was measured by capillary electrophoresis for each protease enzyme. The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The exemplary results of this in vitro study are summarized in Table 8A.

In addition, an exemplary study to determine the cleavability kinetics (i.e., Kcat/Km ($M^{-1}$ $s^{-1}$)) of the indicated substrates of the present disclosure with the indicated protease enzymes. The exemplary results of this in vitro study are summarized in Table 8A.

These exemplary results show that the substrates of the present disclosure showed a range of cleavability by the indicated proteases.

These exemplary results show that the tandem substrates of the present disclosure showed a range of cleavability by matriptase, MMP9, MMP14, legumain, and/or neutrophil elastase enzymes. These exemplary results also show a group of substrates in which the MMP9 and MMP14 cleavability are both at least 30%. In some embodiments, such substrates may include isolated polypeptide that include the amino acid sequence of LSGRSALAHGLF (SEQ ID NO: 25), ALAHGLFSGRSAN (SEQ ID NO: 26), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 50%. In some embodiments, such substrates may include isolated polypeptide that include the amino acid sequence of LSGRSALAHGLF (SEQ ID NO: 25), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 70%. In some embodiments, such substrates may include isolated polypeptide that include the amino acid sequence of LSGRSALAHGLF (SEQ ID NO: 25) or APRSALAHGLF (SEQ ID NO: 31).

These exemplary results also show a group of substrates in which the MMP9 and MMP14 cleavability are both at least 15% and the matriptase cleavability is at least 50%. In some embodiments, such substrates may include isolated polypeptide that include the amino acid sequence of LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), APRSALAHGLF (SEQ ID NO: 31), or ALAHGLFAPRSF (SEQ ID NO: 32).

These exemplary results also show a group of substrates in which the MMP9 and MMP14 cleavability are both at least 15% and the neutrophil elastase cleavability is at least 30%. In some embodiments, such substrates may include isolated polypeptide that include the amino acid sequence of LSGRSALAHGLF (SEQ ID NO: 25), ALAHGLFSGRSAN (SEQ ID NO: 26), HVPRQVLSGRS (SEQ ID NO: 27), HVPRQVLSGRSAN (SEQ ID NO: 28), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 30% and the neutrophil elastase cleavability is at least 30%. In some embodiments, such substrates may include isolated polypeptide that include the amino acid sequence of LSGRSALAHGLF (SEQ ID NO: 25), ALAHGLFSGRSAN (SEQ ID NO: 26), TARGPALAHGLF (SEQ ID NO: 29), APRSALAHGLF (SEQ ID NO: 31), ALAHGLFAPRSF (SEQ ID NO: 32), AANALAHGLF (SEQ ID NO: 36), or GPTNALAHGLF (SEQ ID NO. 37).

These exemplary results also show a group of substrates in which the MMP9 and MMP14 cleavability are both at least 50% and the neutrophil elastase cleavability is at least 50%. In some embodiments, such substrates may include isolated polypeptide that include the amino acid sequence of LSGRSALAHGLF (SEQ ID NO: 25), APRSALAHGLF (SEQ ID NO: 31), ALAHGLFAPRSF (SEQ ID NO: 32), AANALAHGLF (SEQ ID NO: 36), or GPTNALAHGLF (SEQ ID NO: 37).

These exemplary results also show a group of substrates in which the MMP9 and MMP14 cleavability are both at least 70% and the neutrophil elastase cleavability is at least 70%. In some embodiments, such substrates may include isolated polypeptide that include the amino acid sequence of LSGRSALAHGLF (SEQ ID NO: 25) or APRSALAHGLF (SEQ ID NO: 31).

TABLE 8A

In Vitro Activation of Activatable Antibodies with Tandem Substrates

| Substrate of Activatable Antibody | Substrate (SEQ ID NO) | Cleavability (%) | | | | |
|---|---|---|---|---|---|---|
| | | Matriptase | MMP14 | MMP9 | Legumain | Neutrophil Elastase |
| 2001 | ISSGLLSGRSDNH (23) | 53 | 58 | 22 | 5 | 18 |
| 3001 | AVGLLAPPGGLSGRSDNH (24) | NT | NT | NT | 0 | 52 |
| 4001 | ALAHGLF (1) | 0 | 77 | 100 | 0 | 37 |
| 4008 | HVPRQV (8) | 40 | 6 | 100 | 0 | 28 |
| 5001 | LSGRSALAHGLF (25) | 100 | 76 | 76 | 0 | 88 |
| 5002 | ALAHGLFSGRSAN (26) | 100 | 58 | 37 | 21 | 67 |
| 5003 | HVPRQVLSGRS (27) | 99 | 20 | 100 | 0 | 77 |
| 5004 | HVPRQVLSGRSAN (28) | 75 | 19 | 86 | 27 | 84 |

TABLE 8A-continued

In Vitro Activation of Activatable Antibodies with Tandem Substrates

| Substrate of Activatable Antibody | Substrate (SEQ ID NO) | Cleavability (%) Matriptase | MMP14 | MMP9 | Legumain | Neutrophil Elastase |
|---|---|---|---|---|---|---|
| 5005 | TARGPALAHGLF (29) | 6 | 34 | 72 | 0 | 81 |
| 5006 | TARGPVPRQV (30) | 100 | 6 | 81 | 0 | 30 |
| 5007 | APRSALAHGLF (31) | 100 | 90 | 77 | 0 | 74 |
| 5008 | ALAHGLFAPRSF (32) | 98 | 55 | 100 | 0 | 66 |
| 5009 | HVPRQVAPRSF (33) | 100 | 9 | 78 | 0 | 31 |
| 5010 | ALAHGLPTFVHL (34) | 0 | 11 | 0 | 0 | 100 |
| 5011 | GLPTFVHLPRQV (35) | 80 | 7 | 55 | 0 | 100 |
| 5012 | AANALAHGLF (36) | 0 | 72 | 52 | 7 | 55 |
| 5013 | GPTNALAHGLF (37) | 0 | 78 | 62 | 9 | 56 |

NT = not tested

TABLE 8B

In Vitro Activation of Activatable Antibodies with Tandem Substrates

| Substrate of Activatable Antibody | Substrate (SEQ ID NO) | Kcat / Km ($M^{-1}$ $s^{-1}$) Matriptase | MMP14 | MMP9 | MMP2 | Neutrophil Elastase |
|---|---|---|---|---|---|---|
| 2001 | ISSGLLSGRSDNH (23) | 2.55 E+03 | 6.33 E+03 | 3.94 E+02 | 1.32 E+04 | 3.17 E+03 |
| 3001 | AVGLLAPPGGLSGRSDNH (24) | 5.35 E+03 | 1.70 E+04 | 5.05 E+04 | 3.10 E+05 | 1.91 E+04 |
| 4001 | ALAHGLF (1) | 0.00 E+00 | 6.01 E+03 | 8.84 E+03 | 5.76 E+04 | N/D |
| 5007 | APRSALAHGLF (31) | 2.72 E+04 | 9.25 E+03 | 2.53 E+04 | 9.83 E+04 | 2.42 E+04 |
| 5013 | GPTNALAHGLF (37) | 0.00 | 7.77 E+03 | 1.04 E+04 | 7.65 E+04 | N/D |
| 4008 | HVPRQV (8) | 4.76 E+02 | 2.30 E+02 | 1.87 E+04 | 1.30 E+04 | N/D |
| 5006 | TARGPVPRQV (30) | 5.37 E+03 | 5.64 E+02 | 3.39 E+04 | 3.69 E+04 | N/D |
| 5011 | GLPTFVHLPRQV (35) | 1.43 E+03 | 4.44 E+02 | 4.18 E+03 | 3.38 E+03 | 6.65 E+05 |

N/D = not determined

Example 9: In Vivo Efficacy of Anti-EGFR Activatable Antibodies with Tandem Substrates The studies provided herein evaluate the in vivo efficacy of activatable antibodies of the present disclosure that include matrix metalloprotease (MMP) substrates and at least one serine protease substrate using a mouse H292 (human lung cancer cell line) xenograft model.

Figure 6:
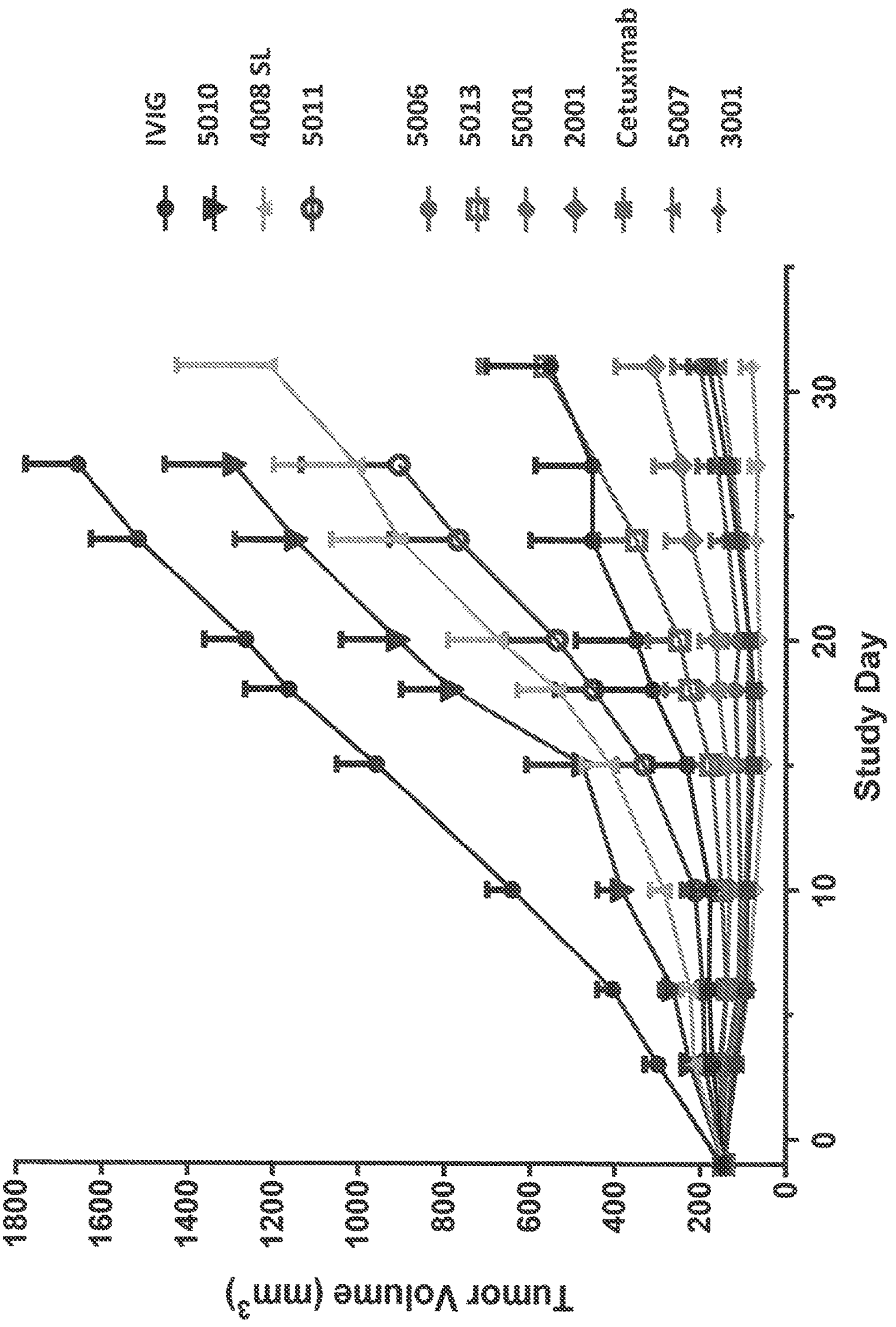
FIG. 6 is a graph showing exemplary results of the in vivo efficacy of the indicated activatable anti-EGFR antibodies of the present disclosure using a mouse H292 xenograft model. These exemplary results showed that activatable antibodies with certain MMP substrates of the present disclosure showed efficacy in this xenograft model that was comparable to unmasked anti-EGFR cetuximab antibody.

In these studies, H292 (human lung cancer-derived cell line) subcutaneous xenograft tumors in female nu/nu mice of 6-8 weeks of age were grown to an average volume of 180-260 $mm^3$. The H292 cell line is responsive to the anti-EGFR antibody cetuximab. The mice were then randomized into groups of 7 mice each and each group was dosed intraperitoneally on day 1 with 12.5 mg/kg of the indicated test article. The mean tumor volume t SEM was plotted for each time point following administration of the test article, as shown in FIG. 6. Each mouse was treated with activated antibodies with the indicated substrates, or with cetuximab or immunoglobulin (IVIG) control. The efficacy was determined with activatable antibodies that having known substrates e.g. 2001 (ISSGLLSGRSDNH) and 3001 (AVGLLAPPGGLSGRSDNH).

Figure 7:
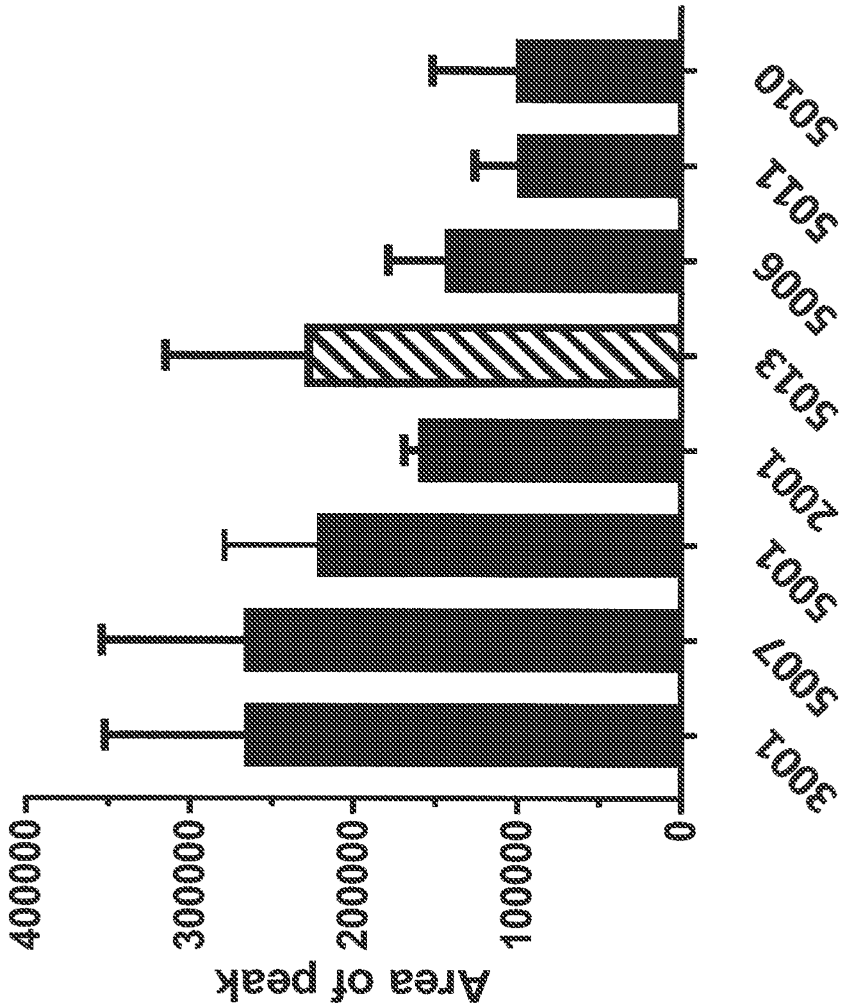
FIG. 7 is a graph showing exemplary results of the percent of the indicated activatable anti-EGFR antibodies of the present disclosure that were activated within intra-tumoral tissue following administration to a mouse H292 xenograft model.

In addition to the in vivo stability assay, and intra-tumoral assay was performed using the indicated activatable antibodies as shown in FIG. 7. Tumors and plasma were collected from the mice 4 days after dosing. The tumor tissue was lysed with immunoprecipitation buffer (Pierce) containing HALT protease inhibitor cocktail (Thermo Fisher) and EDTA and lysed using the Barocycler (Pressure Bioscience). The sample was analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in FIG. 7.

As shown in FIGS. 6, certain of the activatable antibodies with tandem MMP and serine protease substrates of the present disclosure demonstrated an in vivo efficacy that was comparable with cetuximab, which lacks a prodomain.

Example 10: Masking Efficiency of Activatable Antibodies with Tandem Substrates

The studies provided herein evaluate the in vitro masking efficiency of activatable antibodies of the present disclose that include tandem matrix metalloprotease (MMP) and serine protease substrates.

Figure 8:
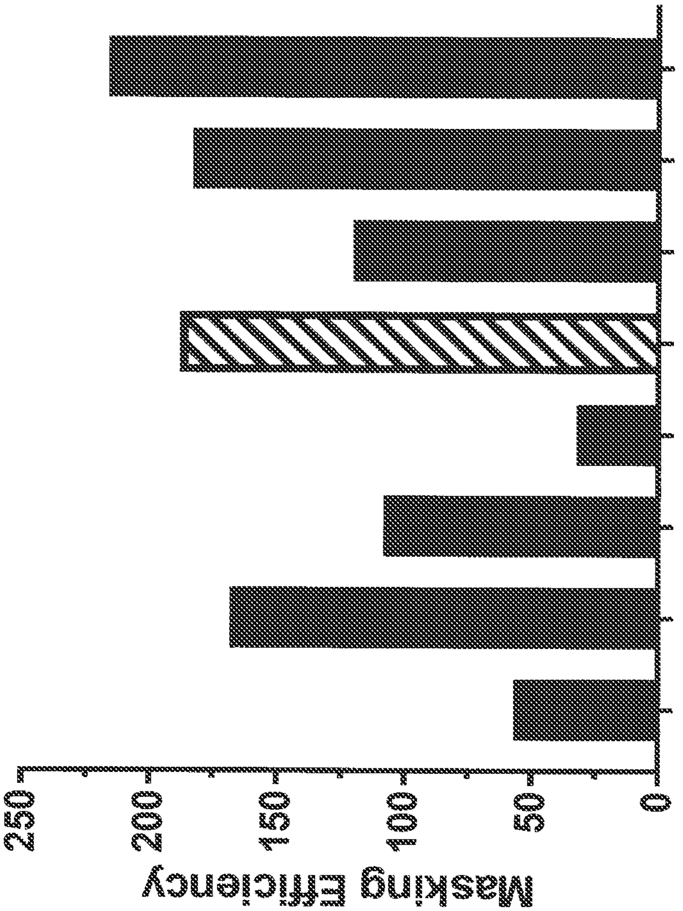
FIG. 8 is a graph showing exemplary results of the calculated masking efficiency calculated from the in vitro binding to EGFR of the indicated anti-EGFR activatable antibodies of the present disclosure. These exemplary results showed that the tandem substrates effected the masking efficiency of the prodomain of the activatable antibody.

In these studies, a solid-phase binding assay (ELISA) was used to demonstrate the binding affinity of anti-EGFR activatable antibodies that include MMP substrates of the present disclosure to recombinant EGFR. The binding affinity to EGFR of the activatable antibodies with the indicated substrate of the present disclosure was measured and compared to the c225v5 parental antibody. A summary of these exemplary results is shown in Table 9 and FIG. 8.

These exemplary results showed that the tandem substrates had an effect by increasing the apparent masking efficiency of the masking moiety in the activatable antibody.

TABLE 9

In Vitro Binding Activity and Masking Efficiency of Activatable Antibodies

| Test Article | $K_{Da}$ in nM (Std. Err) | Masking Efficiency |
|---|---|---|
| C225v5 parental antibody | 0.1585 (0.01978) | 1 |
| C225v5-3954-2001 | 5.062 (0.8141) | 32 |
| C225v5-3954-3001 | 9.095 (1.598) | 57 |
| C225v5-3954-4008 | 32.11 (6.39) | 203 |
| C225v5-3954-5007 | 26.61 (3.946) | 168 |
| C225v5-3954-5006 | 19.08 (3.15) | 120 |
| C225v5-3954-5013 | 29.85 (4.287) | 188 |
| C225v5-3954-5010 | 34.26 (4.212) | 216 |
| C225v5-3954-5011 | 29.03 (2.524) | 183 |
| C225v5-3954-5001 | 17.13 (2.538) | 108 |

Example 11: In Vivo Stability of Activatable Antibodies with Tandem Substrates

The studies provided herein evaluate the in vivo stability of activatable antibodies containing exemplary tandem substrates of the present disclosure that include at least one substrate cleavable by a matrix metalloprotease (MMP) and at least one substrate cleavable by a serine and/or cysteine protease.

These exemplary studies measured the stability of activatable antibodies containing MMP substrates of the present disclosure by administering a dose of the activatable antibodies to mice, and then measuring by Western blot the fraction of the activatable antibody in plasma that was observed to be cleaved. The stability was compared to other known activatable antibodies that have substrates e.g. 2001 (ISSGLLSGRSDNH), and 3001 (AVGLLAPPGGLSGRSDNH) that include at least one MMP substrate and at least serine protease substrate.

In this study, nu/nu mice of about 7-8 weeks of age were administered intraperitoneally with the indicated test article at a dosage I'm of 12.5 mg/kg. After 7 days following the administration, terminal blood was collected by cardiac puncture and processed to plasma within 1 hour of collection. The collected sample was diluted 1:100 in phosphate-buffered saline solution and denatured and analyzed using the WES Western Blot protocol (Protein Simple) using A110UK goat anti-human IgG antibodies (American Qualex) and anti-goat secondary antibodies (Jackson ImmunoResearch). The fraction of cleaved activatable antibody was determined by quantifying the fraction of the higher mobility polypeptide corresponding to the cleaved activatable antibody. The results of these exemplary assays are summarized in Table 10.

These exemplary results showed that certain activatable antibodies that include tandem substrates of the present disclosure demonstrated a higher in vivo stability than activatable antibodies with both serine protease and MMP substrates.

TABLE 10

In Vivo Stability of Activatable Antibodies with Tandem Substrates

| Activatable Antibody | Substrate | Substrate SEQ ID NO | % cleaved |
|---|---|---|---|
| c225v5-3954-2001 | ISSGLLSGRSDNH | 23 | 36% (DNP) |
| c225v5-3954-4001 | ALAHGLF | 1 | 27% |

TABLE 10-continued

In Vivo Stability of Activatable Antibodies with Tandem Substrates

| Activatable Antibody | Substrate | Substrate SEQ ID NO | % cleaved |
|---|---|---|---|
| c225v5-3954-4008 | HVPRQV | 8 | 18% |
| c225v5-3954-5001 | LSGRSALAHGLF | 25 | 54% |
| c225v5-3954-5002 | ALAHGLFSGRSAN | 26 | 70% |
| c225v5-3954-5003 | HVPRQVLSGRS | 27 | 55% |
| c225v5-3954-5004 | HVPRQVLSGRSAN | 28 | 65% |
| c225v5-3954-5005 | TARGPALAHGLF | 29 | 40% |
| c225v5-3954-5006 | TARGPVPRQV | 30 | 36% |
| c225v5-3954-5007 | APRSALAHGLF | 31 | 37% |
| c225v5-3954-5008 | ALAHGLFAPRSF | 32 | 70% |
| c225v5-3954-5009 | HVPRQVAPRSF | 33 | 55% |
| c225v5-3954-5010 | ALAHGLPTFVHL | 34 | 12% |
| c225v5-3954-5011 | GLPTFVHLPRQV | 35 | 21% |
| c225v5-3954-5012 | AANALAHGLF | 36 | 24% |
| c225v5-3954-5013 | GPTNALAHGLF | 37 | 21% |

Example 12: In Vivo Tumor Tissue Activation of Anti-EGFR Activatable Antibodies The studies provided herein evaluate the in vitro activation of activatable antibodies that include tandem substrates of the present disclosure by human tumor lysates.

Figure 9:
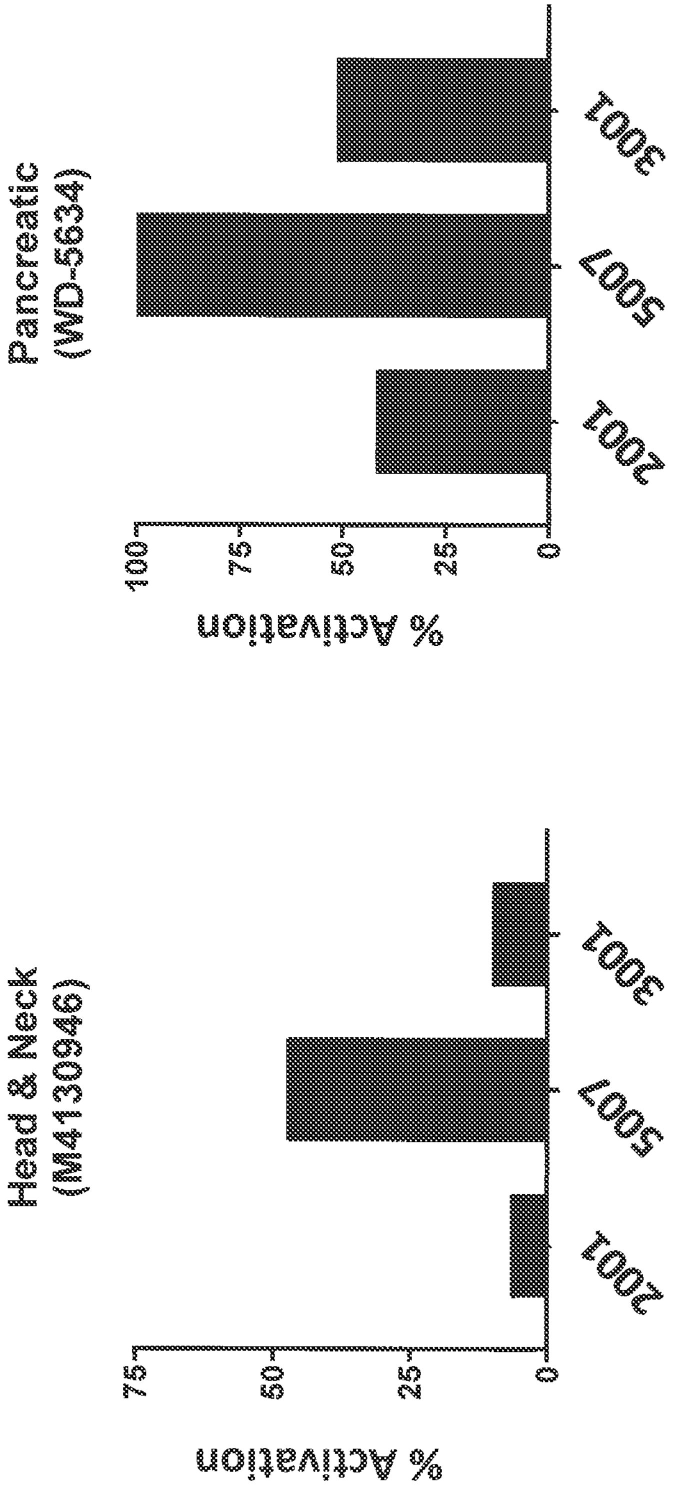
FIG. 9 is a graph showing exemplary results of the percent of the indicated activatable anti-EGFR antibodies of the present disclosure that were activated following incubation with human tumor tissue.

In these studies, human tumor tissues (head & neck cancer or pancreatic cancer) were incubated with anti-EGFR activatable antibodies with the substrates indicated in FIG. 9. The exemplary results showed that activatable antibodies with the 5007 substrate (APRSALAHGLF; SEQ ID NO: 31) showed a higher level of activation compared to activatable antibodies having the tandem substrate 2001 (ISSGLLSGRSDNH; SEQ ID NO: 23) or 3001 (AVGLLAPPGGLSGRSDNH; SEQ ID NO: 24).

In a further study, a similar activation study of activatable antibodies with the 5007 tandem substrate of the present invention (APRSALAHGLF; SEQ ID NO: 31) with head and neck tumor tissue or pancreatic tumor tissue were performed with a class-specific protease inhibitor selected from galardin, EDTA, aprotinin, or sivelestat. The studies showed that aprotinin, which is a broad-spectrum serine protease inhibitor, reduced the amount of activation to ≤5%. In comparison, treatment with the other three inhibitors showed activation at a level comparable to the non-inhibitor control study. These exemplary results showed that this activation was not inhibited by MMP (galardin, EDTA) or neutrophil elastase (sivelestat) inhibitors.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

We claim:

1. A cleavable polypeptide comprising a cleavable moiety (CM) comprising amino acid residues 11 to 17 of SEQ ID NO: 39, wherein the cleavable polypeptide further comprises an epitope that binds a target, and wherein the cleavable polypeptide further comprises a masking moiety (MM) that reduces binding of the epitope to the target.

2. The cleavable polypeptide of claim 1, wherein the CM comprises amino acid residues 10 to 17 of SEQ ID NO: 39.

3. A nucleic acid molecule encoding the cleavable polypeptide of claim 1.

4. A vector comprising the nucleic acid molecule of claim 3.

5. A method of producing a cleavable moiety (CM) containing polypeptide by culturing a cell under conditions that lead to expression of the polypeptide, wherein the cell comprises the vector of claim 4.

6. A method of manufacturing a cleavable moiety (CM) containing polypeptide, the method comprising:

(a) culturing a cell comprising a nucleic acid construct that encodes the cleavable polypeptide of claim 1 to express the cleavable polypeptide, and (b) recovering the cleavable polypeptide.

7. A nucleic acid molecule encoding the cleavable polypeptide of claim 2.

8. A vector comprising the nucleic acid molecule of claim 7.

9. A method of producing a cleavable moiety (CM) containing polypeptide by culturing a cell under conditions that lead to expression of the polypeptide, wherein the cell comprises the vector of claim 8.

10. A method of manufacturing a cleavable moiety (CM) containing polypeptide, the method comprising:

(a) culturing a cell comprising a nucleic acid construct that encodes the cleavable polypeptide of claim 2 to express the cleavable polypeptide, and (b) recovering the cleavable polypeptide.

11. A polypeptide comprising the cleavable polypeptide of claim 1 and an antibody or antigen binding fragment thereof (AB) that binds a target.

12. A polypeptide comprising the cleavable polypeptide of claim 2 and an antibody or antigen binding fragment thereof (AB) that binds a target.

13. The polypeptide of claim 11, wherein the antigen binding fragment thereof is selected from the group consisting of a Fab fragment, a $F(ab')_2$ fragment, a scFv, a scAb, a dAb, a single domain heavy chain antibody, and a single domain light chain antibody.

14. The polypeptide of claim 11, wherein the AB is linked to the CM.

15. The polypeptide of claim 11, wherein the AB is linked to the CM via a linking peptide.

16. A nucleic acid molecule encoding the polypeptide of claim 11.

17. A vector comprising the nucleic acid molecule of claim 16.

18. A method of producing a cleavable moiety (CM) containing polypeptide by culturing a cell under conditions that lead to expression of the polypeptide, wherein the cell comprises the vector of claim 17.

19. A method of manufacturing a cleavable moiety (CM) containing polypeptide, the method comprising:

(a) culturing a cell comprising a nucleic acid construct that encodes the cleavable polypeptide of claim 11 to express the polypeptide, and (b) recovering the polypeptide.

20. The cleavable polypeptide of claim 1, wherein the epitope that binds a target is an antigen-binding domain.

* * * * *

SEQUENCE LISTING

```
Sequence total quantity: 490
SEQ ID NO: 1            moltype = AA  length = 7
FEATURE                 Location/Qualifiers
source                  1..7
                        mol_type = protein
                        organism = synthetic construct
SEQUENCE: 1
ALAHGLF                                                              7

SEQ ID NO: 2            moltype = AA  length = 7
FEATURE                 Location/Qualifiers
source                  1..7
                        mol_type = protein
                        organism = synthetic construct
SEQUENCE: 2
DLAHPLL                                                              7

SEQ ID NO: 3            moltype = AA  length = 6
FEATURE                 Location/Qualifiers
source                  1..6
                        mol_type = protein
                        organism = synthetic construct
SEQUENCE: 3
AFRHLR                                                               6

SEQ ID NO: 4            moltype = AA  length = 6
FEATURE                 Location/Qualifiers
source                  1..6
                        mol_type = protein
                        organism = synthetic construct
SEQUENCE: 4
PHGFFQ                                                               6

SEQ ID NO: 5            moltype = AA  length = 6
```

-continued

```
FEATURE                 Location/Qualifiers
source                  1..6
                        mol_type = protein
                        organism = synthetic construct
SEQUENCE: 5
SVHHLI                                                          6

SEQ ID NO: 6            moltype = AA  length = 7
FEATURE                 Location/Qualifiers
source                  1..7
                        mol_type = protein
                        organism = synthetic construct
SEQUENCE: 6
RGPKLYW                                                         7

SEQ ID NO: 7            moltype = AA  length = 7
FEATURE                 Location/Qualifiers
source                  1..7
                        mol_type = protein
                        organism = synthetic construct
SEQUENCE: 7
RFPYGVW                                                         7

SEQ ID NO: 8            moltype = AA  length = 6
FEATURE                 Location/Qualifiers
source                  1..6
                        mol_type = protein
                        organism = synthetic construct
SEQUENCE: 8
HVPRQV                                                          6

SEQ ID NO: 9            moltype = AA  length = 6
FEATURE                 Location/Qualifiers
source                  1..6
                        mol_type = protein
                        organism = synthetic construct
SEQUENCE: 9
SNPFKY                                                          6

SEQ ID NO: 10           moltype = AA  length = 6
FEATURE                 Location/Qualifiers
source                  1..6
                        mol_type = protein
                        organism = synthetic construct
SEQUENCE: 10
RFPLKV                                                          6

SEQ ID NO: 11           moltype = AA  length = 6
FEATURE                 Location/Qualifiers
source                  1..6
                        mol_type = protein
                        organism = synthetic construct
SEQUENCE: 11
PFHLSR                                                          6

SEQ ID NO: 12           moltype = AA  length = 6
FEATURE                 Location/Qualifiers
source                  1..6
                        mol_type = protein
                        organism = synthetic construct
SEQUENCE: 12
STVFHM                                                          6

SEQ ID NO: 13           moltype = AA  length = 6
FEATURE                 Location/Qualifiers
source                  1..6
                        mol_type = protein
                        organism = synthetic construct
SEQUENCE: 13
MGPWFM                                                          6

SEQ ID NO: 14           moltype = AA  length = 6
FEATURE                 Location/Qualifiers
source                  1..6
                        mol_type = protein
                        organism = synthetic construct
SEQUENCE: 14
RHLAKL                                                          6
```

-continued

```
SEQ ID NO: 15           moltype = AA  length = 7
FEATURE                 Location/Qualifiers
source                  1..7
                        mol_type = protein
                        organism = synthetic construct
SEQUENCE: 15
PLGVRGK                                                          7

SEQ ID NO: 16           moltype = AA  length = 8
FEATURE                 Location/Qualifiers
source                  1..8
                        mol_type = protein
                        organism = synthetic construct
SEQUENCE: 16
QNQALRIA                                                         8

SEQ ID NO: 17           moltype = AA  length = 8
FEATURE                 Location/Qualifiers
source                  1..8
                        mol_type = protein
                        organism = synthetic construct
SEQUENCE: 17
ISSGLLSS                                                         8

SEQ ID NO: 18           moltype = AA  length = 8
FEATURE                 Location/Qualifiers
source                  1..8
                        mol_type = protein
                        organism = synthetic construct
SEQUENCE: 18
AVGLLAPP                                                         8

SEQ ID NO: 19           moltype = AA  length = 8
FEATURE                 Location/Qualifiers
source                  1..8
                        mol_type = protein
                        organism = synthetic construct
SEQUENCE: 19
GPSHLVLT                                                         8

SEQ ID NO: 20           moltype = AA  length = 8
FEATURE                 Location/Qualifiers
source                  1..8
                        mol_type = protein
                        organism = synthetic construct
SEQUENCE: 20
LSGRSDNH                                                         8

SEQ ID NO: 21           moltype = AA  length = 13
FEATURE                 Location/Qualifiers
source                  1..13
                        mol_type = protein
                        organism = synthetic construct
SEQUENCE: 21
ISSGLLSGRS DNP                                                   13

SEQ ID NO: 22           moltype = AA  length = 18
FEATURE                 Location/Qualifiers
source                  1..18
                        mol_type = protein
                        organism = synthetic construct
SEQUENCE: 22
AVGLLAPPGG LSGRSDNP                                              18

SEQ ID NO: 23           moltype = AA  length = 13
FEATURE                 Location/Qualifiers
source                  1..13
                        mol_type = protein
                        organism = synthetic construct
SEQUENCE: 23
ISSGLLSGRS DNH                                                   13

SEQ ID NO: 24           moltype = AA  length = 18
FEATURE                 Location/Qualifiers
source                  1..18
                        mol_type = protein
                        organism = synthetic construct
SEQUENCE: 24
AVGLLAPPGG LSGRSDNH                                              18
```

```
SEQ ID NO: 25          moltype = AA  length = 12
FEATURE                Location/Qualifiers
source                 1..12
                       mol_type = protein
                       organism = synthetic construct
SEQUENCE: 25
LSGRSALAHG LF                                                    12

SEQ ID NO: 26          moltype = AA  length = 13
FEATURE                Location/Qualifiers
source                 1..13
                       mol_type = protein
                       organism = synthetic construct
SEQUENCE: 26
ALAHGLFSGR SAN                                                   13

SEQ ID NO: 27          moltype = AA  length = 11
FEATURE                Location/Qualifiers
source                 1..11
                       mol_type = protein
                       organism = synthetic construct
SEQUENCE: 27
HVPRQVLSGR S                                                     11

SEQ ID NO: 28          moltype = AA  length = 13
FEATURE                Location/Qualifiers
source                 1..13
                       mol_type = protein
                       organism = synthetic construct
SEQUENCE: 28
HVPRQVLSGR SAN                                                   13

SEQ ID NO: 29          moltype = AA  length = 12
FEATURE                Location/Qualifiers
source                 1..12
                       mol_type = protein
                       organism = synthetic construct
SEQUENCE: 29
TARGPALAHG LF                                                    12

SEQ ID NO: 30          moltype = AA  length = 10
FEATURE                Location/Qualifiers
source                 1..10
                       mol_type = protein
                       organism = synthetic construct
SEQUENCE: 30
TARGPVPRQV                                                       10

SEQ ID NO: 31          moltype = AA  length = 11
FEATURE                Location/Qualifiers
source                 1..11
                       mol_type = protein
                       organism = synthetic construct
SEQUENCE: 31
APRSALAHGL F                                                     11

SEQ ID NO: 32          moltype = AA  length = 12
FEATURE                Location/Qualifiers
source                 1..12
                       mol_type = protein
                       organism = synthetic construct
SEQUENCE: 32
ALAHGLFAPR SF                                                    12

SEQ ID NO: 33          moltype = AA  length = 11
FEATURE                Location/Qualifiers
source                 1..11
                       mol_type = protein
                       organism = synthetic construct
SEQUENCE: 33
HVPRQVAPRS F                                                     11

SEQ ID NO: 34          moltype = AA  length = 12
FEATURE                Location/Qualifiers
source                 1..12
                       mol_type = protein
                       organism = synthetic construct
SEQUENCE: 34
```

```
ALAHGLPTFV HL                                                         12

SEQ ID NO: 35          moltype = AA  length = 12
FEATURE                Location/Qualifiers
source                 1..12
                       mol_type = protein
                       organism = synthetic construct
SEQUENCE: 35
GLPTFVHLPR QV                                                         12

SEQ ID NO: 36          moltype = AA  length = 10
FEATURE                Location/Qualifiers
source                 1..10
                       mol_type = protein
                       organism = synthetic construct
SEQUENCE: 36
AANALAHGLF                                                            10

SEQ ID NO: 37          moltype = AA  length = 11
FEATURE                Location/Qualifiers
source                 1..11
                       mol_type = protein
                       organism = synthetic construct
SEQUENCE: 37
GPTNALAHGL F                                                          11

SEQ ID NO: 38          moltype = AA  length = 12
FEATURE                Location/Qualifiers
source                 1..12
                       mol_type = protein
                       organism = synthetic construct
SEQUENCE: 38
ISSGLLSGRS NI                                                         12

SEQ ID NO: 39          moltype = AA  length = 17
FEATURE                Location/Qualifiers
source                 1..17
                       mol_type = protein
                       organism = synthetic construct
SEQUENCE: 39
AVGLLAPPGG LSGRSNI                                                    17

SEQ ID NO: 40          moltype = AA  length = 14
FEATURE                Location/Qualifiers
source                 1..14
                       mol_type = protein
                       organism = synthetic construct
SEQUENCE: 40
ISSGLLSGRS NIGS                                                       14

SEQ ID NO: 41          moltype = AA  length = 19
FEATURE                Location/Qualifiers
source                 1..19
                       mol_type = protein
                       organism = synthetic construct
SEQUENCE: 41
AVGLLAPPGG LSGRSNIGS                                                  19

SEQ ID NO: 42          moltype = AA  length = 13
FEATURE                Location/Qualifiers
source                 1..13
                       mol_type = protein
                       organism = synthetic construct
SEQUENCE: 42
ISSGLLSGRS NIG                                                        13

SEQ ID NO: 43          moltype = AA  length = 18
FEATURE                Location/Qualifiers
source                 1..18
                       mol_type = protein
                       organism = synthetic construct
SEQUENCE: 43
AVGLLAPPGG LSGRSNIG                                                   18

SEQ ID NO: 44          moltype =   length =
SEQUENCE: 44
000

SEQ ID NO: 45          moltype =   length =
```

```
SEQUENCE: 45
000

SEQ ID NO: 46           moltype =   length =
SEQUENCE: 46
000

SEQ ID NO: 47           moltype =   length =
SEQUENCE: 47
000

SEQ ID NO: 48           moltype =   length =
SEQUENCE: 48
000

SEQ ID NO: 49           moltype =   length =
SEQUENCE: 49
000

SEQ ID NO: 50           moltype = AA  length = 6
FEATURE                 Location/Qualifiers
source                  1..6
                        mol_type = protein
                        organism = synthetic construct
SEQUENCE: 50
LAHGLF                                                    6

SEQ ID NO: 51           moltype = AA  length = 5
FEATURE                 Location/Qualifiers
source                  1..5
                        mol_type = protein
                        organism = synthetic construct
SEQUENCE: 51
AHGLF                                                     5

SEQ ID NO: 52           moltype = AA  length = 6
FEATURE                 Location/Qualifiers
source                  1..6
                        mol_type = protein
                        organism = synthetic construct
SEQUENCE: 52
ALAHGL                                                    6

SEQ ID NO: 53           moltype = AA  length = 5
FEATURE                 Location/Qualifiers
source                  1..5
                        mol_type = protein
                        organism = synthetic construct
SEQUENCE: 53
LAHGL                                                     5

SEQ ID NO: 54           moltype = AA  length = 4
FEATURE                 Location/Qualifiers
source                  1..4
                        mol_type = protein
                        organism = synthetic construct
SEQUENCE: 54
AHGL                                                      4

SEQ ID NO: 55           moltype = AA  length = 5
FEATURE                 Location/Qualifiers
source                  1..5
                        mol_type = protein
                        organism = synthetic construct
SEQUENCE: 55
ALAHG                                                     5

SEQ ID NO: 56           moltype = AA  length = 4
FEATURE                 Location/Qualifiers
source                  1..4
                        mol_type = protein
                        organism = synthetic construct
SEQUENCE: 56
LAHG                                                      4

SEQ ID NO: 57           moltype =   length =
SEQUENCE: 57
000
```

-continued

```
SEQ ID NO: 58           moltype =   length =
SEQUENCE: 58
000

SEQ ID NO: 59           moltype =   length =
SEQUENCE: 59
000

SEQ ID NO: 60           moltype = AA  length = 5
FEATURE                 Location/Qualifiers
source                  1..5
                        mol_type = protein
                        organism = synthetic construct
SEQUENCE: 60
VPRQV                                                         5

SEQ ID NO: 61           moltype = AA  length = 4
FEATURE                 Location/Qualifiers
source                  1..4
                        mol_type = protein
                        organism = synthetic construct
SEQUENCE: 61
PRQV                                                          4

SEQ ID NO: 62           moltype = AA  length = 5
FEATURE                 Location/Qualifiers
source                  1..5
                        mol_type = protein
                        organism = synthetic construct
SEQUENCE: 62
HVPRQ                                                         5

SEQ ID NO: 63           moltype = AA  length = 4
FEATURE                 Location/Qualifiers
source                  1..4
                        mol_type = protein
                        organism = synthetic construct
SEQUENCE: 63
VPRQ                                                          4

SEQ ID NO: 64           moltype =   length =
SEQUENCE: 64
000

SEQ ID NO: 65           moltype =   length =
SEQUENCE: 65
000

SEQ ID NO: 66           moltype =   length =
SEQUENCE: 66
000

SEQ ID NO: 67           moltype =   length =
SEQUENCE: 67
000

SEQ ID NO: 68           moltype =   length =
SEQUENCE: 68
000

SEQ ID NO: 69           moltype =   length =
SEQUENCE: 69
000

SEQ ID NO: 70           moltype = AA  length = 7
FEATURE                 Location/Qualifiers
source                  1..7
                        mol_type = protein
                        organism = synthetic construct
SEQUENCE: 70
LSGRSDN                                                       7

SEQ ID NO: 71           moltype = AA  length = 6
FEATURE                 Location/Qualifiers
source                  1..6
                        mol_type = protein
                        organism = synthetic construct
SEQUENCE: 71
LSGRSD                                                        6
```

```
SEQ ID NO: 72           moltype = AA  length = 5
FEATURE                 Location/Qualifiers
source                  1..5
                        mol_type = protein
                        organism = synthetic construct
SEQUENCE: 72
LSGRS                                                                    5

SEQ ID NO: 73           moltype = AA  length = 4
FEATURE                 Location/Qualifiers
source                  1..4
                        mol_type = protein
                        organism = synthetic construct
SEQUENCE: 73
LSGR                                                                     4

SEQ ID NO: 74           moltype = AA  length = 6
FEATURE                 Location/Qualifiers
source                  1..6
                        mol_type = protein
                        organism = synthetic construct
SEQUENCE: 74
SGRSDN                                                                   6

SEQ ID NO: 75           moltype = AA  length = 5
FEATURE                 Location/Qualifiers
source                  1..5
                        mol_type = protein
                        organism = synthetic construct
SEQUENCE: 75
SGRSD                                                                    5

SEQ ID NO: 76           moltype = AA  length = 4
FEATURE                 Location/Qualifiers
source                  1..4
                        mol_type = protein
                        organism = synthetic construct
SEQUENCE: 76
SGRS                                                                     4

SEQ ID NO: 77           moltype =   length =
SEQUENCE: 77
000

SEQ ID NO: 78           moltype = AA  length = 8
FEATURE                 Location/Qualifiers
source                  1..8
                        mol_type = protein
                        organism = synthetic construct
SEQUENCE: 78
LSGRSGNH                                                                 8

SEQ ID NO: 79           moltype = AA  length = 7
FEATURE                 Location/Qualifiers
source                  1..7
                        mol_type = protein
                        organism = synthetic construct
SEQUENCE: 79
LSGRSGN                                                                  7

SEQ ID NO: 80           moltype = AA  length = 6
FEATURE                 Location/Qualifiers
source                  1..6
                        mol_type = protein
                        organism = synthetic construct
SEQUENCE: 80
LSGRSG                                                                   6

SEQ ID NO: 81           moltype = AA  length = 7
FEATURE                 Location/Qualifiers
source                  1..7
                        mol_type = protein
                        organism = synthetic construct
SEQUENCE: 81
SGRSGNH                                                                  7

SEQ ID NO: 82           moltype = AA  length = 6
FEATURE                 Location/Qualifiers
```

-continued

```
source                  1..6
                        mol_type = protein
                        organism = synthetic construct
SEQUENCE: 82
SGRSGN                                                                      6

SEQ ID NO: 83           moltype = AA  length = 5
FEATURE                 Location/Qualifiers
source                  1..5
                        mol_type = protein
                        organism = synthetic construct
SEQUENCE: 83
SGRSG                                                                       5

SEQ ID NO: 84           moltype = AA  length = 8
FEATURE                 Location/Qualifiers
source                  1..8
                        mol_type = protein
                        organism = synthetic construct
SEQUENCE: 84
LSGRSDNI                                                                    8

SEQ ID NO: 85           moltype = AA  length = 7
FEATURE                 Location/Qualifiers
source                  1..7
                        mol_type = protein
                        organism = synthetic construct
SEQUENCE: 85
SGRSDNI                                                                     7

SEQ ID NO: 86           moltype = AA  length = 8
FEATURE                 Location/Qualifiers
source                  1..8
                        mol_type = protein
                        organism = synthetic construct
SEQUENCE: 86
LSGRSDYH                                                                    8

SEQ ID NO: 87           moltype = AA  length = 7
FEATURE                 Location/Qualifiers
source                  1..7
                        mol_type = protein
                        organism = synthetic construct
SEQUENCE: 87
LSGRSDY                                                                     7

SEQ ID NO: 88           moltype = AA  length = 7
FEATURE                 Location/Qualifiers
source                  1..7
                        mol_type = protein
                        organism = synthetic construct
SEQUENCE: 88
SGRSDYH                                                                     7

SEQ ID NO: 89           moltype = AA  length = 6
FEATURE                 Location/Qualifiers
source                  1..6
                        mol_type = protein
                        organism = synthetic construct
SEQUENCE: 89
SGRSDY                                                                      6

SEQ ID NO: 90           moltype = AA  length = 8
FEATURE                 Location/Qualifiers
source                  1..8
                        mol_type = protein
                        organism = synthetic construct
SEQUENCE: 90
LSGRSDNP                                                                    8

SEQ ID NO: 91           moltype = AA  length = 7
FEATURE                 Location/Qualifiers
source                  1..7
                        mol_type = protein
                        organism = synthetic construct
SEQUENCE: 91
SGRSDNP                                                                     7

SEQ ID NO: 92           moltype = AA  length = 8
```

```
FEATURE                Location/Qualifiers
source                 1..8
                       mol_type = protein
                       organism = synthetic construct
SEQUENCE: 92
LSGRSDTH                                                    8

SEQ ID NO: 93          moltype = AA  length = 7
FEATURE                Location/Qualifiers
source                 1..7
                       mol_type = protein
                       organism = synthetic construct
SEQUENCE: 93
LSGRSDT                                                     7

SEQ ID NO: 94          moltype = AA  length = 7
FEATURE                Location/Qualifiers
source                 1..7
                       mol_type = protein
                       organism = synthetic construct
SEQUENCE: 94
SGRSDTH                                                     7

SEQ ID NO: 95          moltype = AA  length = 6
FEATURE                Location/Qualifiers
source                 1..6
                       mol_type = protein
                       organism = synthetic construct
SEQUENCE: 95
SGRSDT                                                      6

SEQ ID NO: 96          moltype = AA  length = 8
FEATURE                Location/Qualifiers
source                 1..8
                       mol_type = protein
                       organism = synthetic construct
SEQUENCE: 96
LSGRSDQH                                                    8

SEQ ID NO: 97          moltype = AA  length = 7
FEATURE                Location/Qualifiers
source                 1..7
                       mol_type = protein
                       organism = synthetic construct
SEQUENCE: 97
LSGRSDQ                                                     7

SEQ ID NO: 98          moltype = AA  length = 7
FEATURE                Location/Qualifiers
source                 1..7
                       mol_type = protein
                       organism = synthetic construct
SEQUENCE: 98
SGRSDQH                                                     7

SEQ ID NO: 99          moltype = AA  length = 6
FEATURE                Location/Qualifiers
source                 1..6
                       mol_type = protein
                       organism = synthetic construct
SEQUENCE: 99
SGRSDQ                                                      6

SEQ ID NO: 100         moltype = AA  length = 8
FEATURE                Location/Qualifiers
source                 1..8
                       mol_type = protein
                       organism = synthetic construct
SEQUENCE: 100
LSGRSDIH                                                    8

SEQ ID NO: 101         moltype = AA  length = 7
FEATURE                Location/Qualifiers
source                 1..7
                       mol_type = protein
                       organism = synthetic construct
SEQUENCE: 101
LSGRSDI                                                     7
```

-continued

```
SEQ ID NO: 102          moltype = AA  length = 7
FEATURE                 Location/Qualifiers
source                  1..7
                        mol_type = protein
                        organism = synthetic construct
SEQUENCE: 102
SGRSDIH                                                                    7

SEQ ID NO: 103          moltype = AA  length = 6
FEATURE                 Location/Qualifiers
source                  1..6
                        mol_type = protein
                        organism = synthetic construct
SEQUENCE: 103
SGRSDI                                                                     6

SEQ ID NO: 104          moltype = AA  length = 8
FEATURE                 Location/Qualifiers
source                  1..8
                        mol_type = protein
                        organism = synthetic construct
SEQUENCE: 104
LSGRSDDH                                                                   8

SEQ ID NO: 105          moltype = AA  length = 7
FEATURE                 Location/Qualifiers
source                  1..7
                        mol_type = protein
                        organism = synthetic construct
SEQUENCE: 105
LSGRSDD                                                                    7

SEQ ID NO: 106          moltype = AA  length = 7
FEATURE                 Location/Qualifiers
source                  1..7
                        mol_type = protein
                        organism = synthetic construct
SEQUENCE: 106
SGRSDDH                                                                    7

SEQ ID NO: 107          moltype = AA  length = 6
FEATURE                 Location/Qualifiers
source                  1..6
                        mol_type = protein
                        organism = synthetic construct
SEQUENCE: 107
SGRSDD                                                                     6

SEQ ID NO: 108          moltype = AA  length = 8
FEATURE                 Location/Qualifiers
source                  1..8
                        mol_type = protein
                        organism = synthetic construct
SEQUENCE: 108
LSGRSANI                                                                   8

SEQ ID NO: 109          moltype = AA  length = 7
FEATURE                 Location/Qualifiers
source                  1..7
                        mol_type = protein
                        organism = synthetic construct
SEQUENCE: 109
LSGRSAN                                                                    7

SEQ ID NO: 110          moltype = AA  length = 6
FEATURE                 Location/Qualifiers
source                  1..6
                        mol_type = protein
                        organism = synthetic construct
SEQUENCE: 110
LSGRSA                                                                     6

SEQ ID NO: 111          moltype = AA  length = 7
FEATURE                 Location/Qualifiers
source                  1..7
                        mol_type = protein
                        organism = synthetic construct
SEQUENCE: 111
SGRSANI                                                                    7
```

```
SEQ ID NO: 112          moltype = AA  length = 6
FEATURE                 Location/Qualifiers
source                  1..6
                        mol_type = protein
                        organism = synthetic construct
SEQUENCE: 112
SGRSAN                                                                      6

SEQ ID NO: 113          moltype = AA  length = 5
FEATURE                 Location/Qualifiers
source                  1..5
                        mol_type = protein
                        organism = synthetic construct
SEQUENCE: 113
SGRSA                                                                       5

SEQ ID NO: 114          moltype = AA  length = 8
FEATURE                 Location/Qualifiers
source                  1..8
                        mol_type = protein
                        organism = synthetic construct
SEQUENCE: 114
LSGRSANP                                                                    8

SEQ ID NO: 115          moltype = AA  length = 7
FEATURE                 Location/Qualifiers
source                  1..7
                        mol_type = protein
                        organism = synthetic construct
SEQUENCE: 115
SGRSANP                                                                     7

SEQ ID NO: 116          moltype =   length =
SEQUENCE: 116
000

SEQ ID NO: 117          moltype =   length =
SEQUENCE: 117
000

SEQ ID NO: 118          moltype =   length =
SEQUENCE: 118
000

SEQ ID NO: 119          moltype =   length =
SEQUENCE: 119
000

SEQ ID NO: 120          moltype = AA  length = 8
FEATURE                 Location/Qualifiers
source                  1..8
                        mol_type = protein
                        organism = synthetic construct
SEQUENCE: 120
TARGPSFK                                                                    8

SEQ ID NO: 121          moltype = AA  length = 7
FEATURE                 Location/Qualifiers
source                  1..7
                        mol_type = protein
                        organism = synthetic construct
SEQUENCE: 121
ARGPSFK                                                                     7

SEQ ID NO: 122          moltype = AA  length = 7
FEATURE                 Location/Qualifiers
source                  1..7
                        mol_type = protein
                        organism = synthetic construct
SEQUENCE: 122
TARGPSF                                                                     7

SEQ ID NO: 123          moltype = AA  length = 6
FEATURE                 Location/Qualifiers
source                  1..6
                        mol_type = protein
                        organism = synthetic construct
SEQUENCE: 123
```

```
TARGPS                                                          6

SEQ ID NO: 124          moltype = AA  length = 5
FEATURE                 Location/Qualifiers
source                  1..5
                        mol_type = protein
                        organism = synthetic construct
SEQUENCE: 124
TARGP                                                           5

SEQ ID NO: 125          moltype = AA  length = 4
FEATURE                 Location/Qualifiers
source                  1..4
                        mol_type = protein
                        organism = synthetic construct
SEQUENCE: 125
TARG                                                            4

SEQ ID NO: 126          moltype = AA  length = 6
FEATURE                 Location/Qualifiers
source                  1..6
                        mol_type = protein
                        organism = synthetic construct
SEQUENCE: 126
ARGPSF                                                          6

SEQ ID NO: 127          moltype = AA  length = 5
FEATURE                 Location/Qualifiers
source                  1..5
                        mol_type = protein
                        organism = synthetic construct
SEQUENCE: 127
ARGPS                                                           5

SEQ ID NO: 128          moltype = AA  length = 4
FEATURE                 Location/Qualifiers
source                  1..4
                        mol_type = protein
                        organism = synthetic construct
SEQUENCE: 128
ARGP                                                            4

SEQ ID NO: 129          moltype =   length =
SEQUENCE: 129
000

SEQ ID NO: 130          moltype = AA  length = 5
FEATURE                 Location/Qualifiers
source                  1..5
                        mol_type = protein
                        organism = synthetic construct
SEQUENCE: 130
APRSF                                                           5

SEQ ID NO: 131          moltype = AA  length = 4
FEATURE                 Location/Qualifiers
source                  1..4
                        mol_type = protein
                        organism = synthetic construct
SEQUENCE: 131
APRS                                                            4

SEQ ID NO: 132          moltype = AA  length = 4
FEATURE                 Location/Qualifiers
source                  1..4
                        mol_type = protein
                        organism = synthetic construct
SEQUENCE: 132
PRSF                                                            4

SEQ ID NO: 133          moltype =   length =
SEQUENCE: 133
000

SEQ ID NO: 134          moltype =   length =
SEQUENCE: 134
000

SEQ ID NO: 135          moltype = AA  length = 8
```

-continued

```
FEATURE                 Location/Qualifiers
source                  1..8
                        mol_type = protein
                        organism = synthetic construct
SEQUENCE: 135
GLPTFVHL                                                                    8

SEQ ID NO: 136          moltype = AA  length = 7
FEATURE                 Location/Qualifiers
source                  1..7
                        mol_type = protein
                        organism = synthetic construct
SEQUENCE: 136
GLPTFVH                                                                     7

SEQ ID NO: 137          moltype = AA  length = 6
FEATURE                 Location/Qualifiers
source                  1..6
                        mol_type = protein
                        organism = synthetic construct
SEQUENCE: 137
GLPTFV                                                                      6

SEQ ID NO: 138          moltype = AA  length = 7
FEATURE                 Location/Qualifiers
source                  1..7
                        mol_type = protein
                        organism = synthetic construct
SEQUENCE: 138
LPTFVHL                                                                     7

SEQ ID NO: 139          moltype = AA  length = 6
FEATURE                 Location/Qualifiers
source                  1..6
                        mol_type = protein
                        organism = synthetic construct
SEQUENCE: 139
LPTFVH                                                                      6

SEQ ID NO: 140          moltype = AA  length = 5
FEATURE                 Location/Qualifiers
source                  1..5
                        mol_type = protein
                        organism = synthetic construct
SEQUENCE: 140
LPTFV                                                                       5

SEQ ID NO: 141          moltype = AA  length = 4
FEATURE                 Location/Qualifiers
source                  1..4
                        mol_type = protein
                        organism = synthetic construct
SEQUENCE: 141
TFVH                                                                        4

SEQ ID NO: 142          moltype =   length =
SEQUENCE: 142
000

SEQ ID NO: 143          moltype =   length =
SEQUENCE: 143
000

SEQ ID NO: 144          moltype =   length =
SEQUENCE: 144
000

SEQ ID NO: 145          moltype =   length =
SEQUENCE: 145
000

SEQ ID NO: 146          moltype =   length =
SEQUENCE: 146
000

SEQ ID NO: 147          moltype =   length =
SEQUENCE: 147
000
```

```
SEQ ID NO: 148          moltype =   length =
SEQUENCE: 148
000

SEQ ID NO: 149          moltype =   length =
SEQUENCE: 149
000

SEQ ID NO: 150          moltype =   length =
SEQUENCE: 150
000

SEQ ID NO: 151          moltype =   length =
SEQUENCE: 151
000

SEQ ID NO: 152          moltype = AA  length = 4
FEATURE                 Location/Qualifiers
source                  1..4
                        mol_type = protein
                        organism = synthetic construct
SEQUENCE: 152
GPTN                                                                4

SEQ ID NO: 153          moltype = AA  length = 6
FEATURE                 Location/Qualifiers
source                  1..6
                        mol_type = protein
                        organism = synthetic construct
SEQUENCE: 153
QGQSGQ                                                              6

SEQ ID NO: 154          moltype = AA  length = 5
FEATURE                 Location/Qualifiers
source                  1..5
                        mol_type = protein
                        organism = synthetic construct
SEQUENCE: 154
GQSGQ                                                               5

SEQ ID NO: 155          moltype = AA  length = 4
FEATURE                 Location/Qualifiers
source                  1..4
                        mol_type = protein
                        organism = synthetic construct
SEQUENCE: 155
QSGQ                                                                4

SEQ ID NO: 156          moltype =   length =
SEQUENCE: 156
000

SEQ ID NO: 157          moltype =   length =
SEQUENCE: 157
000

SEQ ID NO: 158          moltype =   length =
SEQUENCE: 158
000

SEQ ID NO: 159          moltype =   length =
SEQUENCE: 159
000

SEQ ID NO: 160          moltype =   length =
SEQUENCE: 160
000

SEQ ID NO: 161          moltype =   length =
SEQUENCE: 161
000

SEQ ID NO: 162          moltype =   length =
SEQUENCE: 162
000

SEQ ID NO: 163          moltype =   length =
SEQUENCE: 163
000
```

```
SEQ ID NO: 164          moltype = AA  length = 15
FEATURE                 Location/Qualifiers
source                  1..15
                        mol_type = protein
                        organism = synthetic construct
SEQUENCE: 164
CISPRGCNAV SGLGS                                                    15

SEQ ID NO: 165          moltype = AA  length = 6
FEATURE                 Location/Qualifiers
source                  1..6
                        mol_type = protein
                        organism = synthetic construct
SEQUENCE: 165
CISPRG                                                              6

SEQ ID NO: 166          moltype = AA  length = 7
FEATURE                 Location/Qualifiers
source                  1..7
                        mol_type = protein
                        organism = synthetic construct
SEQUENCE: 166
CISPRGC                                                             7

SEQ ID NO: 167          moltype = AA  length = 8
FEATURE                 Location/Qualifiers
source                  1..8
                        mol_type = protein
                        organism = synthetic construct
SEQUENCE: 167
CISPRGCG                                                            8

SEQ ID NO: 168          moltype = AA  length = 15
FEATURE                 Location/Qualifiers
source                  1..15
                        mol_type = protein
                        organism = synthetic construct
SEQUENCE: 168
CISPRGCPDG PYVMY                                                    15

SEQ ID NO: 169          moltype = AA  length = 14
FEATURE                 Location/Qualifiers
source                  1..14
                        mol_type = protein
                        organism = synthetic construct
SEQUENCE: 169
CISPRGCPDG PYVM                                                     14

SEQ ID NO: 170          moltype = AA  length = 15
FEATURE                 Location/Qualifiers
source                  1..15
                        mol_type = protein
                        organism = synthetic construct
SEQUENCE: 170
CISPRGCEPG TYVPT                                                    15

SEQ ID NO: 171          moltype = AA  length = 15
FEATURE                 Location/Qualifiers
source                  1..15
                        mol_type = protein
                        organism = synthetic construct
SEQUENCE: 171
CISPRGCPGQ IWHPP                                                    15

SEQ ID NO: 172          moltype = AA  length = 15
FEATURE                 Location/Qualifiers
source                  1..15
                        mol_type = protein
                        organism = synthetic construct
SEQUENCE: 172
GSHCLIPINM GAPSC                                                    15

SEQ ID NO: 173          moltype = AA  length = 32
FEATURE                 Location/Qualifiers
source                  1..32
                        mol_type = protein
                        organism = synthetic construct
SEQUENCE: 173
```

```
CISPRGCGGS SASQSGQGSH CLIPINMGAP SC                              32

SEQ ID NO: 174          moltype = AA  length = 19
FEATURE                 Location/Qualifiers
source                  1..19
                        mol_type = protein
                        organism = synthetic construct
SEQUENCE: 174
CNHHYFYTCG CISPRGCPG                                             19

SEQ ID NO: 175          moltype = AA  length = 19
FEATURE                 Location/Qualifiers
source                  1..19
                        mol_type = protein
                        organism = synthetic construct
SEQUENCE: 175
ADHVFWGSYG CISPRGCPG                                             19

SEQ ID NO: 176          moltype = AA  length = 19
FEATURE                 Location/Qualifiers
source                  1..19
                        mol_type = protein
                        organism = synthetic construct
SEQUENCE: 176
CHHVYWGHCG CISPRGCPG                                             19

SEQ ID NO: 177          moltype = AA  length = 19
FEATURE                 Location/Qualifiers
source                  1..19
                        mol_type = protein
                        organism = synthetic construct
SEQUENCE: 177
CPHFTTTSCG CISPRGCPG                                             19

SEQ ID NO: 178          moltype = AA  length = 19
FEATURE                 Location/Qualifiers
source                  1..19
                        mol_type = protein
                        organism = synthetic construct
SEQUENCE: 178
CNHHYHYYCG CISPRGCPG                                             19

SEQ ID NO: 179          moltype = AA  length = 19
FEATURE                 Location/Qualifiers
source                  1..19
                        mol_type = protein
                        organism = synthetic construct
SEQUENCE: 179
CPHVSFGSCG CISPRGCPG                                             19

SEQ ID NO: 180          moltype = AA  length = 19
FEATURE                 Location/Qualifiers
source                  1..19
                        mol_type = protein
                        organism = synthetic construct
SEQUENCE: 180
CPYYTLSYCG CISPRGCPG                                             19

SEQ ID NO: 181          moltype = AA  length = 19
FEATURE                 Location/Qualifiers
source                  1..19
                        mol_type = protein
                        organism = synthetic construct
SEQUENCE: 181
CNHVYFGTCG CISPRGCPG                                             19

SEQ ID NO: 182          moltype = AA  length = 19
FEATURE                 Location/Qualifiers
source                  1..19
                        mol_type = protein
                        organism = synthetic construct
SEQUENCE: 182
CNHFTLTTCG CISPRGCPG                                             19

SEQ ID NO: 183          moltype = AA  length = 19
FEATURE                 Location/Qualifiers
source                  1..19
                        mol_type = protein
                        organism = synthetic construct
```

```
SEQUENCE: 183
CHHFTLTTCG CISPRGCPG                                            19

SEQ ID NO: 184          moltype = AA  length = 18
FEATURE                 Location/Qualifiers
source                  1..18
                        mol_type = protein
                        organism = synthetic construct
SEQUENCE: 184
YNPCATPMCC ISPRGCPG                                             18

SEQ ID NO: 185          moltype = AA  length = 18
FEATURE                 Location/Qualifiers
source                  1..18
                        mol_type = protein
                        organism = synthetic construct
SEQUENCE: 185
CNHHYFYTCG CISPRGCG                                             18

SEQ ID NO: 186          moltype = AA  length = 18
FEATURE                 Location/Qualifiers
source                  1..18
                        mol_type = protein
                        organism = synthetic construct
SEQUENCE: 186
CNHHYHYYCG CISPRGCG                                             18

SEQ ID NO: 187          moltype = AA  length = 18
FEATURE                 Location/Qualifiers
source                  1..18
                        mol_type = protein
                        organism = synthetic construct
SEQUENCE: 187
CNHVYFGTCG CISPRGCG                                             18

SEQ ID NO: 188          moltype = AA  length = 18
FEATURE                 Location/Qualifiers
source                  1..18
                        mol_type = protein
                        organism = synthetic construct
SEQUENCE: 188
CHHVYWGHCG CISPRGCG                                             18

SEQ ID NO: 189          moltype = AA  length = 18
FEATURE                 Location/Qualifiers
source                  1..18
                        mol_type = protein
                        organism = synthetic construct
SEQUENCE: 189
CPHFTTTSCG CISPRGCG                                             18

SEQ ID NO: 190          moltype = AA  length = 18
FEATURE                 Location/Qualifiers
source                  1..18
                        mol_type = protein
                        organism = synthetic construct
SEQUENCE: 190
CNHFTLTTCG CISPRGCG                                             18

SEQ ID NO: 191          moltype = AA  length = 18
FEATURE                 Location/Qualifiers
source                  1..18
                        mol_type = protein
                        organism = synthetic construct
SEQUENCE: 191
CHHFTLTTCG CISPRGCG                                             18

SEQ ID NO: 192          moltype = AA  length = 18
FEATURE                 Location/Qualifiers
source                  1..18
                        mol_type = protein
                        organism = synthetic construct
SEQUENCE: 192
CPYYTLSYCG CISPRGCG                                             18

SEQ ID NO: 193          moltype = AA  length = 18
FEATURE                 Location/Qualifiers
source                  1..18
                        mol_type = protein
```

```
                         organism = synthetic construct
SEQUENCE: 193
CPHVSFGSCG CISPRGCG                                              18

SEQ ID NO: 194           moltype = AA  length = 18
FEATURE                  Location/Qualifiers
source                   1..18
                         mol_type = protein
                         organism = synthetic construct
SEQUENCE: 194
ADHVFWGSYG CISPRGCG                                              18

SEQ ID NO: 195           moltype = AA  length = 17
FEATURE                  Location/Qualifiers
source                   1..17
                         mol_type = protein
                         organism = synthetic construct
SEQUENCE: 195
YNPCATPMCC ISPRGCG                                               17

SEQ ID NO: 196           moltype = AA  length = 18
FEATURE                  Location/Qualifiers
source                   1..18
                         mol_type = protein
                         organism = synthetic construct
SEQUENCE: 196
CHHVYWGHCG CISPRGCG                                              18

SEQ ID NO: 197           moltype = AA  length = 18
FEATURE                  Location/Qualifiers
VARIANT                  2
                         note = X=Asn or Pro
VARIANT                  4
                         note = X=His or Val or Phe
VARIANT                  5
                         note = X=Tyr or Thr
VARIANT                  6
                         note = X=Phe or Trp or Thr or Leu
VARIANT                  7
                         note = X=Tyr or Gly or Thr or Ser
VARIANT                  8
                         note = X=Thr or Ser or Tyr or His
source                   1..18
                         mol_type = protein
                         organism = synthetic construct
SEQUENCE: 197
CXHXXXXXCG CISPRGCG                                              18

SEQ ID NO: 198           moltype = AA  length = 15
FEATURE                  Location/Qualifiers
source                   1..15
                         mol_type = protein
                         organism = synthetic construct
SEQUENCE: 198
CISPRGCGQP IPSVK                                                 15

SEQ ID NO: 199           moltype = AA  length = 15
FEATURE                  Location/Qualifiers
source                   1..15
                         mol_type = protein
                         organism = synthetic construct
SEQUENCE: 199
CISPRGCTQP YHVSR                                                 15

SEQ ID NO: 200           moltype = AA  length = 5
FEATURE                  Location/Qualifiers
source                   1..5
                         mol_type = protein
                         organism = synthetic construct
SEQUENCE: 200
GSGGS                                                            5

SEQ ID NO: 201           moltype = AA  length = 4
FEATURE                  Location/Qualifiers
source                   1..4
                         mol_type = protein
                         organism = synthetic construct
SEQUENCE: 201
GGGS                                                             4
```

```
SEQ ID NO: 202          moltype = AA  length = 4
FEATURE                 Location/Qualifiers
source                  1..4
                        mol_type = protein
                        organism = synthetic construct
SEQUENCE: 202
GGSG                                                                        4

SEQ ID NO: 203          moltype = AA  length = 5
FEATURE                 Location/Qualifiers
source                  1..5
                        mol_type = protein
                        organism = synthetic construct
SEQUENCE: 203
GGSGG                                                                       5

SEQ ID NO: 204          moltype = AA  length = 5
FEATURE                 Location/Qualifiers
source                  1..5
                        mol_type = protein
                        organism = synthetic construct
SEQUENCE: 204
GSGSG                                                                       5

SEQ ID NO: 205          moltype = AA  length = 5
FEATURE                 Location/Qualifiers
source                  1..5
                        mol_type = protein
                        organism = synthetic construct
SEQUENCE: 205
GSGGG                                                                       5

SEQ ID NO: 206          moltype = AA  length = 5
FEATURE                 Location/Qualifiers
source                  1..5
                        mol_type = protein
                        organism = synthetic construct
SEQUENCE: 206
GGGSG                                                                       5

SEQ ID NO: 207          moltype = AA  length = 5
FEATURE                 Location/Qualifiers
source                  1..5
                        mol_type = protein
                        organism = synthetic construct
SEQUENCE: 207
GSSSG                                                                       5

SEQ ID NO: 208          moltype = AA  length = 13
FEATURE                 Location/Qualifiers
source                  1..13
                        mol_type = protein
                        organism = synthetic construct
SEQUENCE: 208
GSSGGSGGSG GSG                                                              13

SEQ ID NO: 209          moltype = AA  length = 11
FEATURE                 Location/Qualifiers
source                  1..11
                        mol_type = protein
                        organism = synthetic construct
SEQUENCE: 209
GSSGGSGGSG G                                                                11

SEQ ID NO: 210          moltype = AA  length = 12
FEATURE                 Location/Qualifiers
source                  1..12
                        mol_type = protein
                        organism = synthetic construct
SEQUENCE: 210
GSSGGSGGSG GS                                                               12

SEQ ID NO: 211          moltype = AA  length = 16
FEATURE                 Location/Qualifiers
source                  1..16
                        mol_type = protein
                        organism = synthetic construct
SEQUENCE: 211
```

```
GSSGGSGGSG GSGGGS                                                      16

SEQ ID NO: 212          moltype = AA  length = 10
FEATURE                 Location/Qualifiers
source                  1..10
                        mol_type = protein
                        organism = synthetic construct
SEQUENCE: 212
GSSGGSGGSG                                                             10

SEQ ID NO: 213          moltype = AA  length = 11
FEATURE                 Location/Qualifiers
source                  1..11
                        mol_type = protein
                        organism = synthetic construct
SEQUENCE: 213
GSSGGSGGSG S                                                           11

SEQ ID NO: 214          moltype = AA  length = 8
FEATURE                 Location/Qualifiers
source                  1..8
                        mol_type = protein
                        organism = synthetic construct
SEQUENCE: 214
GGGSSGGS                                                               8

SEQ ID NO: 215          moltype = AA  length = 4
FEATURE                 Location/Qualifiers
source                  1..4
                        mol_type = protein
                        organism = synthetic construct
SEQUENCE: 215
GGGS                                                                   4

SEQ ID NO: 216          moltype = AA  length = 5
FEATURE                 Location/Qualifiers
source                  1..5
                        mol_type = protein
                        organism = synthetic construct
SEQUENCE: 216
GSSGT                                                                  5

SEQ ID NO: 217          moltype = AA  length = 4
FEATURE                 Location/Qualifiers
source                  1..4
                        mol_type = protein
                        organism = synthetic construct
SEQUENCE: 217
GSSG                                                                   4

SEQ ID NO: 218          moltype = AA  length = 6
FEATURE                 Location/Qualifiers
source                  1..6
                        mol_type = protein
                        organism = synthetic construct
SEQUENCE: 218
GGSGGS                                                                 6

SEQ ID NO: 219          moltype =   length =
SEQUENCE: 219
000

SEQ ID NO: 220          moltype = AA  length = 5
FEATURE                 Location/Qualifiers
source                  1..5
                        mol_type = protein
                        organism = synthetic construct
SEQUENCE: 220
NYGVH                                                                  5

SEQ ID NO: 221          moltype = AA  length = 16
FEATURE                 Location/Qualifiers
source                  1..16
                        mol_type = protein
                        organism = synthetic construct
SEQUENCE: 221
VIWSGGNTDY NTPFTS                                                      16

SEQ ID NO: 222          moltype = AA  length = 11
```

-continued

```
FEATURE                Location/Qualifiers
source                 1..11
                       mol_type = protein
                       organism = synthetic construct
SEQUENCE: 222
ALTYYDYEFA Y                                                     11

SEQ ID NO: 223         moltype = AA  length = 11
FEATURE                Location/Qualifiers
source                 1..11
                       mol_type = protein
                       organism = synthetic construct
SEQUENCE: 223
RASQSIGTNI H                                                     11

SEQ ID NO: 224         moltype = AA  length = 8
FEATURE                Location/Qualifiers
source                 1..8
                       mol_type = protein
                       organism = synthetic construct
SEQUENCE: 224
KYASESIS                                                         8

SEQ ID NO: 225         moltype = AA  length = 9
FEATURE                Location/Qualifiers
source                 1..9
                       mol_type = protein
                       organism = synthetic construct
SEQUENCE: 225
QQNNNWPTT                                                        9

SEQ ID NO: 226         moltype = AA  length = 16
FEATURE                Location/Qualifiers
source                 1..16
                       mol_type = protein
                       organism = synthetic construct
SEQUENCE: 226
LSGRSALAHG LFGGGS                                                16

SEQ ID NO: 227         moltype = AA  length = 17
FEATURE                Location/Qualifiers
source                 1..17
                       mol_type = protein
                       organism = synthetic construct
SEQUENCE: 227
ALAHGLFSGR SANGGGS                                               17

SEQ ID NO: 228         moltype = AA  length = 15
FEATURE                Location/Qualifiers
source                 1..15
                       mol_type = protein
                       organism = synthetic construct
SEQUENCE: 228
HVPRQVLSGR SGGGS                                                 15

SEQ ID NO: 229         moltype = AA  length = 17
FEATURE                Location/Qualifiers
source                 1..17
                       mol_type = protein
                       organism = synthetic construct
SEQUENCE: 229
HVPRQVLSGR SANGGGS                                               17

SEQ ID NO: 230         moltype = AA  length = 16
FEATURE                Location/Qualifiers
source                 1..16
                       mol_type = protein
                       organism = synthetic construct
SEQUENCE: 230
TARGPALAHG LFGGGS                                                16

SEQ ID NO: 231         moltype = AA  length = 14
FEATURE                Location/Qualifiers
source                 1..14
                       mol_type = protein
                       organism = synthetic construct
SEQUENCE: 231
TARGPVPRQV GGGS                                                  14
```

-continued

```
SEQ ID NO: 232          moltype = AA  length = 15
FEATURE                 Location/Qualifiers
source                  1..15
                        mol_type = protein
                        organism = synthetic construct
SEQUENCE: 232
APRSALAHGL FGGGS                                                    15

SEQ ID NO: 233          moltype = AA  length = 16
FEATURE                 Location/Qualifiers
source                  1..16
                        mol_type = protein
                        organism = synthetic construct
SEQUENCE: 233
ALAHGLFAPR SFGGGS                                                   16

SEQ ID NO: 234          moltype = AA  length = 15
FEATURE                 Location/Qualifiers
source                  1..15
                        mol_type = protein
                        organism = synthetic construct
SEQUENCE: 234
HVPRQVAPRS FGGGS                                                    15

SEQ ID NO: 235          moltype = AA  length = 16
FEATURE                 Location/Qualifiers
source                  1..16
                        mol_type = protein
                        organism = synthetic construct
SEQUENCE: 235
ALAHGLPTFV HLGGGS                                                   16

SEQ ID NO: 236          moltype = AA  length = 16
FEATURE                 Location/Qualifiers
source                  1..16
                        mol_type = protein
                        organism = synthetic construct
SEQUENCE: 236
GLPTFVHLPR QVGGGS                                                   16

SEQ ID NO: 237          moltype = AA  length = 14
FEATURE                 Location/Qualifiers
source                  1..14
                        mol_type = protein
                        organism = synthetic construct
SEQUENCE: 237
AANALAHGLF GGGS                                                     14

SEQ ID NO: 238          moltype = AA  length = 15
FEATURE                 Location/Qualifiers
source                  1..15
                        mol_type = protein
                        organism = synthetic construct
SEQUENCE: 238
GPTNALAHGL FGGGS                                                    15

SEQ ID NO: 239          moltype = AA  length = 16
FEATURE                 Location/Qualifiers
source                  1..16
                        mol_type = protein
                        organism = synthetic construct
SEQUENCE: 239
ISSGLLSGRS NIGGGS                                                   16

SEQ ID NO: 240          moltype = AA  length = 21
FEATURE                 Location/Qualifiers
source                  1..21
                        mol_type = protein
                        organism = synthetic construct
SEQUENCE: 240
AVGLLAPPGG LSGRSNIGGG S                                             21

SEQ ID NO: 241          moltype = AA  length = 15
FEATURE                 Location/Qualifiers
source                  1..15
                        mol_type = protein
                        organism = synthetic construct
SEQUENCE: 241
LSGRSALAHG LFGGS                                                    15
```

```
SEQ ID NO: 242          moltype = AA  length = 16
FEATURE                 Location/Qualifiers
source                  1..16
                        mol_type = protein
                        organism = synthetic construct
SEQUENCE: 242
ALAHGLFSGR SANGGS                                                    16

SEQ ID NO: 243          moltype = AA  length = 14
FEATURE                 Location/Qualifiers
source                  1..14
                        mol_type = protein
                        organism = synthetic construct
SEQUENCE: 243
HVPRQVLSGR SGGS                                                      14

SEQ ID NO: 244          moltype = AA  length = 16
FEATURE                 Location/Qualifiers
source                  1..16
                        mol_type = protein
                        organism = synthetic construct
SEQUENCE: 244
HVPRQVLSGR SANGGS                                                    16

SEQ ID NO: 245          moltype = AA  length = 15
FEATURE                 Location/Qualifiers
source                  1..15
                        mol_type = protein
                        organism = synthetic construct
SEQUENCE: 245
TARGPALAHG LFGGS                                                     15

SEQ ID NO: 246          moltype = AA  length = 13
FEATURE                 Location/Qualifiers
source                  1..13
                        mol_type = protein
                        organism = synthetic construct
SEQUENCE: 246
TARGPVPRQV GGS                                                       13

SEQ ID NO: 247          moltype = AA  length = 14
FEATURE                 Location/Qualifiers
source                  1..14
                        mol_type = protein
                        organism = synthetic construct
SEQUENCE: 247
APRSALAHGL FGGS                                                      14

SEQ ID NO: 248          moltype = AA  length = 15
FEATURE                 Location/Qualifiers
source                  1..15
                        mol_type = protein
                        organism = synthetic construct
SEQUENCE: 248
ALAHGLFAPR SFGGS                                                     15

SEQ ID NO: 249          moltype = AA  length = 14
FEATURE                 Location/Qualifiers
source                  1..14
                        mol_type = protein
                        organism = synthetic construct
SEQUENCE: 249
HVPRQVAPRS FGGS                                                      14

SEQ ID NO: 250          moltype = AA  length = 15
FEATURE                 Location/Qualifiers
source                  1..15
                        mol_type = protein
                        organism = synthetic construct
SEQUENCE: 250
ALAHGLPTFV HLGGS                                                     15

SEQ ID NO: 251          moltype = AA  length = 15
FEATURE                 Location/Qualifiers
source                  1..15
                        mol_type = protein
                        organism = synthetic construct
SEQUENCE: 251
```

```
GLPTFVHLPR QVGGS                                                  15

SEQ ID NO: 252          moltype = AA  length = 13
FEATURE                 Location/Qualifiers
source                  1..13
                        mol_type = protein
                        organism = synthetic construct
SEQUENCE: 252
AANALAHGLF GGS                                                    13

SEQ ID NO: 253          moltype = AA  length = 14
FEATURE                 Location/Qualifiers
source                  1..14
                        mol_type = protein
                        organism = synthetic construct
SEQUENCE: 253
GPTNALAHGL FGGS                                                   14

SEQ ID NO: 254          moltype = AA  length = 15
FEATURE                 Location/Qualifiers
source                  1..15
                        mol_type = protein
                        organism = synthetic construct
SEQUENCE: 254
ISSGLLSGRS NIGGS                                                  15

SEQ ID NO: 255          moltype = AA  length = 20
FEATURE                 Location/Qualifiers
source                  1..20
                        mol_type = protein
                        organism = synthetic construct
SEQUENCE: 255
AVGLLAPPGG LSGRSNIGGS                                             20

SEQ ID NO: 256          moltype =   length =
SEQUENCE: 256
000

SEQ ID NO: 257          moltype =   length =
SEQUENCE: 257
000

SEQ ID NO: 258          moltype =   length =
SEQUENCE: 258
000

SEQ ID NO: 259          moltype =   length =
SEQUENCE: 259
000

SEQ ID NO: 260          moltype =   length =
SEQUENCE: 260
000

SEQ ID NO: 261          moltype =   length =
SEQUENCE: 261
000

SEQ ID NO: 262          moltype =   length =
SEQUENCE: 262
000

SEQ ID NO: 263          moltype =   length =
SEQUENCE: 263
000

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
```

```
SEQUENCE: 267
000

SEQ ID NO: 268          moltype =   length =
SEQUENCE: 268
000

SEQ ID NO: 269          moltype =   length =
SEQUENCE: 269
000

SEQ ID NO: 270          moltype =   length =
SEQUENCE: 270
000

SEQ ID NO: 271          moltype =   length =
SEQUENCE: 271
000

SEQ ID NO: 272          moltype =   length =
SEQUENCE: 272
000

SEQ ID NO: 273          moltype =   length =
SEQUENCE: 273
000

SEQ ID NO: 274          moltype =   length =
SEQUENCE: 274
000

SEQ ID NO: 275          moltype =   length =
SEQUENCE: 275
000

SEQ ID NO: 276          moltype =   length =
SEQUENCE: 276
000

SEQ ID NO: 277          moltype =   length =
SEQUENCE: 277
000

SEQ ID NO: 278          moltype =   length =
SEQUENCE: 278
000

SEQ ID NO: 279          moltype =   length =
SEQUENCE: 279
000

SEQ ID NO: 280          moltype =   length =
SEQUENCE: 280
000

SEQ ID NO: 281          moltype =   length =
SEQUENCE: 281
000

SEQ ID NO: 282          moltype =   length =
SEQUENCE: 282
000

SEQ ID NO: 283          moltype =   length =
SEQUENCE: 283
000

SEQ ID NO: 284          moltype =   length =
SEQUENCE: 284
000

SEQ ID NO: 285          moltype =   length =
SEQUENCE: 285
000

SEQ ID NO: 286          moltype =   length =
SEQUENCE: 286
000
```

-continued

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

```
SEQ ID NO: 307          moltype =   length =
SEQUENCE: 307
000

SEQ ID NO: 308          moltype =   length =
SEQUENCE: 308
000

SEQ ID NO: 309          moltype =   length =
SEQUENCE: 309
000

SEQ ID NO: 310          moltype =   length =
SEQUENCE: 310
000

SEQ ID NO: 311          moltype =   length =
SEQUENCE: 311
000

SEQ ID NO: 312          moltype =   length =
SEQUENCE: 312
000

SEQ ID NO: 313          moltype =   length =
SEQUENCE: 313
000

SEQ ID NO: 314          moltype =   length =
SEQUENCE: 314
000

SEQ ID NO: 315          moltype =   length =
SEQUENCE: 315
000

SEQ ID NO: 316          moltype =   length =
SEQUENCE: 316
000

SEQ ID NO: 317          moltype =   length =
SEQUENCE: 317
000

SEQ ID NO: 318          moltype =   length =
SEQUENCE: 318
000

SEQ ID NO: 319          moltype = AA  length = 8
FEATURE                 Location/Qualifiers
source                  1..8
                        mol_type = protein
                        organism = synthetic construct
SEQUENCE: 319
PRFKIIGG                                                                8

SEQ ID NO: 320          moltype = AA  length = 8
FEATURE                 Location/Qualifiers
source                  1..8
                        mol_type = protein
                        organism = synthetic construct
SEQUENCE: 320
PRFRIIGG                                                                8

SEQ ID NO: 321          moltype = AA  length = 9
FEATURE                 Location/Qualifiers
source                  1..9
                        mol_type = protein
                        organism = synthetic construct
SEQUENCE: 321
SSRHRRALD                                                               9

SEQ ID NO: 322          moltype = AA  length = 14
FEATURE                 Location/Qualifiers
source                  1..14
                        mol_type = protein
                        organism = synthetic construct
SEQUENCE: 322
```

```
RKSSIIIRMR DVVL                                                     14

SEQ ID NO: 323          moltype = AA  length = 15
FEATURE                 Location/Qualifiers
source                  1..15
                        mol_type = protein
                        organism = synthetic construct
SEQUENCE: 323
SSSFDKGKYK KGDDA                                                    15

SEQ ID NO: 324          moltype = AA  length = 15
FEATURE                 Location/Qualifiers
source                  1..15
                        mol_type = protein
                        organism = synthetic construct
SEQUENCE: 324
SSSFDKGKYK RGDDA                                                    15

SEQ ID NO: 325          moltype = AA  length = 4
FEATURE                 Location/Qualifiers
source                  1..4
                        mol_type = protein
                        organism = synthetic construct
SEQUENCE: 325
IEGR                                                                4

SEQ ID NO: 326          moltype = AA  length = 4
FEATURE                 Location/Qualifiers
source                  1..4
                        mol_type = protein
                        organism = synthetic construct
SEQUENCE: 326
IDGR                                                                4

SEQ ID NO: 327          moltype = AA  length = 7
FEATURE                 Location/Qualifiers
source                  1..7
                        mol_type = protein
                        organism = synthetic construct
SEQUENCE: 327
GGSIDGR                                                             7

SEQ ID NO: 328          moltype = AA  length = 6
FEATURE                 Location/Qualifiers
source                  1..6
                        mol_type = protein
                        organism = synthetic construct
SEQUENCE: 328
PLGLWA                                                              6

SEQ ID NO: 329          moltype = AA  length = 8
FEATURE                 Location/Qualifiers
source                  1..8
                        mol_type = protein
                        organism = synthetic construct
SEQUENCE: 329
GPQGIAGQ                                                            8

SEQ ID NO: 330          moltype = AA  length = 8
FEATURE                 Location/Qualifiers
source                  1..8
                        mol_type = protein
                        organism = synthetic construct
SEQUENCE: 330
GPQGLLGA                                                            8

SEQ ID NO: 331          moltype = AA  length = 5
FEATURE                 Location/Qualifiers
source                  1..5
                        mol_type = protein
                        organism = synthetic construct
SEQUENCE: 331
GIAGQ                                                               5

SEQ ID NO: 332          moltype = AA  length = 8
FEATURE                 Location/Qualifiers
source                  1..8
                        mol_type = protein
                        organism = synthetic construct
```

```
SEQUENCE: 332
GPLGIAGI                                                      8

SEQ ID NO: 333          moltype = AA  length = 8
FEATURE                 Location/Qualifiers
source                  1..8
                        mol_type = protein
                        organism = synthetic construct
SEQUENCE: 333
GPEGLRVG                                                      8

SEQ ID NO: 334          moltype = AA  length = 8
FEATURE                 Location/Qualifiers
source                  1..8
                        mol_type = protein
                        organism = synthetic construct
SEQUENCE: 334
YGAGLGVV                                                      8

SEQ ID NO: 335          moltype = AA  length = 8
FEATURE                 Location/Qualifiers
source                  1..8
                        mol_type = protein
                        organism = synthetic construct
SEQUENCE: 335
AGLGVVER                                                      8

SEQ ID NO: 336          moltype = AA  length = 8
FEATURE                 Location/Qualifiers
source                  1..8
                        mol_type = protein
                        organism = synthetic construct
SEQUENCE: 336
AGLGISST                                                      8

SEQ ID NO: 337          moltype = AA  length = 8
FEATURE                 Location/Qualifiers
source                  1..8
                        mol_type = protein
                        organism = synthetic construct
SEQUENCE: 337
EPQALAMS                                                      8

SEQ ID NO: 338          moltype = AA  length = 8
FEATURE                 Location/Qualifiers
source                  1..8
                        mol_type = protein
                        organism = synthetic construct
SEQUENCE: 338
QALAMSAI                                                      8

SEQ ID NO: 339          moltype = AA  length = 8
FEATURE                 Location/Qualifiers
source                  1..8
                        mol_type = protein
                        organism = synthetic construct
SEQUENCE: 339
AAYHLVSQ                                                      8

SEQ ID NO: 340          moltype = AA  length = 8
FEATURE                 Location/Qualifiers
source                  1..8
                        mol_type = protein
                        organism = synthetic construct
SEQUENCE: 340
MDAFLESS                                                      8

SEQ ID NO: 341          moltype = AA  length = 8
FEATURE                 Location/Qualifiers
source                  1..8
                        mol_type = protein
                        organism = synthetic construct
SEQUENCE: 341
ESLPVVAV                                                      8

SEQ ID NO: 342          moltype = AA  length = 8
FEATURE                 Location/Qualifiers
source                  1..8
                        mol_type = protein
```

```
                        organism = synthetic construct
SEQUENCE: 342
SAPAVESE                                                      8

SEQ ID NO: 343          moltype = AA  length = 8
FEATURE                 Location/Qualifiers
source                  1..8
                        mol_type = protein
                        organism = synthetic construct
SEQUENCE: 343
DVAQFVLT                                                      8

SEQ ID NO: 344          moltype = AA  length = 8
FEATURE                 Location/Qualifiers
source                  1..8
                        mol_type = protein
                        organism = synthetic construct
SEQUENCE: 344
VAQFVLTE                                                      8

SEQ ID NO: 345          moltype = AA  length = 8
FEATURE                 Location/Qualifiers
source                  1..8
                        mol_type = protein
                        organism = synthetic construct
SEQUENCE: 345
AQFVLTEG                                                      8

SEQ ID NO: 346          moltype = AA  length = 8
FEATURE                 Location/Qualifiers
source                  1..8
                        mol_type = protein
                        organism = synthetic construct
SEQUENCE: 346
PVQPIGPQ                                                      8

SEQ ID NO: 347          moltype = AA  length = 273
FEATURE                 Location/Qualifiers
source                  1..273
                        mol_type = protein
                        organism = synthetic construct
SEQUENCE: 347
GGGSGGGGSG SGGGSGGGGS GGGEIVLTQS PGTLSLSPGE RATLSCRASQ SVSSSYLAWY  60
QQKPGQAPRL LIYGASSRAT GIPDRFSGSG SGTDFTLTIS RLEPEDFAVY YCQQYGSSPL  120
TFGGGTKVEI KRSGGSTITS YNVYYTKLSS SGTQVQLVQT GGGVVQPGRS LRLSCAASGS  180
TFSSYAMSWV RQAPGKGLEW VSAISGSGGS TYYADSVKGR FTISRDNSKN TLYLQMNSLR  240
AEDTAVYYCA TNSLYWYFDL WGRGTLVTVS SAS                              273

SEQ ID NO: 348          moltype =   length =
SEQUENCE: 348
000

SEQ ID NO: 349          moltype = AA  length = 264
FEATURE                 Location/Qualifiers
source                  1..264
                        mol_type = protein
                        organism = synthetic construct
SEQUENCE: 349
GGGSGGGGSG SGGGSGGGGS GGGQVQLQQS GAELARPGAS VKMSCKASGY TFTRYTMHWV  60
KQRPGQGLEW IGYINPSRGY TNYNQKFKDK ATLTTDKSSS TAYMQLSSLT SEDSAVYYCA  120
RYYDDHYCLD YWGQGTTLTV SSGGGGSGGG GSGGGGSQIV LTQSPAIMSA SPGEKVTMTC  180
SASSSVSYMN WYQQKSGTSP KRWIYDTSKL ASGVPAHFRG SGSGTSYSLT ISGMEAEDAA  240
TYYCQQWSSN PFTFGSGTKL EINR                                        264

SEQ ID NO: 350          moltype =   length =
SEQUENCE: 350
000

SEQ ID NO: 351          moltype =   length =
SEQUENCE: 351
000

SEQ ID NO: 352          moltype =   length =
SEQUENCE: 352
000

SEQ ID NO: 353          moltype =   length =
SEQUENCE: 353
000
```

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373

```
000

SEQ ID NO: 374          moltype =   length =
SEQUENCE: 374
000

SEQ ID NO: 375          moltype =   length =
SEQUENCE: 375
000

SEQ ID NO: 376          moltype =   length =
SEQUENCE: 376
000

SEQ ID NO: 377          moltype =   length =
SEQUENCE: 377
000

SEQ ID NO: 378          moltype =   length =
SEQUENCE: 378
000

SEQ ID NO: 379          moltype =   length =
SEQUENCE: 379
000

SEQ ID NO: 380          moltype =   length =
SEQUENCE: 380
000

SEQ ID NO: 381          moltype = AA  length = 5
FEATURE                 Location/Qualifiers
source                  1..5
                        mol_type = protein
                        organism = synthetic construct
SEQUENCE: 381
GSGGS                                                             5

SEQ ID NO: 382          moltype = AA  length = 4
FEATURE                 Location/Qualifiers
source                  1..4
                        mol_type = protein
                        organism = synthetic construct
SEQUENCE: 382
GGGS                                                              4

SEQ ID NO: 383          moltype = AA  length = 4
FEATURE                 Location/Qualifiers
source                  1..4
                        mol_type = protein
                        organism = synthetic construct
SEQUENCE: 383
GGSG                                                              4

SEQ ID NO: 384          moltype = AA  length = 5
FEATURE                 Location/Qualifiers
source                  1..5
                        mol_type = protein
                        organism = synthetic construct
SEQUENCE: 384
GGSGG                                                             5

SEQ ID NO: 385          moltype = AA  length = 5
FEATURE                 Location/Qualifiers
source                  1..5
                        mol_type = protein
                        organism = synthetic construct
SEQUENCE: 385
GSGSG                                                             5

SEQ ID NO: 386          moltype = AA  length = 5
FEATURE                 Location/Qualifiers
source                  1..5
                        mol_type = protein
                        organism = synthetic construct
SEQUENCE: 386
GSGGG                                                             5

SEQ ID NO: 387          moltype = AA  length = 5
```

-continued

```
FEATURE                Location/Qualifiers
source                 1..5
                       mol_type = protein
                       organism = synthetic construct
SEQUENCE: 387
GGGSG                                                          5

SEQ ID NO: 388         moltype = AA  length = 5
FEATURE                Location/Qualifiers
source                 1..5
                       mol_type = protein
                       organism = synthetic construct
SEQUENCE: 388
GSSSG                                                          5

SEQ ID NO: 389         moltype =   length =
SEQUENCE: 389
000

SEQ ID NO: 390         moltype =   length =
SEQUENCE: 390
000

SEQ ID NO: 391         moltype =   length =
SEQUENCE: 391
000

SEQ ID NO: 392         moltype =   length =
SEQUENCE: 392
000

SEQ ID NO: 393         moltype =   length =
SEQUENCE: 393
000

SEQ ID NO: 394         moltype =   length =
SEQUENCE: 394
000

SEQ ID NO: 395         moltype =   length =
SEQUENCE: 395
000

SEQ ID NO: 396         moltype =   length =
SEQUENCE: 396
000

SEQ ID NO: 397         moltype =   length =
SEQUENCE: 397
000

SEQ ID NO: 398         moltype =   length =
SEQUENCE: 398
000

SEQ ID NO: 399         moltype = AA  length = 214
FEATURE                Location/Qualifiers
source                 1..214
                       mol_type = protein
                       organism = synthetic construct
SEQUENCE: 399
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 400         moltype = AA  length = 449
FEATURE                Location/Qualifiers
source                 1..449
                       mol_type = protein
                       organism = synthetic construct
SEQUENCE: 400
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
```

-continued

```
QGNVFSCSVM HEALHNHYTQ KSLSLSPGK                                   449

SEQ ID NO: 401          moltype = AA  length = 214
FEATURE                 Location/Qualifiers
source                  1..214
                        mol_type = protein
                        organism = synthetic construct
SEQUENCE: 401
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 402          moltype = AA  length = 258
FEATURE                 Location/Qualifiers
source                  1..258
                        mol_type = protein
                        organism = synthetic construct
SEQUENCE: 402
QGQSGQCISP RGCPDGPYVM YGSSGGSGGS GGSGGGSGGG SGGSDILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 403          moltype = AA  length = 254
FEATURE                 Location/Qualifiers
source                  1..254
                        mol_type = protein
                        organism = synthetic construct
SEQUENCE: 403
QGQSGQCISP RGCPDGPYVM YGGGSSGGSA LAHGLFGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                    254

SEQ ID NO: 404          moltype = AA  length = 259
FEATURE                 Location/Qualifiers
source                  1..259
                        mol_type = protein
                        organism = synthetic construct
SEQUENCE: 404
QGQSGQCISP RGCPDGPYVM YGSSGGSGGS GGSGALAHGL FGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 405          moltype = AA  length = 254
FEATURE                 Location/Qualifiers
source                  1..254
                        mol_type = protein
                        organism = synthetic construct
SEQUENCE: 405
QGQSGQCISP RGCPDGPYVM YGGGSSGGSD LAHPLLGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                    254

SEQ ID NO: 406          moltype = AA  length = 253
FEATURE                 Location/Qualifiers
source                  1..253
                        mol_type = protein
                        organism = synthetic construct
SEQUENCE: 406
QGQSGQCISP RGCPDGPYVM YGGGSSGGSA FRHLRGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 407          moltype = AA  length = 258
FEATURE                 Location/Qualifiers
source                  1..258
                        mol_type = protein
                        organism = synthetic construct
SEQUENCE: 407
```

-continued

```
QGQSGQCISP RGCPDGPYVM YGSSGGSGGS GGSGPHGFFQ GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258

SEQ ID NO: 408          moltype = AA  length = 253
FEATURE                 Location/Qualifiers
source                  1..253
                        mol_type = protein
                        organism = synthetic construct
SEQUENCE: 408
QGQSGQCISP RGCPDGPYVM YGGGSSGGSS VHHLIGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                    253

SEQ ID NO: 409          moltype = AA  length = 254
FEATURE                 Location/Qualifiers
source                  1..254
                        mol_type = protein
                        organism = synthetic construct
SEQUENCE: 409
QGQSGQCISP RGCPDGPYVM YGGGSSGGSR GPKLYWGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                   254

SEQ ID NO: 410          moltype = AA  length = 259
FEATURE                 Location/Qualifiers
source                  1..259
                        mol_type = protein
                        organism = synthetic construct
SEQUENCE: 410
QGQSGQCISP RGCPDGPYVM YGSSGGSGGS GGSGRGPKLY WGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                              259

SEQ ID NO: 411          moltype = AA  length = 254
FEATURE                 Location/Qualifiers
source                  1..254
                        mol_type = protein
                        organism = synthetic construct
SEQUENCE: 411
QGQSGQCISP RGCPDGPYVM YGGGSSGGSR FPYGVWGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                   254

SEQ ID NO: 412          moltype = AA  length = 253
FEATURE                 Location/Qualifiers
source                  1..253
                        mol_type = protein
                        organism = synthetic construct
SEQUENCE: 412
QGQSGQCISP RGCPDGPYVM YGGGSSGGSH VPRQVGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                    253

SEQ ID NO: 413          moltype = AA  length = 258
FEATURE                 Location/Qualifiers
source                  1..258
                        mol_type = protein
                        organism = synthetic construct
SEQUENCE: 413
QGQSGQCISP RGCPDGPYVM YGSSGGSGGS GGSGHVPRQV GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258

SEQ ID NO: 414          moltype = AA  length = 253
```

```
FEATURE                Location/Qualifiers
source                 1..253
                       mol_type = protein
                       organism = synthetic construct
SEQUENCE: 414
QGQSGQCISP RGCPDGPYVM YGGGSSGGSS NPFKYGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 415         moltype = AA  length = 253
FEATURE                Location/Qualifiers
source                 1..253
                       mol_type = protein
                       organism = synthetic construct
SEQUENCE: 415
QGQSGQCISP RGCPDGPYVM YGGGSSGGSR FPLKVGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 416         moltype = AA  length = 253
FEATURE                Location/Qualifiers
source                 1..253
                       mol_type = protein
                       organism = synthetic construct
SEQUENCE: 416
QGQSGQCISP RGCPDGPYVM YGGGSSGGSP FHLSRGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 417         moltype = AA  length = 253
FEATURE                Location/Qualifiers
source                 1..253
                       mol_type = protein
                       organism = synthetic construct
SEQUENCE: 417
QGQSGQCISP RGCPDGPYVM YGGGSSGGSS TVFHMGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 418         moltype = AA  length = 253
FEATURE                Location/Qualifiers
source                 1..253
                       mol_type = protein
                       organism = synthetic construct
SEQUENCE: 418
QGQSGQCISP RGCPDGPYVM YGGGSSGGSM GPWFMGGGSQ ILLTQSPVIL SVSPGERVSF  60
SCRASQSIGT NIHWYQQRTN GSPRLLIKYA SESISGIPSR FSGSGSGTDF TLSINSVESE  120
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 419         moltype = AA  length = 258
FEATURE                Location/Qualifiers
source                 1..258
                       mol_type = protein
                       organism = synthetic construct
SEQUENCE: 419
QGQSGQCISP RGCPDGPYVM YGSSGGSGGS GGSGMGPWFM GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 420         moltype = AA  length = 253
FEATURE                Location/Qualifiers
source                 1..253
                       mol_type = protein
                       organism = synthetic construct
SEQUENCE: 420
QGQSGQCISP RGCPDGPYVM YGGGSSGGSR HLAKLGGGSQ ILLTQSPVIL SVSPGERVSF  60
SCRASQSIGT NIHWYQQRTN GSPRLLIKYA SESISGIPSR FSGSGSGTDF TLSINSVESE  120
```

-continued

```
DIADYYCQQN NNWPTTFGAG TKLELKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 421         moltype = AA  length = 254
FEATURE                Location/Qualifiers
source                 1..254
                       mol_type = protein
                       organism = synthetic construct
SEQUENCE: 421
QGQSGQCISP RGCPDGPYVM YGGGSSGGSP LGVRGKGGGS QILLTQSPVI LSVSPGERVS  60
FSCRASQSIG TNIHWYQQRT NGSPRLLIKY ASESISGIPS RFSGSGSGTD FTLSINSVES  120
EDIADYYCQQ NNNWPTTFGA GTKLELKRTV AAPSVFIFPP SDEQLKSGTA SVVCLLNNFY  180
PREAKVQWKV DNALQSGNSQ ESVTEQDSKD STYSLSSTLT LSKADYEKHK VYACEVTHQG  240
LSSPVTKSFN RGEC                                                    254

SEQ ID NO: 422         moltype = AA  length = 259
FEATURE                Location/Qualifiers
source                 1..259
                       mol_type = protein
                       organism = synthetic construct
SEQUENCE: 422
QGQSGQCISP RGCPDGPYVM YGSSGGSGGS GGSGPLGVRG KGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 423         moltype = AA  length = 260
FEATURE                Location/Qualifiers
source                 1..260
                       mol_type = protein
                       organism = synthetic construct
SEQUENCE: 423
QGQSGQCISP RGCPDGPYVM YGSSGGSGGS GGSGQNQALR IAGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 424         moltype =   length =
SEQUENCE: 424
000

SEQ ID NO: 425         moltype =   length =
SEQUENCE: 425
000

SEQ ID NO: 426         moltype =   length =
SEQUENCE: 426
000

SEQ ID NO: 427         moltype =   length =
SEQUENCE: 427
000

SEQ ID NO: 428         moltype =   length =
SEQUENCE: 428
000

SEQ ID NO: 429         moltype =   length =
SEQUENCE: 429
000

SEQ ID NO: 430         moltype =   length =
SEQUENCE: 430
000

SEQ ID NO: 431         moltype =   length =
SEQUENCE: 431
000

SEQ ID NO: 432         moltype =   length =
SEQUENCE: 432
000

SEQ ID NO: 433         moltype =   length =
SEQUENCE: 433
000
```

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440
000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =
SEQUENCE: 444
000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = AA length = 259
FEATURE Location/Qualifiers
source 1..259
mol_type = protein
organism = synthetic construct
SEQUENCE: 450
QGQSGQCISP RGCPDGPYVM YGGGSSGGSL SGRSALAHGL FGGGSQILLT QSPVILSVSP 60
GERVSFSCRA SQSIGTNIHW YQQRTNGSPR LLIKYASESI SGIPSRFSGS GSGTDFTLSI 120
NSVESEDIAD YYCQQNNNWP TTFGAGTKLE LKRTVAAPSV FIFPPSDEQL KSGTASVVCL 180
LNNFYPREAK VQWKVDNALQ SGNSQESVTE QDSKDSTYSL SSTLTLSKAD YEKHKVYACE 240
VTHQGLSSPV TKSFNRGEC 259

SEQ ID NO: 451 moltype = AA length = 260
FEATURE Location/Qualifiers

```
source                  1..260
                        mol_type = protein
                        organism = synthetic construct
SEQUENCE: 451
QGQSGQCISP RGCPDGPYVM YGGGSSGGSA LAHGLFSGRS ANGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 452          moltype = AA  length = 258
FEATURE                 Location/Qualifiers
source                  1..258
                        mol_type = protein
                        organism = synthetic construct
SEQUENCE: 452
QGQSGQCISP RGCPDGPYVM YGGGSSGGSH VPRQVLSGRS GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 453          moltype = AA  length = 260
FEATURE                 Location/Qualifiers
source                  1..260
                        mol_type = protein
                        organism = synthetic construct
SEQUENCE: 453
QGQSGQCISP RGCPDGPYVM YGGGSSGGSH VPRQVLSGRS ANGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 454          moltype = AA  length = 259
FEATURE                 Location/Qualifiers
source                  1..259
                        mol_type = protein
                        organism = synthetic construct
SEQUENCE: 454
QGQSGQCISP RGCPDGPYVM YGGGSSGGST ARGPALAHGL FGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 455          moltype = AA  length = 257
FEATURE                 Location/Qualifiers
source                  1..257
                        mol_type = protein
                        organism = synthetic construct
SEQUENCE: 455
QGQSGQCISP RGCPDGPYVM YGGGSSGGST ARGPVPRQVG GGSQILLTQS PVILSVSPGE  60
RVSFSCRASQ SIGTNIHWYQ QRTNGSPRLL IKYASESISG IPSRFSGSGS GTDFTLSINS  120
VESEDIADYY CQQNNNWPTT FGAGTKLELK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 456          moltype = AA  length = 258
FEATURE                 Location/Qualifiers
source                  1..258
                        mol_type = protein
                        organism = synthetic construct
SEQUENCE: 456
QGQSGQCISP RGCPDGPYVM YGGGSSGGSA PRSALAHGLF GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 457          moltype = AA  length = 259
FEATURE                 Location/Qualifiers
source                  1..259
                        mol_type = protein
                        organism = synthetic construct
SEQUENCE: 457
QGQSGQCISP RGCPDGPYVM YGGGSSGGSA LAHGLFAPRS FGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
```

-continued

```
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 458          moltype = AA  length = 258
FEATURE                 Location/Qualifiers
source                  1..258
                        mol_type = protein
                        organism = synthetic construct
SEQUENCE: 458
QGQSGQCISP RGCPDGPYVM YGGGSSGGSH VPRQVAPRSF GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 459          moltype = AA  length = 259
FEATURE                 Location/Qualifiers
source                  1..259
                        mol_type = protein
                        organism = synthetic construct
SEQUENCE: 459
QGQSGQCISP RGCPDGPYVM YGGGSSGGSA LAHGLPTFVH LGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 460          moltype = AA  length = 259
FEATURE                 Location/Qualifiers
source                  1..259
                        mol_type = protein
                        organism = synthetic construct
SEQUENCE: 460
QGQSGQCISP RGCPDGPYVM YGGGSSGGSG LPTFVHLPRQ VGGGSQILLT QSPVILSVSP  60
GERVSFSCRA SQSIGTNIHW YQQRTNGSPR LLIKYASESI SGIPSRFSGS GSGTDFTLSI  120
NSVESEDIAD YYCQQNNNWP TTFGAGTKLE LKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 461          moltype = AA  length = 257
FEATURE                 Location/Qualifiers
source                  1..257
                        mol_type = protein
                        organism = synthetic construct
SEQUENCE: 461
QGQSGQCISP RGCPDGPYVM YGGGSSGGSA ANALAHGLFG GGSQILLTQS PVILSVSPGE  60
RVSFSCRASQ SIGTNIHWYQ QRTNGSPRLL IKYASESISG IPSRFSGSGS GTDFTLSINS  120
VESEDIADYY CQQNNNWPTT FGAGTKLELK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 462          moltype = AA  length = 258
FEATURE                 Location/Qualifiers
source                  1..258
                        mol_type = protein
                        organism = synthetic construct
SEQUENCE: 462
QGQSGQCISP RGCPDGPYVM YGGGSSGGSG PTNALAHGLF GGGSQILLTQ SPVILSVSPG  60
ERVSFSCRAS QSIGTNIHWY QQRTNGSPRL LIKYASESIS GIPSRFSGSG SGTDFTLSIN  120
SVESEDIADY YCQQNNNWPT TFGAGTKLEL KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 463          moltype =   length =
SEQUENCE: 463
000

SEQ ID NO: 464          moltype =   length =
SEQUENCE: 464
000

SEQ ID NO: 465          moltype =   length =
SEQUENCE: 465
000

SEQ ID NO: 466          moltype =   length =
SEQUENCE: 466
000
```

-continued

```
SEQ ID NO: 467         moltype =   length =
SEQUENCE: 467
000

SEQ ID NO: 468         moltype =   length =
SEQUENCE: 468
000

SEQ ID NO: 469         moltype =   length =
SEQUENCE: 469
000

SEQ ID NO: 470         moltype =   length =
SEQUENCE: 470
000

SEQ ID NO: 471         moltype =   length =
SEQUENCE: 471
000

SEQ ID NO: 472         moltype =   length =
SEQUENCE: 472
000

SEQ ID NO: 473         moltype =   length =
SEQUENCE: 473
000

SEQ ID NO: 474         moltype =   length =
SEQUENCE: 474
000

SEQ ID NO: 475         moltype =   length =
SEQUENCE: 475
000

SEQ ID NO: 476         moltype =   length =
SEQUENCE: 476
000

SEQ ID NO: 477         moltype =   length =
SEQUENCE: 477
000

SEQ ID NO: 478         moltype =   length =
SEQUENCE: 478
000

SEQ ID NO: 479         moltype =   length =
SEQUENCE: 479
000

SEQ ID NO: 480         moltype = AA  length = 265
FEATURE                Location/Qualifiers
source                 1..265
                       mol_type = protein
                       organism = synthetic construct
SEQUENCE: 480
QGQSGQCISP RGCPDGPYVM YGSSGGSGGS GGSGISSGLL SGRSDNPGGG SQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 481         moltype = AA  length = 270
FEATURE                Location/Qualifiers
source                 1..270
                       mol_type = protein
                       organism = synthetic construct
SEQUENCE: 481
QGQSGQCISP RGCPDGPYVM YGSSGGSGGS GGSGAVGLLA PPGGLSGRSD NPGGGSQILL  60
TQSPVILSVS PGERVSFSCR ASQSIGTNIH WYQQRTNGSP RLLIKYASES ISGIPSRFSG  120
SGSGTDFTLS INSVESEDIA DYYCQQNNNW PTTFGAGTKL ELKRTVAAPS VFIFPPSDEQ  180
LKSGTASVVC LLNNFYPREA KVQWKVDNAL QSGNSQESVT EQDSKDSTYS LSSTLTLSKA  240
DYEKHKVYAC EVTHQGLSSP VTKSFNRGEC                                   270

SEQ ID NO: 482         moltype = AA  length = 255
FEATURE                Location/Qualifiers
source                 1..255
```

```
                         mol_type = protein
                         organism = synthetic construct
SEQUENCE: 482
QGQSGQCISP RGCPDGPYVM YGGGSSGGSI SSGLLSSGGG SQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                   255

SEQ ID NO: 483           moltype = AA  length = 260
FEATURE                  Location/Qualifiers
source                   1..260
                         mol_type = protein
                         organism = synthetic construct
SEQUENCE: 483
QGQSGQCISP RGCPDGPYVM YGSSGGSGGS GGSGISSGLL SSGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 484           moltype = AA  length = 255
FEATURE                  Location/Qualifiers
source                   1..255
                         mol_type = protein
                         organism = synthetic construct
SEQUENCE: 484
QGQSGQCISP RGCPDGPYVM YGGGSSGGSA VGLLAPPGGG SQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                   255

SEQ ID NO: 485           moltype = AA  length = 261
FEATURE                  Location/Qualifiers
source                   1..261
                         mol_type = protein
                         organism = synthetic construct
SEQUENCE: 485
QGQSGQCISP RGCPDGPYVM YGSSGGSGGS GGSGPAVGLL APPGGGSQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 486           moltype = AA  length = 255
FEATURE                  Location/Qualifiers
source                   1..255
                         mol_type = protein
                         organism = synthetic construct
SEQUENCE: 486
QGQSGQCISP RGCPDGPYVM YGGGSSGGSG PSHLVLTGGG SQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                   255

SEQ ID NO: 487           moltype = AA  length = 260
FEATURE                  Location/Qualifiers
source                   1..260
                         mol_type = protein
                         organism = synthetic construct
SEQUENCE: 487
QGQSGQCISP RGCPDGPYVM YGSSGGSGGS GGSGGPSHLV LTGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 488           moltype = AA  length = 261
FEATURE                  Location/Qualifiers
source                   1..261
                         mol_type = protein
                         organism = synthetic construct
SEQUENCE: 488
QGQSGQCISP RGCPDGPYVM YGGGSSGGSI SSGLLSGRSD NHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
```

-continued

```
CEVTHQGLSS PVTKSFNRGE C                                         261

SEQ ID NO: 489          moltype = AA  length = 260
FEATURE                 Location/Qualifiers
source                  1..260
                        mol_type = protein
                        organism = synthetic construct
SEQUENCE: 489
QGQSGQCISP RGCPDGPYVM YGGGSSGGSI SSGLLSGRSD NHGGGSQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                           260

SEQ ID NO: 490          moltype = AA  length = 265
FEATURE                 Location/Qualifiers
source                  1..265
                        mol_type = protein
                        organism = synthetic construct
SEQUENCE: 490
QGQSGQCISP RGCPDGPYVM YGGGSSGGSA VGLLAPPGGL SGRSDNHGGG SQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                      265
```